US012066430B2

(12) United States Patent
Bethune et al.

(10) Patent No.: US 12,066,430 B2
(45) Date of Patent: Aug. 20, 2024

(54) TROGOCYTOSIS MEDIATED EPITOPE DISCOVERY METHODS

(71) Applicant: California Institute of Technology, Pasadena, CA (US)

(72) Inventors: Michael T. Bethune, South San Francisco, CA (US); Jocelyn T. Kim, Pasadena, CA (US); David Baltimore, Pasadena, CA (US); Guideng Li, Pasadena, CA (US); Stephanie Wong, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 745 days.

(21) Appl. No.: 16/633,451

(22) PCT Filed: Jul. 24, 2018

(86) PCT No.: PCT/US2018/043542
§ 371 (c)(1),
(2) Date: Jan. 23, 2020

(87) PCT Pub. No.: WO2019/023269
PCT Pub. Date: Jan. 31, 2019

(65) Prior Publication Data
US 2020/0309765 A1 Oct. 1, 2020

Related U.S. Application Data

(60) Provisional application No. 62/536,828, filed on Jul. 25, 2017.

(51) Int. Cl.
*G01N 33/50* (2006.01)
*G01N 33/566* (2006.01)
*G06F 16/27* (2019.01)

(52) U.S. Cl.
CPC ......... *G01N 33/505* (2013.01); *G01N 33/566* (2013.01); *G06F 16/27* (2019.01)

(58) Field of Classification Search
CPC .......................... G01N 33/505; G01N 33/566
See application file for complete search history.

(56) References Cited

U.S. PATENT DOCUMENTS

| 8,507,205 | B2 | 8/2013 | Faham et al. |
| 9,115,402 | B2 | 8/2015 | Hacohen et al. |
| 9,347,099 | B2 | 5/2016 | Faham et al. |
| 9,506,119 | B2 | 11/2016 | Faham et al. |
| 2003/0003535 | A1 | 1/2003 | Reiter |
| 2008/0219947 | A1 | 9/2008 | Linette et al. |
| 2009/0117153 | A1 | 5/2009 | Hansen et al. |
| 2017/0003288 | A1 | 1/2017 | Heath et al. |
| 2017/0199961 | A1 | 7/2017 | Yelensky et al. |

FOREIGN PATENT DOCUMENTS

| WO | WO2016196691 A2 | 12/2016 | |
| WO | WO 2017/106638 A1 | 6/2017 | |
| WO | WO2017136748 | * 8/2017 | .......... C12N 5/0783 |
| WO | WO 2018/075693 | 4/2018 | |
| WO | WO 2018/085453 | 5/2018 | |
| WO | WO 2018/165475 | 9/2018 | |

OTHER PUBLICATIONS

Haastert et al., T cells at the site of autoimmune inflammation show increased potential for trogocytosis. PLoS One 8(12): e81404, 2013. (Year: 2013).*
Hudrisier et al., T cell activation correlates with an increased proportion of antigen among the materials acquired from target cells. Eur. J. Immunol. 35, 2284-2294, 2005. (Year: 2005).*
Day et al., K-562 cells lack MHC class II expression due to an alternatively spliced CIITA transcript with a truncated coding region. Leukemia Research 1027-1038, 2003. (Year: 2003).*
Jurgens et al. Transduction of Primary Lymphocytes with Epstein-Barr Virus (EBV) Latent Membrane Protein-Specific T-Cell Receptor Induces Lysis of Virus-infected Cells: A Novel Strategy for the Treatment of Hodgkin's Disease and Nasopharyngeal Carcinoma. J. Clin. Immunol. 26, 22-32, 2006. (Year: 2006).*
Chatelut et al. Establishment and Characterization of a Human T-Lymphocyte Cell Line Immortalized by SV40 and with Abnormal Expression of TCR/CD3. Scand. J. Immunol. 48, 659-666, 1998. (Year: 1998).*
Murdjeva et al. The Programmed Cell Death of an Immature Thymocyte Cell Line Transgenic for an TCR and the c-myc Proto-Oncogene. Develop. Immunol. 4, 279-288, 1996. (Year: 1996).*
Tanaka et al. In vitro negative selection of αβ Tcell receptor transgenic thymocytes by conditionally immortalized thymic cortical epithelial cell lines and dendritic cells. Eur. J. Immunol. 23, 2614-2621, 1993. (Year: 1993).*
Primi et al. Rearrangement and expression of T cell receptor and immunoglobulin loci in immortalized CD4-CD8-cell lines. Eur. J. Immunol. 18, 1101-1109, 1988. (Year: 1988).*
Saadawi et al. Dominant clones in immortalized T-cell lines from rheumatoid arthritis synovial membranes. Tissue antigens. 49, 431-437, 1997. (Year: 1997).*
Bardi et al., "HLA-A, B and DRB1 allele and haplotype frequencies in volunteer bone marrow donors from the north of Parana State," Rev Bras Hematol Hemoter. 2012; 34(1): 25-30.

(Continued)

*Primary Examiner* — Elly-Gerald Stoica
(74) *Attorney, Agent, or Firm* — KNOBBE, MARTENS, OLSON & BEAR, LLP

(57) ABSTRACT

Disclosed herein are trogocytosis based TCR ligand discovery platforms and methods of using the same, trogocytosis based TCR discovery platforms and methods of using the same, and trogocytosis based ligand discovery platforms and methods of using the same. Also disclosed herein are isolated cells, nucleotides, sequences, and sequence databases produced using trogocytosis based discovery platforms.

21 Claims, 39 Drawing Sheets

Specification includes a Sequence Listing.

(56) References Cited

OTHER PUBLICATIONS

Bassani-Sternberg, Michael, et al., "Mass Spectrometry-Based Antigen Discovery For Cancer Immunotherapy," Current Opinion in Immunology 2016, 41:9-17.
Bentzen, Amalie Kai, et al., "Large-Scale Detection Of Antigen-Specific T Cells Using Peptide-MHC-I Multimers Labeled With DNA Barcodes," Nature Biotechnology, vol. 34, No. 10, Oct. 2016, pp. 1037-1048.
Bethune, Michael T., et al., "Personalized T-cell-mediated cancer immunotherapy: progress and challenges," Current Opinion in Biotechbology 2017, 48: 142-152, May 2017.
Bethune, Michael T., et al., "Preparation Of Peptide-MHC And T-Cell Receptor Dextramers By Biotinylated Dextran Doping," BioTechniques 62: 123-130, Mar. 2017, pp. 123-130.
Briggs, Adrian W., et al., "Tumor-Infiltrating Immune Repertoires Captured By Single-Cell Barcoding In Emulsion," available at https://doi.org/10.1101/134841, version posted May 5, 2017.
Brinkmann et al., "The Making of Bispecific Antibodies," MABS, 2017, vol. 9, No. 2, 182-212.
Cibulskis, Kristian, et al., "Sensitive Detection Of Somatic Point Mutations In Impure And Heterogeneous Cancer Samples," Nature Biotechnology, vol. 31, No. 3, Mar. 2013, pp. 213-221.
Daubeuf, Sadrine, et al., "The Direction of Plasma Membrane Exchange between Lymphocytes and Accessory Cells by Trogocytosis is Influenced by the Nature of the Accessory Cell," J Immunol 2010; 184: 1897-1908, prepublished online Jan. 20, 2010.
Daubeuf, Sadrine, et al., "A simple Trogocytosis-Based Method to Detect, Quantify, Characterize, and Ourify Antigen-Specific Live Lymphocytes by Flow Cytometry, via their Capture of Membrane Fragments from Antigen-Presenting cells," Nature Protocols, vol. 1, No. 6, 2006 pp. 2536-2542.
Dembic, Zlatko, et al., "Transfer of specificity by Murine α and β T-cell receptor genes," Nature, vol. 320, Mar. 1986.
Dolton, Garry, et al., "More tricks with tetramers: a practical guide to staining T cells with peptide-MHC multimers," Immunology, 146, 2015, pp. 11-12.
Fritsch et al., "HLA-binding Properties of Tymore Neoepitopes in Humans," 2014, Cancer Immunol Res., 2:522-529.
Gee, Marvin, H., et al., "Antigen Identification for Orphan T Cell Receptors Expressed on Tumor-infiltrating Lymphocytes," Cell 172, pp. 549-563, Jan. 25, 2018.
Gonzalez-Galarza, F.F. et al., "Allele frequency net 2015 update: new features for HLA epitopes, KIR and disease and HLA adverse drug reaction associations," Nucleic acids research 43, D784-788 (2015).
Gros, A. et al., "PD-1 identifies the patient-specific CD8(+) tumor-reactive repertoire infiltrating human tumors," The Journal of clinical investigation 124, 2246-2259 (2014).
Gros, A. et al., "Prospective identification of neoantigen-specific lymphocytes in the peripheral blood of melanoma patients," Nature medicine 22, 433-438 (2016).
Han, A., et al., "Linking T-cell receptor sequence to functional phenotype at the single-cell level," Nature biotechnology 32, 684-692 (2014).
Ignatowicz et al., "Cell Surface Expression of Class II MHC Proteins Bound by a Single Peptide," J Immunol. Apr. 15, 1995;154(8):3852-62.
International Search Report dated Oct. 12, 2018 in Application No. PCT/US18/43542 in 15 pages.
Irvine, D.J., et al., "Direct observation of ligand recognition by T cells," Nature 419, 845-849 (2002).
Joly, E., et al., "What is trogocytosis and what is its purpose?" Nat Immunol 4, 815 (2003).
Kim, D. et al., "TopHat2: accurate alignment of transcriptomes in the presence of insertions, deletions and gene fusions," Genome Biol 14 (2013).
Koboldt, D.C., et al., "VarScan 2: Somatic mutation and copy number alteration discovery in cancer by exome sequencing," Genome Res 22, 568-576 (2012).
Kontos, S., et al., "Engineering antigen-specific immunological tolerance," Current opinion in immunology 35, 80-88 (2015).
Linnemann, C., Mezzdra, R. & Schumacher, T.N, "TCR repertoires of intratumoral T-cell subsets," Immunological reviews 257, 72-82 (2014).

Lu, Y.C. & Robbins, P.F., "Cancer immunotherapy targeting neoantigens," Semin Immunol 28, 22-27 (2016).
Lundegaard, C. et al. "NetMHC-3.0: accurate web accessible predictions of human, mouse and monkey MHC class I affinities for peptides of length 8-11," Nucleic Acids Res 36, W509-W512 (2008).
Machlenkin, A. et al. "Capture of tumor cell membranes by trogocytosis facilitates detection and isolation of tumor-specific functional CTLs," Cancer research 68, 2006-2013 (2008).
Morgan, R.A. et al. "Cancer regression and neurological toxicity following anti-MAGE-A3 TCR gene therapy," Journal of immunotherapy 36, 133-151 (2013).
Neri, S., et al,."Calcein-acetyoxymethyl cytotoxicity assay: standardization of a method allowing additional analyses on recovered effector cells and supernatants," Clinical and diagnostic laboratory immunology, vol. 8, No. 6, pp. 1131-1135 (Nov. 2001).
Novak et al., "MHC Class II Tetramers Identify Peptide-Specific Human CD4(+) T Cells Proliferating in Response to Influenza A Antigen," 1999, J. Clin. Invest. 104:R63-R67.
Pasetto, A. et al. "Tumor- and Neoantigen-Reactive T-cell Receptors Can Be Identified Based on Their Frequency in Fresh Tumor," Cancer immunology research 4, 734-743 (2016).
Prickett, T.D. et al., "Durable Complete Response from Metastatic Melanoma after Transfer of Autologous T Cells Recognizing 10 Mutated Tumor Antigens," Cancer immunology research 4, 669-678 (2016).
Puaux, A.L. et al., "A very rapid and simple assay based on trogocytosis to detect and measure specific T and B cell reactivity by flow cytometry," European journal of immunology 36, 779-788 (2006).
Ramos, A.H. et al., "Oncotator: Cancer Variant Annotation Tool," Hum Mutat 36, E2423-E2429 (2015).
Rosenberg, S.A. & Restifo, N.P., "Adoptive cell transfer as personalized immunotherapy for human cancer," Science 348, 62-68 (2015).
Schumacher, T.N. & Schreiber, R.D., "Neoantigens in cancer immunotherapy," Science 348, 69-74 (2015).
Shi, H.B. et al., "Acquired Resistance and Clonal Evolution in Melanoma during BRAF Inhibitor Therapy," Cancer Discov 4, 80-93 (2014).
Skipper, J.C. et al., "Mass-spectrometric evaluation of HLA-A*0201-associated peptides identifies dominant naturally processed forms of CTL epitopes from MART-1 and gp100," International journal of cancer 82, 669-677 (1999).
Sollid, L.M. et al., "Small bowel, celiac disease and adaptive immunity," Digestive diseases 33, 115-121 (2015).
Stronen, E. et al., "Targeting of cancer neoantigens with donor-derived T cell receptor repertoires," Science 352, 1337-1341 (2016).
Tran, E. et al., "Cancer immunotherapy based on mutation-specific CD4+ T cells in a patient with epithelial cancer," Science 344, 641-645 (2014).
Trapnell, C. et al., "Differential gene and transcript expression analysis of RNA-seq experiments with TopHat and Cufflinks," Nat Protoc 7, 562-578 (2012).
Wang, Rong-Fu, et al., Immune Targets and Neoantigens for Cancer Immunotherapy and Precision Medicine, Cell Research (2017) 27:11-37.
Wooldridge, L. et al., "Interaction between the CD8 coreceptor and major histocompatibility complex class I stabilizes T cell receptor-antigen complexes at the cell surface," The Journal of biological chemistry 280, 27491-27501 (2005).
He et al., Interferon [gamma] Stimulates Cellular Maturation of Dendritic Cell Line DC2.4 Leading to Induction of Efficient Cytotoxic T Cell Responses and Antitumor Immunity, Cellular & Molecular Immunology 105, 2007.
He, et al., Bidirectional membrane molecule transfer between dendritic and T cells, Biochemical and Biophysical Research Communications, vol. 359, No. 2, 2007.
Office Action for Chinese Patent Application No. 201880062443X in 18 pages, dated Nov. 4, 2022.
Supplementary European Search Report for European Patent Application No 18838444.0 in 8 pages dated Mar. 22, 2021.
Office Action for Chinese Patent Application No. 201880062443X in 6 pages, dated Aug. 5, 2023.

\* cited by examiner

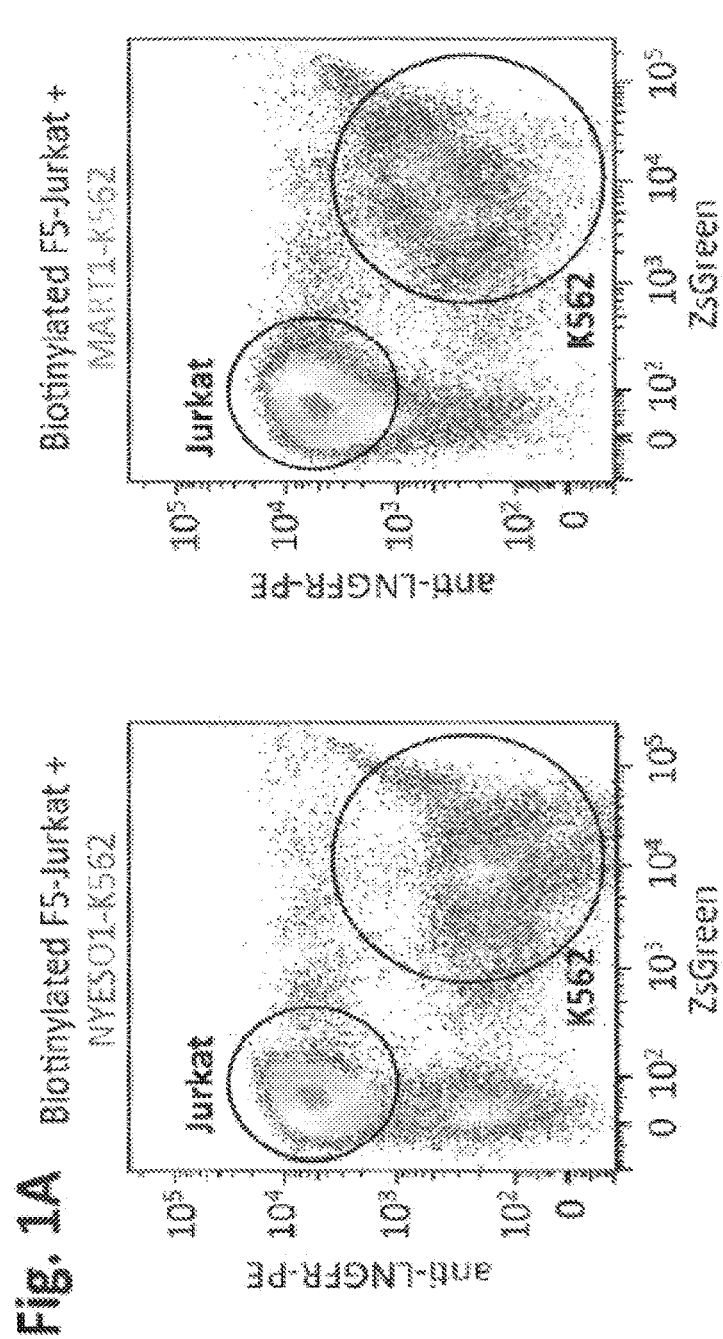

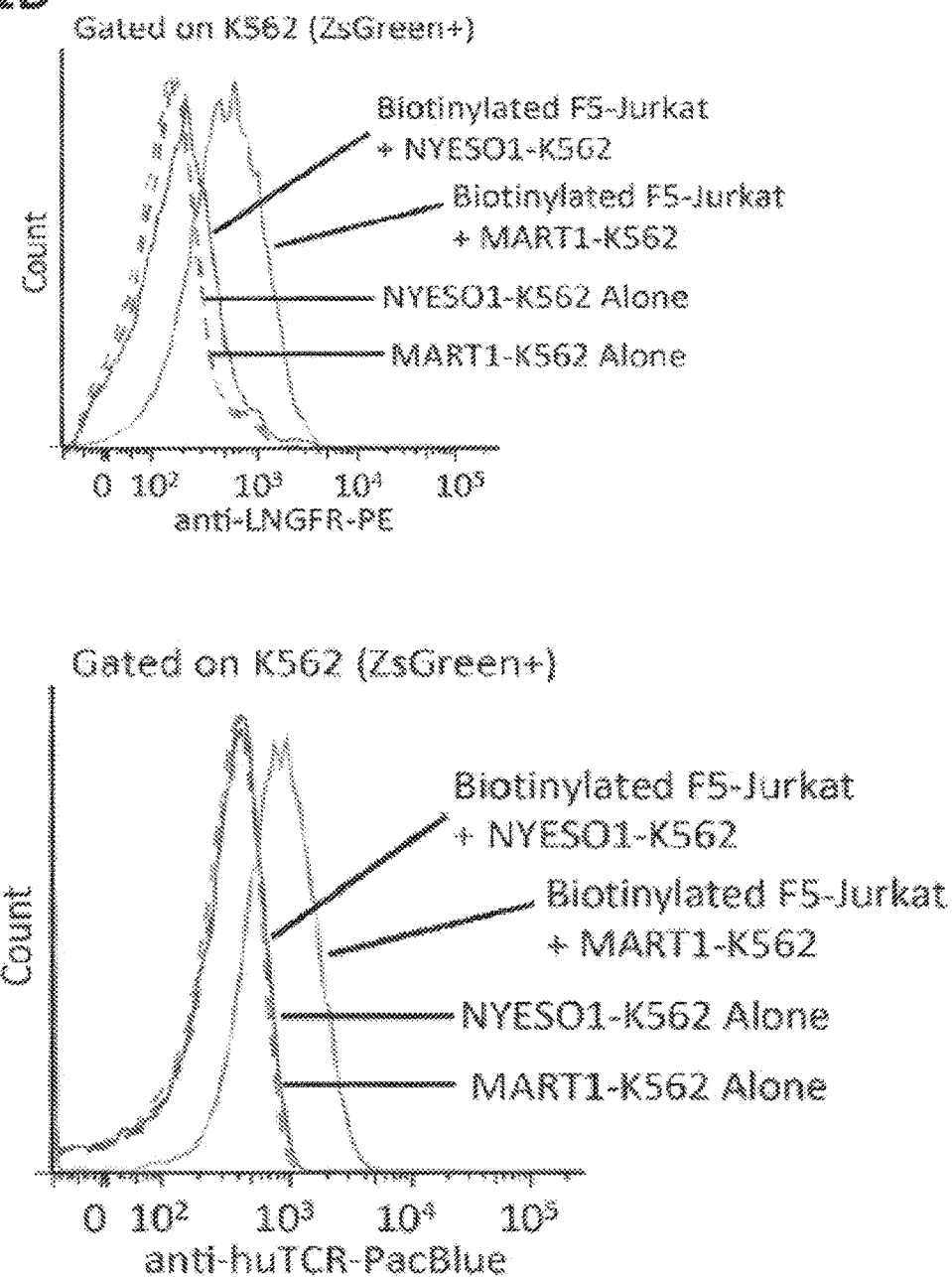

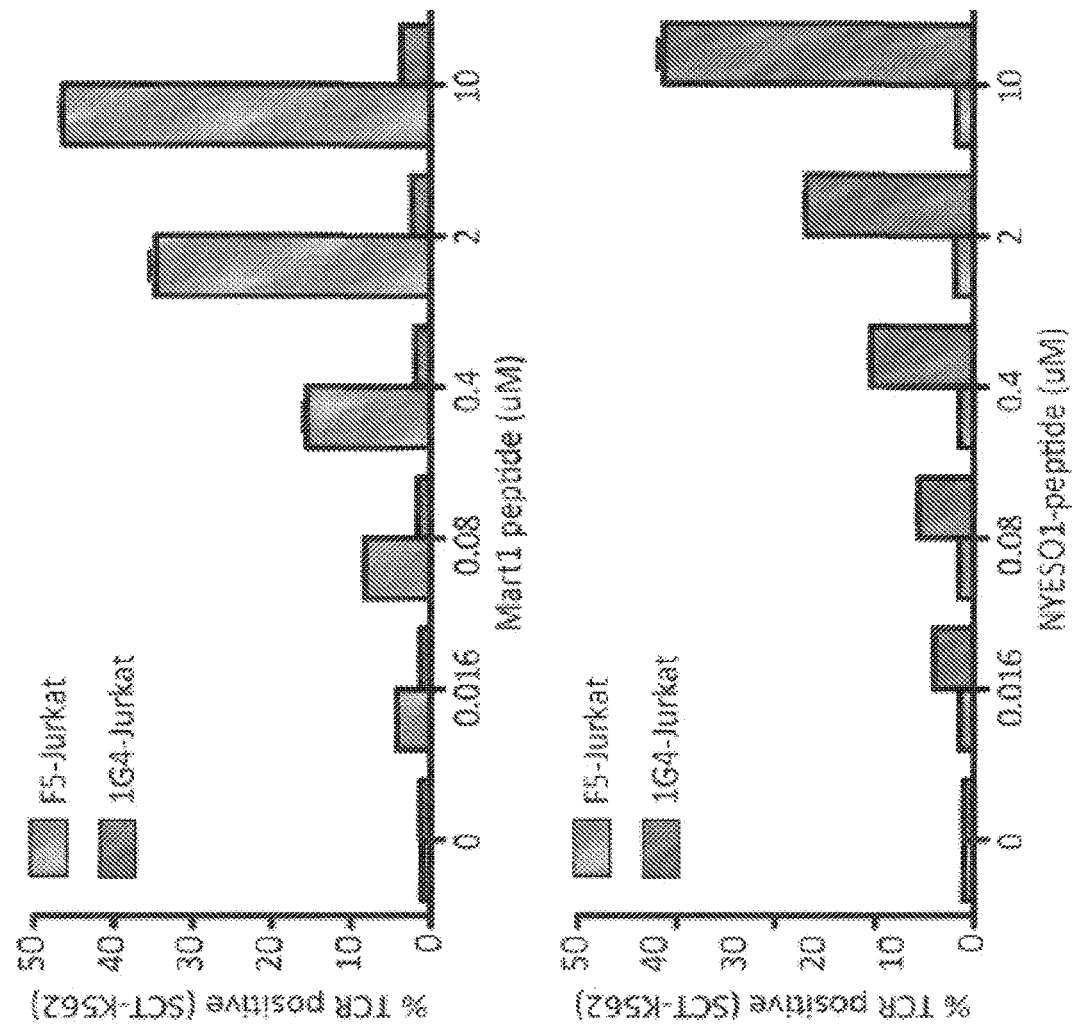

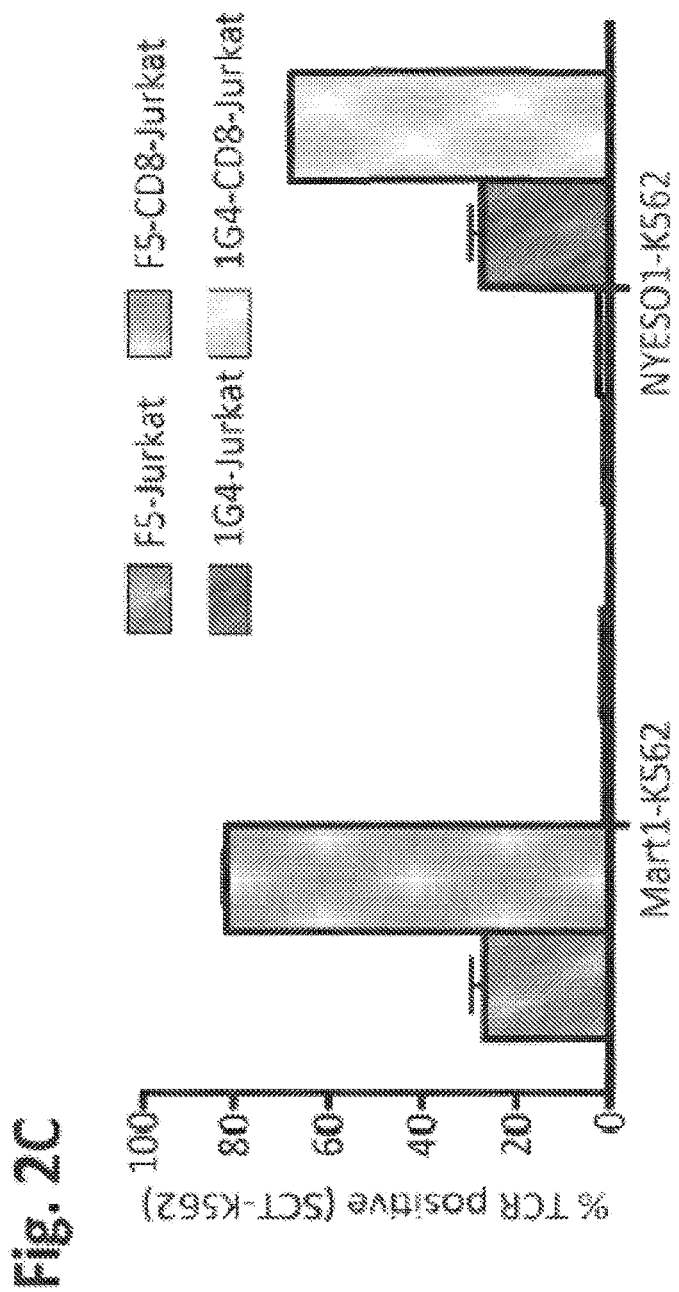

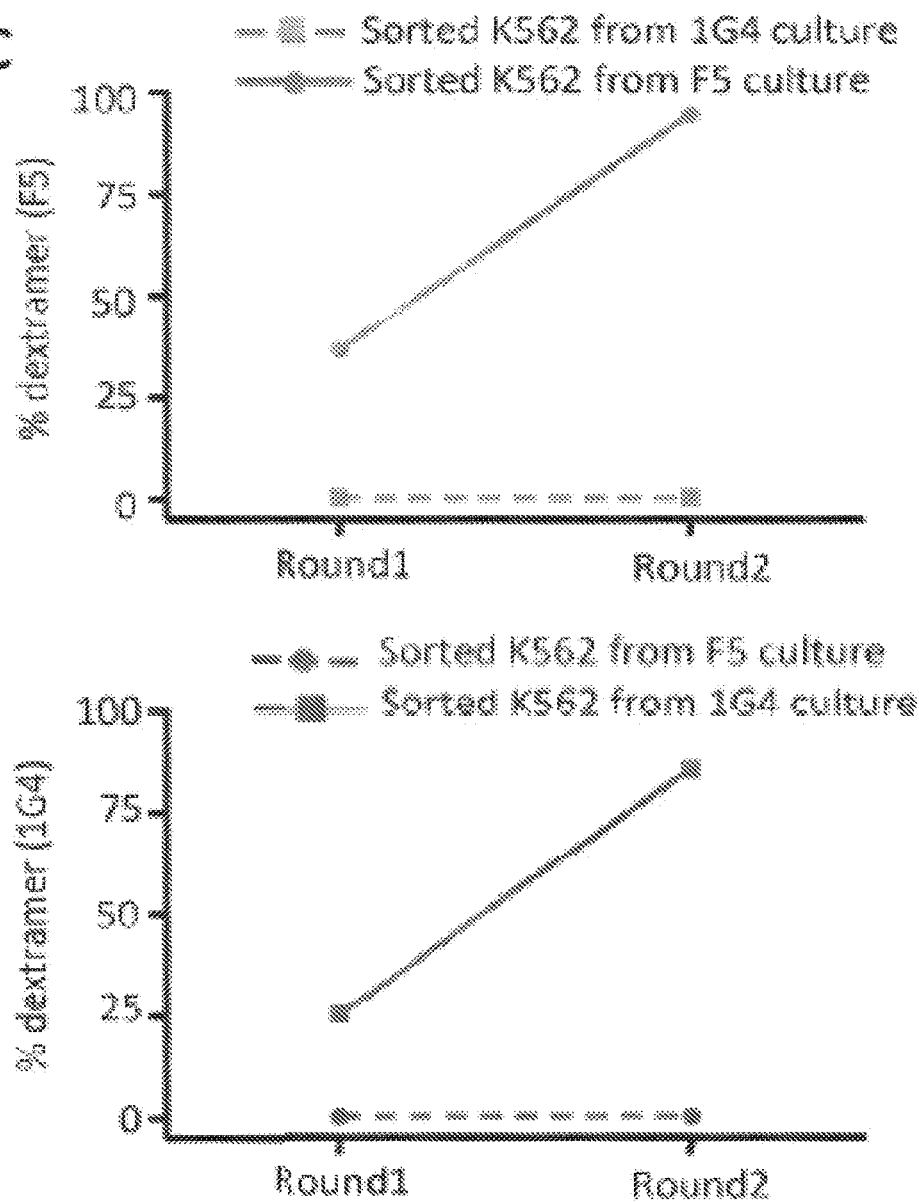

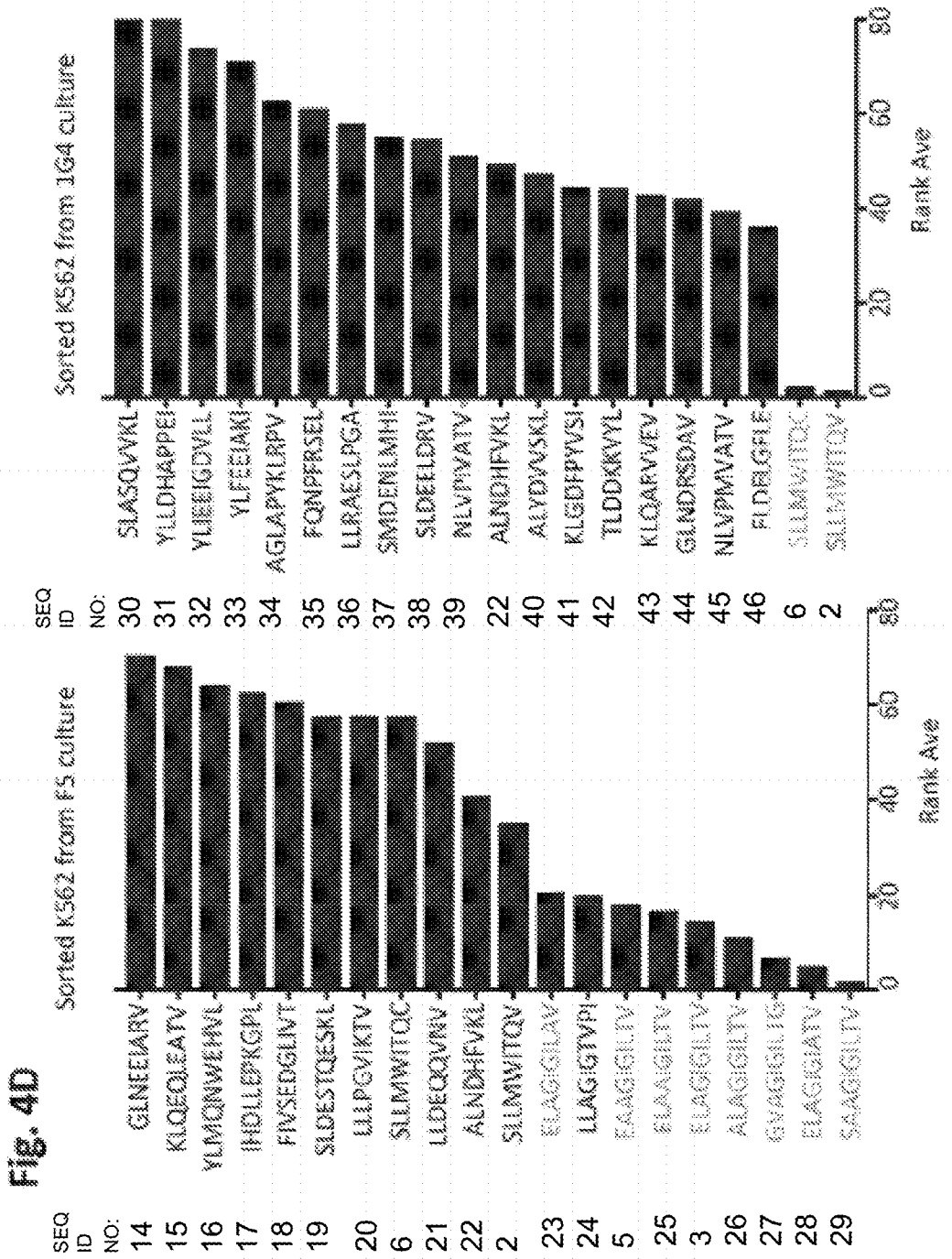

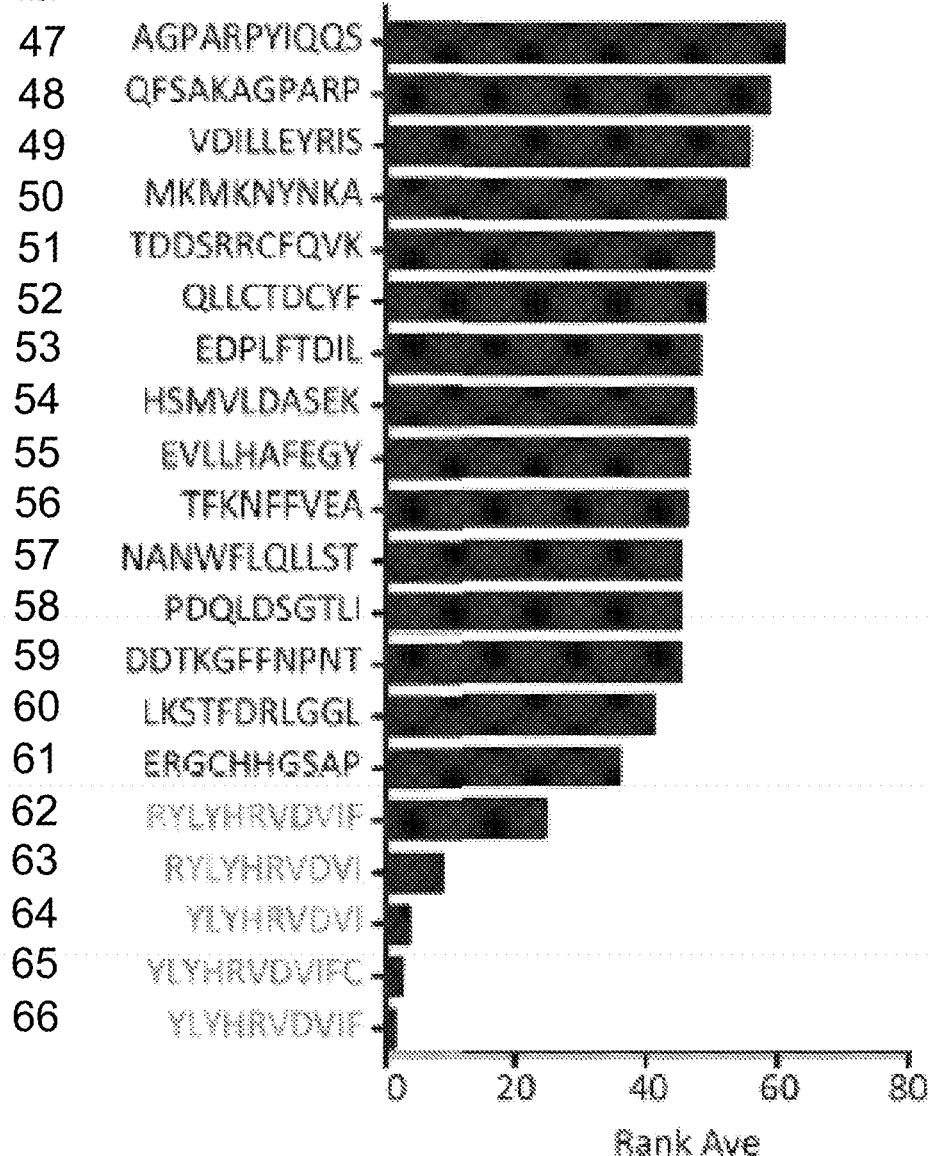

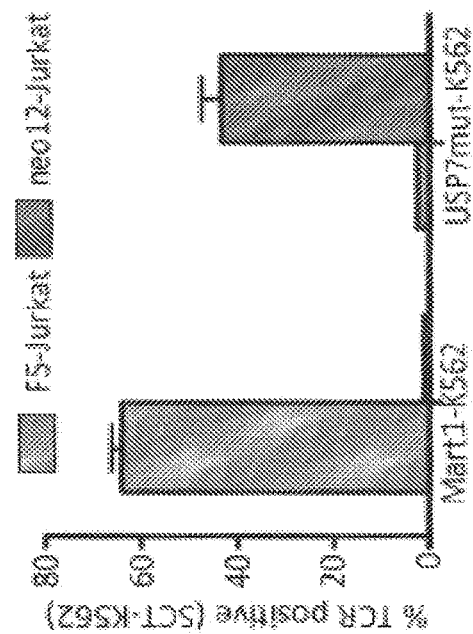
Fig. 5C
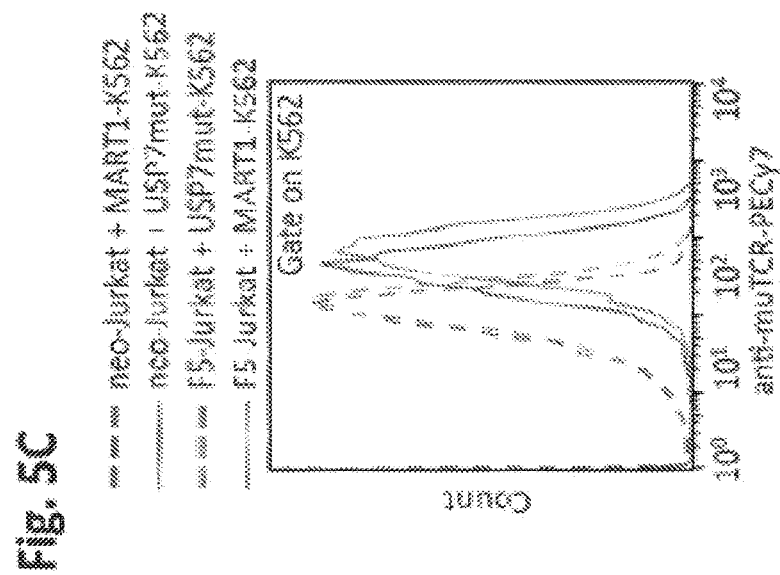

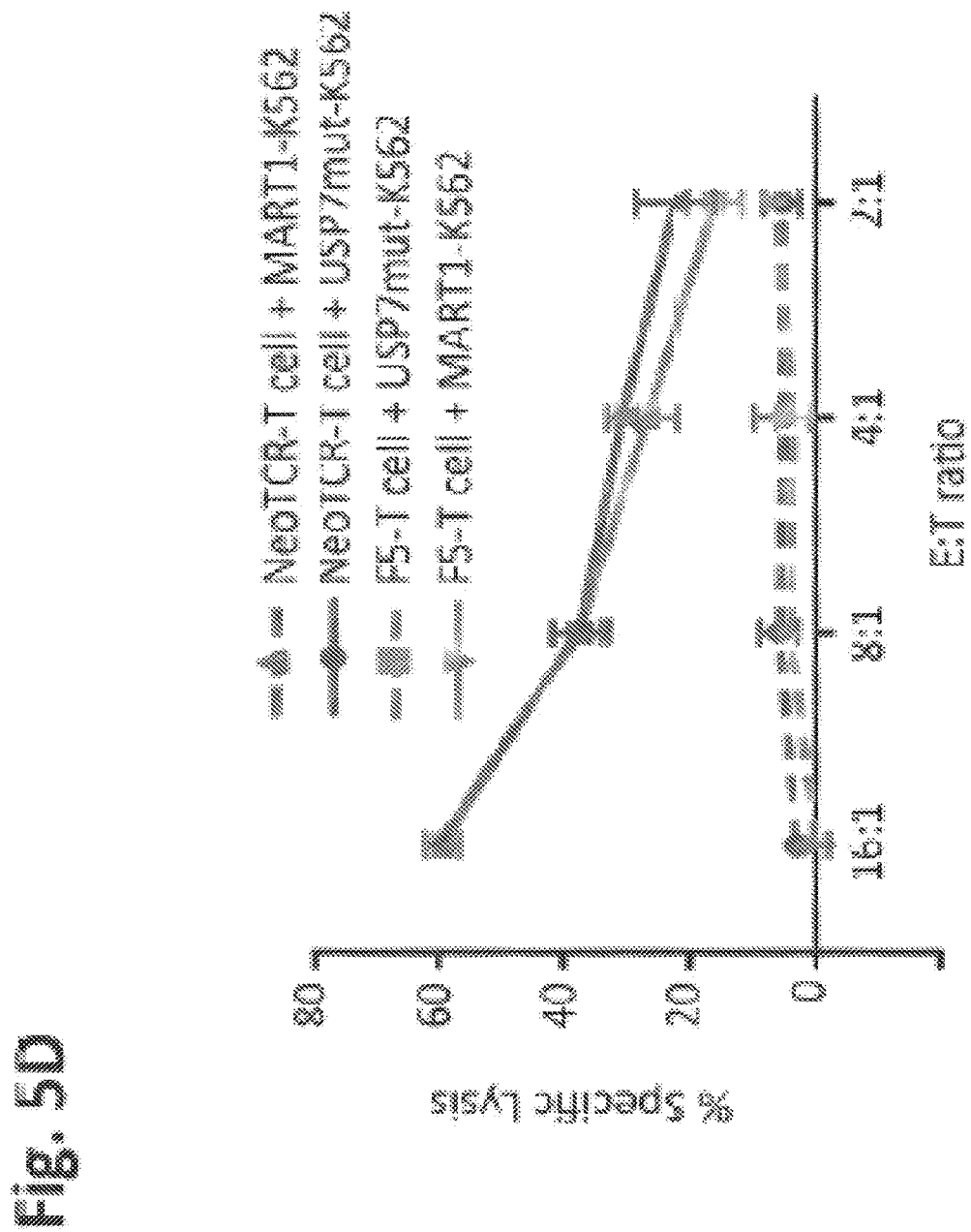

— 1G4-Jurkat + NYESO1-K562
— 1G4-Jurkat + A2-K562 pulsed with no peptide
— 1G4-Jurkat + A2-K562 pulsed with 0.016 uM NYESO1 peptide
— 1G4-Jurkat + A2-K562 pulsed with 0.08 uM NYESO1 peptide
— 1G4-Jurkat + A2-K562 pulsed with 0.4 uM NYESO1 peptide
— 1G4-Jurkat + A2-K562 pulsed with 2 uM NYESO1 peptide
— 1G4-Jurkat + A2-K562 pulsed with 10 uM NYESO1 peptide — F5-Jurkat + MART1-K562
— F5-Jurkat + A2-K562 pulsed with no peptide
— F5-Jurkat + A2-K562 pulsed with GIGILTVIL peptide
— F5-Jurkat + A2-K562 pulsed with ILVILGVL peptide
— F5-Jurkat + A2-K562 pulsed with AAGIGILTVI peptide
— F5-Jurkat + A2-K562 pulsed with EAAGIGILTV peptide
— F5-Jurkat + A2-K562 pulsed with ELAGIGILTV peptide
— F5-Jurkat + A2-K562 pulsed with AAGIGILTV peptide

- 1G4-Jurkat + NYESO1-K562
- 1G4-Jurkat + A2-K562 pulsed with no peptide
- 1G4-Jurkat + A2-K562 pulsed with GIGILTVIL peptide
- 1G4-Jurkat + A2-K562 pulsed with ILVILGVL peptide
- 1G4-Jurkat + A2-K562 pulsed with AAGIGILTVI peptide
- 1G4-Jurkat + A2-K562 pulsed with EAAGIGILTV peptide
- 1G4-Jurkat + A2-K562 pulsed with ELAGIGILTV peptide
- 1G4-Jurkat + A2-K562 pulsed with AAGIGILTV peptide — 1G4-Jurkat + MART1-K562
— 1G4-Jurkat + A2-K562 pulsed with no peptide
— 1G4-Jurkat + A2-K562 pulsed with SLLMWITQV peptide
— 1G4-Jurkat + A2-K562 pulsed with SLLMWITQ peptide
— 1G4-Jurkat + A2-K562 pulsed with SLLMWITQAL peptide
— 1G4-Jurkat + A2-K562 pulsed with SLLMWITQC peptide

- F5-Jurkat + MART1-K562
- F5-Jurkat + A2-K562 pulsed with no peptide
- F5-Jurkat + A2-K562 pulsed with SLLMWITQV peptide
- F5-Jurkat + A2-K562 pulsed with SLLMWITQ peptide
- F5-Jurkat + A2-K562 pulsed with SLLMWITQAL peptide
- F5-Jurkat + A2-K562 pulsed with SLLMWITQC peptide

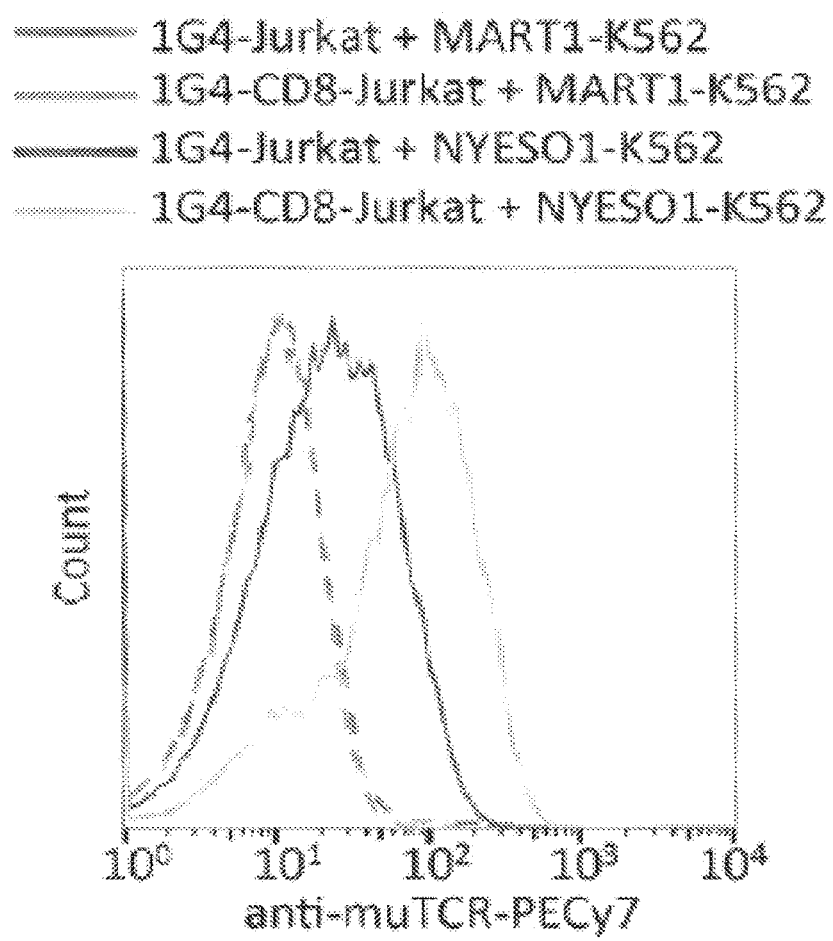

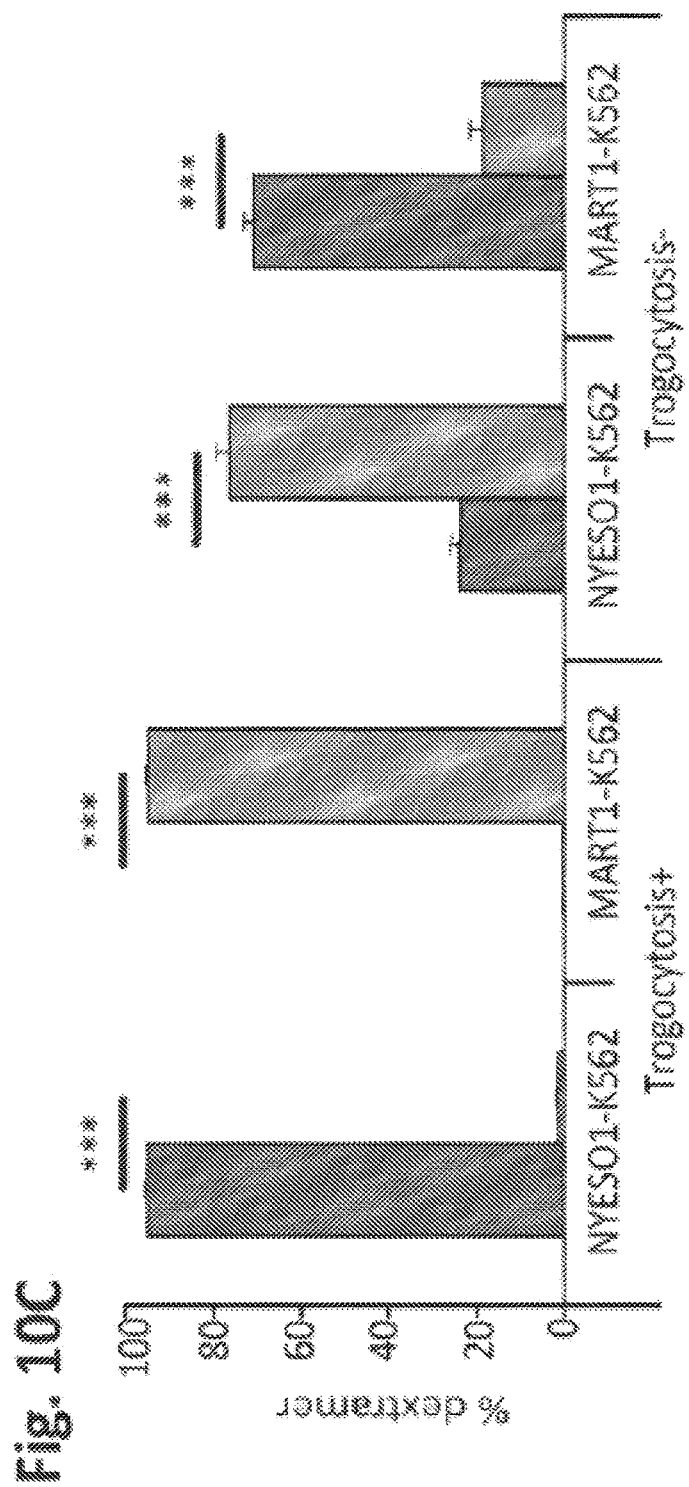

TROGOCYTOSIS MEDIATED EPITOPE DISCOVERY METHODS

CROSS REFERENCE TO RELATED APPLICATIONS

This application is a U.S. national phase application under 35 U.S.C. § 371 of International Application No. PCT/US2018/043542, filed on Jul. 24, 2018, which claims the benefit of U.S. Provisional Application No. 62/536,828, filed Jul. 25, 2017. The content of each of these related applications is hereby incorporated in its entirety by reference, for all purposes.

STATEMENT REGARDING FEDERALLY SPONSORED RESEARCH OR DEVELOPMENT

This invention was made with government support under Grant No. CA199090 awarded by the National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Jan. 23, 2020, is named 2020_01_23_CALTE_150NP_sequencelisting.txt, and is 17,133 bytes in size.

BACKGROUND

T cells mediate adaptive immunity through direct, antigen-specific contact with target cells. The antigenic specificity of each T cell is determined by its unique T cell receptor (TCR)[1], which binds a cognate peptide ligand (epitope) presented on major histocompatibility complex (MHC) protein molecules on a target cell or antigen presenting cell (APC) surface. In general, nascent T cells that recognize self ligands on self MHC are ablated during thymic negative selection, resulting in a repertoire of mature T cells with the capacity to bind foreign ligands presented on infected cells, mutated self ligands (neoepitopes) presented on cancer cells, or various sources of ligands presented on APCs. In this way, TCR antigenic specificity directs T cells to help B cells produce and mature antibodies, to activate innate effectors, to maintain immunological tolerance to self, and to directly kill infected and cancerous cells, all in a precisely targeted manner. TCR ligand discovery is useful for characterizing adaptive immune responses to pathogens and tumors as well as inappropriate responses to self and dietary antigens[2,3]. This knowledge also enables clinically beneficial immunotherapies (e.g. TCR gene transfer and vaccines) that initiate, amplify, or attenuate immune responses to target antigens[4,5]. For example, an infected or cancerous target cell presenting a foreign or mutated self peptide ligand can be killed by a cytotoxic T cell expressing a TCR that recognizes the presented epitope. Thus, TCR ligand discovery is a valuable step for elucidating targets of anti-tumor immunity and designing targeted immunotherapies.

There is an unmet need for robust, high-throughput, unbiased TCR ligand discovery technologies. Peptide-MHC (pMHC) multimer technologies enable monitoring of T cell-mediated responses to a selected panel of antigens[6] but in general are limited in use to biased screens directed to previously characterized antigenic targets relevant to an immune response. Screens using pMHC multimers are currently not on the scale of unbiased antibody ligand discovery platforms[7]. In the context of cancer, tumor neoantigens arising from tumor-specific mutations can be discovered through exome sequencing and then used to interrogate T cells using peptide-MHC multimers or neoantigen-transduced antigen-presenting cells[8,9]. However, tumor exome sequencing does not address other immune responses less focused on mutated epitopes (e.g. pathogen-specific immunity, autoimmunity).

An alternative to interrogating a T cell response with pre-selected antigens is to identify TCRs mediating that response and then use these TCRs to interrogate an antigenic library. TCRs mediating an immune response of interest can be identified by deep-sequencing T cells that are phenotypically implicated in that response[10,11] or that are enriched among clonal T cells at the site of that response (e.g. tumor-reactive TCRs are at a high frequency among tumor-infiltrating lymphocytes (TILs))[12,13]. For example, a recent study described an unbiased TCR-ligand discovery method using soluble, fluorescently-labeled reagents derived from orphan TCR ectodomains to screen a yeast cell surface-displayed pMHC library[14]. However, this method requires construction, validation, and screening of separate yeast libraries for each MHC allele and each ligand length to be tested, typically without knowledge of the MHC restriction for the TCR to be tested, as well as production of soluble TCR ectodomains.

Trogocytosis (from the Greek: trogo-, gnaw) is a biological phenomenon by which cells share membrane and membrane-associated proteins while conjugated[15]. Extraction of T cell membrane proteins by a target cell that binds to a T cell has not been reported. Thus, the use of trogocytosis for antigen discovery or paired antigen and TCR discovery is undescribed in the field.

Pairing the antigen specificity of a T cell with the TCR gene is informative and useful. For example, knowledge of the antigens that a T cell subset recognizes can guide the design of therapy. Likewise, knowledge of TCR genes can guide the design of an engineered cell-based therapy. Thus, the ability to screen analyze TCR antigen specificity at the single cell level remains a significant need in the field. However, approaches for antigen-specific T cell pairing that closer resemble an unbiased screening approach, such as those employed in antibody ligand screens, are absent in the field. Thus, improved screening platforms and methods for TCR antigen identification and for antigen-specific T cell pairing are a need in the field.

SUMMARY

The inventors have discovered a trogocytosis-based system that can identify ligands for binding molecules, such as antigenic peptides recognized by TCRs. The trogocytosis-based system can also identify antigen-specific binding molecules, such as antigen-specific TCRs. The trogocytosis-based system is scalable and customizable for different screening applications. Thus, trogocytosis-based systems described herein address several outstanding issues in the field of antigen discovery, particularly in the field of antigen-specific T cell pairing.

Accordingly, disclosed herein is a method of antigen identification comprising the steps of: a) providing one or more antigen-specific T cell receptor (TCR) expressing cell populations; b) providing one or more target cell populations, wherein the target cell populations present one or more antigenic peptides on one or more major histocompatibility complex (MHC) alleles; c) contacting the one or more antigen-specific TCR expressing cell populations with the one or more target cell populations, wherein the contacting comprises providing conditions sufficient for at least one of the one or more antigen-specific TCR expressing cell populations to specifically bind at least one of the one or more target cell populations, and wherein one or more membrane components are transferred between the at least one antigen-specific TCR expressing cell and the at least one target cell following binding; d) isolating or having isolated i) a target cell of interest, wherein the target cell of interest comprises the one or more membrane components transferred from the at least one antigen-specific TCR expressing cell following the contacting step (c), and optionally ii) a TCR expressing cell of interest, wherein the TCR expressing cell of interest comprises the one or more membrane components transferred from the at least one target cell following the contacting step (c); and e) determining or having determined i) a sequence of the one or more antigenic peptides associated with the target cell of interest, ii) at least a portion of a TCR sequence of a TCR peptide associated with the TCR expressing cell of interest, or iii) a sequence of one or more antigenic peptides associated with the target cell of interest and at least a portion of a TCR sequence of a TCR peptide associated with the TCR expressing cell of interest.

Also disclosed herein is a method of antigen identification comprising the steps of: a) providing an antigen-specific T cell population expressing an antigen-specific TCR; b) providing a plurality of target cell populations, wherein the target cell populations present an antigenic peptide on a major histocompatibility complex (MHC) allele; c) contacting the antigen-specific T cell population with the plurality of target cell populations, wherein the contacting comprises providing conditions sufficient for the antigen-specific T cell population to specifically bind at least one of the plurality of target cell populations, and wherein one or more membrane components are transferred between the antigen-specific T cell and the at least one target cell following binding; d) isolating or having isolated i) a target cell of interest, wherein the target cell of interest comprises the one or more membrane components transferred from the antigen-specific TCR expressing cell following the contacting step (c); and e) determining or having determined a sequence of one or more antigenic peptides associated with the target cell of interest, wherein the determining step (e) comprises purifying or having purified one or more polynucleotides from the target cell of interest and sequencing or having sequenced the purified polynucleotide or any polynucleotide generated using the purified polynucleotide as a template.

Also disclosed herein is a method of antigen-specific TCR identification comprising the steps of: a) providing one or more antigen-specific TCR expressing cell populations; b) providing one or more target cell populations, wherein the target cell populations present one or more antigenic peptides on one or more major histocompatibility complex (MHC) alleles; c) contacting the one or more antigen-specific TCR expressing cell populations with the one or more target cell populations, wherein at least one of the one or more antigen-specific TCR expressing cell populations specifically binds at least one of the one or more target cell populations, and wherein one or more membrane components are transferred between the at least one antigen-specific TCR expressing cell and the at least one target cell following binding; d) isolating or having isolated i) a TCR expressing cell of interest, wherein the TCR expressing cell of interest comprises the one or more membrane components transferred from the at least one target cell following the contacting step (c) or wherein the TCR expressing cell of interest demonstrates loss of the one or more membrane components transferred from the at least one antigen-specific TCR expressing cell following the contacting step (c), and optionally ii) a target cell of interest, wherein the target cell of interest comprises the one or more membrane components transferred from the at least one antigen-specific TCR expressing cell following the contacting step (c); and e) determining or having determined i) a sequence of one or more antigenic peptides associated with the target cell of interest, ii) at least a portion of a TCR sequence encoding a TCR peptide associated with the TCR expressing cell of interest, or iii) a sequence of one or more antigenic peptides associated with the target cell of interest and at least a portion of a TCR sequence encoding a TCR peptide associated with the TCR expressing cell of interest.

In some aspects, the one or more antigen-specific TCR expressing cell populations comprises an immortalized cell line. In some aspects, the one or more antigen-specific TCR expressing cell populations comprises one or more antigen-specific T cell populations. In some aspects, the one or more antigen-specific T cell populations is selected from the group consisting of: a cytotoxic T cell (CTL) population, a CD8+ T cell population, a CD4+ T cell population, a primary T cell population, an ex vivo cultured T cell population, a tumor infiltrating T cell population, an autoimmune T cell population, a pathogen-specific T cell population, a regulatory T cell population, an exhausted T cell, a memory T cell population, a Natural Killer T cell population, a gamma-delta (γδ) T cell population, an engineered T cell population, an immortalized T cell line, and combinations thereof. In some aspects, at least one of the one or more antigen-specific T cell populations is isolated from a subject. In some aspects, the subject is known or suspected to have cancer.

In some aspects, at least one of the one or more antigen-specific TCR expressing cell populations are human cells.

In some aspects, at least one of the one or more antigen-specific TCR expressing cell populations comprise one or more exogenous TCRs, optionally wherein the one or more antigen-specific TCR expressing cell populations do not express an endogenous TCR. In some aspects, the one or more exogenous TCRs are encoded for by one or more TCR polynucleotide sequences, wherein the one or more TCR polynucleotide sequences are operably linked to a promoter nucleotide sequence. In some aspects, the one or more exogenous TCRs comprise a TCRα chain and a TCRβ chain. In some aspects, the one or more exogenous TCRs comprise a TCRγ chain and a TCRδ chain. In some aspects, the chains of the exogenous TCR are encoded for on the same TCR polynucleotide sequence. In some aspects, the one or more TCR polynucleotide sequences are selected from the group consisting of: a viral vector, a cDNA, a plasmid, a linear double-stranded DNA vector, a linear single-stranded DNA vector, and a linear single-stranded RNA vector. In some aspects, the viral vector is integrated into a genome of the one or more antigen-specific TCR expressing cell populations. In some aspects, the one or more exogenous TCRs are identified or have been identified in a tumor sample. In some aspects, the one or more exogenous TCRs are selected based upon frequency in the tumor sample. In some aspects, the one or more exogenous TCRs are selected based upon a phenotype of a cell expressing the one or more exogenous TCRs. In some aspects, the phenotype is selected from the group consisting of: PD-1 positive, CD39 positive, CD137 positive, and combinations thereof.

In some aspects, the one or more antigen-specific TCR expressing cell populations comprise a TCR co-receptor. In some aspects, the TCR co-receptor is selected from the group consisting of: CD3, CD4, CD8, or combinations thereof. In some aspects, the TCR co-receptor is CD3. In some aspects, the TCR co-receptor is an exogenous TCR co-receptor, optionally wherein the one or more antigen-specific TCR expressing cell populations do not express an endogenous TCR co-receptor. In some aspects, the exogenous TCR co-receptor is encoded for by a TCR co-receptor polynucleotide sequence, wherein the co-receptor polynucleotide sequence is operably linked to a promoter nucleotide sequence. In some aspects, the TCR co-receptor polynucleotide sequence is selected from the group consisting of: a viral vector, a cDNA, a plasmid, a linear double-stranded DNA vector, a linear single-stranded DNA vector, and a linear single-stranded RNA vector. In some aspects, the viral vector is integrated into a genome of the one or more antigen-specific TCR expressing cell populations.

In some aspects, the one or more target cell populations comprises an immortalized cell line. In some aspects, the immortalized cell line is a K562 cell line. In some aspects, the one or more target cell populations comprises a professional antigen presenting cell (APC) population. In some aspects, the professional APC population is selected from the group consisting of: a dendritic cell, a macrophage, and a B cell.

In some aspects, at least one of the one or more MHC alleles comprises an exogenous MHC allele, optionally wherein the one or more target cell populations does not express an endogenous MHC allele. In some aspects, the exogenous MHC allele are encoded for by one or more MHC polynucleotide sequences, wherein the one or more MHC polynucleotide sequences are operably linked to a promoter nucleotide sequence. In some aspects, the one or more MHC polynucleotide sequences are selected from the group consisting of: a viral vector, a cDNA, a plasmid, a linear double-stranded DNA vector, a linear single-stranded DNA vector, and a linear single-stranded RNA vector. In some aspects, the viral vector is integrated into a genome of the one or more target cell populations.

In some aspects, at least one of the one or more MHC alleles comprises a mammalian MHC allele. In some aspects, the mammalian MHC allele comprises a human MHC allele.

In some aspects, at least one of the one or more MHC alleles comprises a MHC class I molecule. In some aspects, the MHC class I molecule is selected from the group consisting of: HLA-A, HLA-B, and HLA-C. In some aspects, at least one of the one or more MHC alleles comprises a MHC class II molecule. In some aspects, the MHC class II molecule comprises and MHC molecule selected from the group consisting of: HLA-DQ and HLA-DR.

In some aspects, at least one of the one or more MHC alleles comprises a single chain trimer (SCT).

In some aspects, at least one of the one or more MHC alleles comprises an MHC allele of a subject. In some aspects, the subject is known or suspected to have cancer.

In some aspects, at least one of the one or more antigenic peptides is selected from the group consisting of: a tumor associated epitope, a neoepitope, a tumor neoepitope, a viral epitope, a phospho-epitope, a bacterial epitope, a microbial epitope, a tissue-specific self-epitope, a self-epitope, and combinations thereof. In some aspects, the one or more antigenic peptides comprises a neoepitope. In some aspects, the neoepitope is selected by analyzing tumor, viral, or bacterial sequencing data from a subject to identify one or more somatic mutations. In some aspects, the subject is known or suspected to have cancer. In some aspects, the analyzing is performed using an in silico predictive algorithm. In some aspects, the predictive algorithm comprises an MHC binding algorithm to predict binding between the neoantigen and a MHC allele of the subject In some aspects, at least one of the one or more MHC alleles is the MHC allele of the subject.

In some aspects, each of the one or more antigenic peptides comprises an antigenic peptide derived from a healthy sample.

In some aspects, at least one of the one or more antigenic peptides is presented on an MHC class I molecule. In some aspects, the at least one of the one or more antigenic peptides presented on an MHC class I molecule is 7-15, 7-10, 8-9, 7, 8, 9, 10, 11, 12, 13, 14, or 15 amino acids in length. In some aspects, the at least one of the one or more antigenic peptides presented on an MHC class I molecule is between 8-10 amino acids in length.

In some aspects, at least one of the one or more antigenic peptides is presented on an WIC class II molecule. In some aspects, the at least one of the one or more antigenic peptides presented on an WIC class II molecule is 11-30, 14-20, 15-18, 11, 12, 13, 14, 15, 16, 17, 18, 19, 20, 21, 22, 23, 24, 25, 26, 27, 28, 29, or 30 amino acids in length. In some aspects, the at least one of the one or more antigenic peptides presented on an MHC class II molecule is between 10 and 35, between 10 and 30, between 10 and 25, or between 10 and 20 amino acids in length.

In some aspects, at least one of the one or more antigenic peptides comprises an exogenous antigenic peptide. In some aspects, the exogenous antigenic peptide is encoded for by an antigen polynucleotide sequence, wherein the antigen polynucleotide sequence is operably linked to a promoter nucleotide sequence. In some aspects, the antigen polynucleotide sequence is selected from the group consisting of: a viral vector, a cDNA, a plasmid, a linear double-stranded DNA vector, a linear single-stranded DNA vector, and a linear single-stranded RNA vector. In some aspects, the viral vector is integrated into a genome of the one or more target cell populations.

In some aspects, the at least one of the one or more antigenic peptides is derived from an unprocessed peptide sequence, wherein the unprocessed peptide sequence comprises the at least one of the one or more antigenic peptides. In some aspects, the unprocessed peptide sequence is processed by the target cell to produce the at least one of the one or more antigenic peptides. In some aspects, the unprocessed peptide sequence is targeted to the proteasome. In some aspects, the target cell is engineered to increase processing or stimulated to increase processing. In some aspects, the unprocessed peptide sequence is encoded for by an unprocessed antigen polynucleotide sequence, wherein the unprocessed antigen polynucleotide sequence is operably linked to a promoter nucleotide sequence. In some aspects, the unprocessed antigen polynucleotide sequence is selected from the group consisting of: a viral vector, a cDNA, a plasmid, a linear double-stranded DNA vector, a linear single-stranded DNA vector, and a linear single-stranded RNA vector. In some aspects, the viral vector is integrated into a genome of the one or more target cell populations.

In some aspects, the contacting comprises rotating, inverting, vortexing, shaking, incubating, pipetting, mixing, or combinations thereof. In some aspects, the contacting is performed in a container. In some aspects, the container is selected from the group consisting of: a multi-well plate, a tissue culture treated plate, a tissue culture treated multi-well plate, a flask, a tissue culture treated flask, a microcentrifuge tube, a culture tube, a test tube, a round-bottom tube, and a conical tube.

In some aspects, at least one of the one or more membrane components comprises an antigen-specific TCR expressing cell membrane component. In some aspects, the antigen-specific TCR expressing cell membrane component is selected from the group consisting of: a TCR; a TCR co-receptor, a CD3 TCR co-receptor, a CD4 TCR co-receptor, and a CD8 TCR co-receptor. In some aspects, at least one of the one or more membrane components comprises a target cell membrane component. In some aspects, the target cell membrane component comprises an MHC allele.

In some aspects, at least one of the one or more membrane components comprises an exogenous membrane component. In some aspects, the exogenous membrane component is selected from the group consisting of: a transmembrane protein, a membrane associated protein, a surface receptor, a fluorescent molecule, a cell surface protein, a sugar, and a lipid.

In some aspects, at least one of the one or more membrane components comprises a labeled membrane component. In some aspects, the labeled membrane component comprises a biotin label, a fluorescent label, or a reactive group.

In some aspects, the isolating comprises separating the target cell of interest or the TCR expressing cell of interest comprising the one or more transferred membrane components from a target cell or TCR expressing cell that does not comprise the one or more transferred membrane components.

In some aspects, the isolating comprises magnetic separation. In some aspects, the magnetic separation comprises capturing the target cell of interest or the TCR expressing cell of interest against a wall with a magnet and removing elements not captured against the wall.

In some aspects, the isolating step comprises using a microfluidic device. In some aspects, the microfluidic device comprises a flow cytometer. In some aspects, the isolating step comprises fluorescence-activated cell sorting (FACS).

In some aspects, the isolating comprises identifying the one or more membrane components. In some aspects, the identifying comprises contacting the target cell of interest or the TCR expressing cell of interest with a labeling reagent. In some aspects, the labeling reagent is selected from the group consisting of: an antibody, a reagent comprising a reactive group, and a lipid reactive reagent. In some aspects, the labeling reagent is conjugated to a detectable marker. In some aspects, the detectable marker is a fluorophore.

In some aspects, the determining step (e) comprises purifying or having purified one or more polynucleotides from the target cell of interest or the TCR expressing cell of interest. In some aspects, the purified polynucleotide is selected from the group consisting of: genomic DNA, vector DNA, plasmid DNA, mRNA, DNA amplified by PCR, and cDNA produced by reverse transcription. In some aspects, the purifying or having purified the one or more polynucleotides comprises purifying or having purified the one or more polynucleotides from a single cell.

In some aspects, the determining step (e) comprises sequencing. In some aspects, the sequencing comprises sequencing a polynucleotide. In some aspects, the sequencing comprises sequencing or having sequenced any of the purified polynucleotide described herein, or sequencing or having sequenced any polynucleotide generated using any of the purified polynucleotides described herein as a template.

In some aspects, the sequencing comprises next generation sequencing. In some aspects, the sequencing comprises single cell sequencing.

In some aspects, the determining step further comprises identifying a neoantigen or a neoantigen specific TCR.

In some aspects, the one or more membrane components comprises one or more oligonucleotide barcodes. In some aspects, the one or more oligonucleotide barcodes is directly conjugated to the one or more membrane components. In some aspects, the one or more oligonucleotide barcodes is indirectly conjugated to the one or more membrane components. In some aspects, the one or more oligonucleotide barcodes is conjugated to a labeling reagent. In some aspects, the labeling reagent is selected from the group consisting of: an antibody, a reagent comprising a reactive group, and a lipid reactive reagent. In some aspects, the determining step (e) further comprises determining of or having determined a sequence of at least one of the one or more oligonucleotide barcodes. In some aspects, the sequence of the at least one oligonucleotide barcode is unique to a specific TCR of the one or more antigen-specific TCR expressing cell populations. In some aspects, the one or more antigen-specific TCR expressing cell populations comprises two or more distinct antigen-specific TCR expressing cell populations, each distinct antigen-specific TCR expressing cell population comprising a unique TCR and a unique, defined barcode sequence operably associated with the identity of each unique TCR. In some aspects, the sequence of the at least one oligonucleotide barcode is unique to a specific target cell population of the one or more target cell populations. In some aspects, the specific target cell population expresses a unique antigenic peptide, a unique MHC allele, or a unique antigenic peptide and MHC allele pair. In some aspects, the one or more target cell populations comprises two or more distinct target cell populations, each distinct target cell comprising a unique, defined barcode sequence operably associated with the identity of each unique antigenic peptide, each unique MHC allele, or each unique antigenic peptide and MHC allele pair.

Also disclosed herein is an isolated target cell of interest or TCR expressing cell of interest produced by any of the above methods.

Also disclosed herein is a purified polynucleotide or any polynucleotide generated using the purified polynucleotide as a template produced by any of the above methods.

Also disclosed herein is a database comprising one or more sequences produced by any of the above methods. In some aspects, the one or more sequences comprise one or more sequenced polynucleotides produced by any of the above methods.

Also disclosed herein is an isolated target cell of interest, wherein the target cell comprises: i) one or more T cell membrane associated components, wherein the target cell does not comprise an endogenous polynucleotide sequence encoding the one or more T cell membrane components; and ii) one or more major histocompatibility complex (MHC) alleles, wherein one or more antigenic peptides are presented on the one or more major histocompatibility complex (MHC) alleles. In some aspects, the one or more antigenic peptides are encoded for by one or more antigen polynucleotide sequences.

Also disclosed herein is a method of ligand identification comprising the steps of: a) providing one or more ligand-specific binding molecule expressing cell populations; b) providing one or more target cell populations, wherein the target cell populations present one or more ligands capable of being bound by the one or more ligand-specific binding molecules; c) contacting the one or more ligand-specific binding molecule expressing cell populations with the one or more target cell populations, wherein the contacting comprises providing conditions sufficient for at least one ligand-specific binding molecule expressing cell to specifically bind at least one target cell, and wherein one or more membrane components are transferred between the ligand-specific binding molecule expressing cell and the target cell following binding; d) isolating or having isolated i) a target cell of interest, wherein the target cell of interest comprises the one or more membrane components transferred from the ligand-specific binding molecule expressing cell following the contacting step (c); and optionally ii) a ligand-specific binding molecule expressing cell of interest, wherein the ligand-specific binding molecule expressing cell of interest comprises the one or more membrane components transferred from the target cell following the contacting step (c); and e) determining or having determined, i) at least a portion of a sequence encoding the one or more ligands associated with the target cell of interest, or ii) at least a portion of a binding molecule sequence encoding a binding molecule peptide associated with the binding molecule ligand-specific expressing cell of interest. In some aspects, the ligand-specific binding molecule is selected from the group consisting of: an immunoreceptor, an immunoglobulin, an antibody or fragment thereof, a receptor, a chimeric receptor, a chimeric antigen receptor (CAR), a signaling receptor, a cell-surface receptor, and a transmembrane receptor. In some aspects, the one or more ligands are selected from the group consisting of: an antigen, a surface antigen, an epitope, a non-classical MHC presented antigen, and a receptor ligand.

BRIEF DESCRIPTION OF THE SEVERAL VIEWS OF THE DRAWINGS

These and other features, aspects, and advantages of the invention will become better understood with regard to the following description, and accompanying drawings, where:

FIG. 1A-E. Target cell trogocytosis is antigen-specific. (FIG. 1A) Resolution via flow cytometry of Jurkat and K562 cells. The Jurkat T cells and K562 cells were resolved by gating on the LNGFR$^+$ population and the ZsGreen$^+$ population, respectively. (FIG. 1B) The level of NHS-biotin on the biotinylated F5-Jurkat T cells in the co-incubation with cognate MART1-K562 target cells (ZsGreen$^+$) expressing single-chain trimer (SCT) of HLA-A2/MART1$_{26-35(A27L)}$ or non-cognate NYEOS1-K562 target cells expressing SCT of HLA-A2/NYESO1$_{157-165(C165V)}$. The surface proteins on F5-Jurkat T cells were labeled with 1 mg/ml NHS-biotin and the level of biotinylated protein was assessed using fluorescently-labeled streptavidin. (FIG. 1C) Transfer of biotinylated membrane proteins from Jurkat T cells (LNGFR$^+$) to K562 target cells (ZsGreen$^+$) was assessed using fluorescently-labeled streptavidin, following co-incubation at a 5:1 ratio of Jurkat to K562 cells. (FIG. 1D) Antigen-specific transfer of cell membrane proteins, LNGFR and TCR, from F5-Jurkat T cells to cognate MART1-K562 target cells (ZsGreen$^+$), but not to non-cognate NYESO1-K562 target cells (ZsGreen$^+$) (5:1 J:K). Trogocytosis was assessed using anti-LNGFR and anti-human TCR (huTCR) antibodies. (FIG. 1E) Representative flow cytometry plot overlay of either NYESO1-K562 or MART1-K562 cells following co-incubation with 1G4-Jurkat or F5-Jurkat T cells (5:1 J:K). K562 cells (ZsGreen$^+$HLA-A2$^+$) showed antigen-specific acquisition of T cell membrane proteins, LNGFR and huTCR, and Jurkat cells (ZsGreen$^-$ HLA-A2$^-$) showed antigen-specific loss of membrane proteins LNGFR and huTCR. Relevant populations are indicated.

FIG. 2A-C. Trogocytosis is titratable and augmented by the presence of CD8. (FIG. 2A) Comparison of trogocytosis capability of murinized F5-Jurkat or 1G4-Jurkat cells with HLA-A2 expressing K562 (A2-K562) cells loaded with different doses of MART1 (ELAGIGILTV (SEQ ID NO:3); top) or NYESO1 (SLLMWITQV (SEQ ID NO:2); bottom) heteroclitic peptide ranging from 0 to 10 uM (5:1 J:K). SCT-K562 cells (eGFP$^+$) were assessed for acquisition of TCR using an anti-muTCR antibody. For each condition, left column represents F5-Jurkat cells and right column represents 1G4-Jurkat cells. (FIG. 2B) Comparison of trogocytosis capability of murinized F5-Jurkat or 1G4-Jurkat cells with A2-K562 cells loaded with different MART1 (top) or NYESO1 (bottom) variants (5:1 J:K). Trogocytosis capability was assessed by the percentage of TCR$^+$eGFP$^+$ A2-K562 cells. For each condition, left column represents F5-Jurkat cells and right column represents 1G4-Jurkat cells. (FIG. 2C) Comparison of trogocytosis capability of CD8$^+$ or CD8$^-$ F5-Jurkat or 1G4-Jurkat cells with MART1-K562 or NYESO1-K562 cells as shown by the percentage of TCR$^+$ eGFP$^+$ SCT-K562 (5:1 J:K). For each condition, columns from left to right represent F5-Jurkat cells, F5-CD8-Jurkat cells, 1G4-Jurkat cells, and 1G4-CD8$^-$ Jurkat cells.

(FIG. 3A) Schematic and representative flow plots for 1:10,000 cognate NYESO1-K562 (CD80$^-$ZsGreen$^+$) target cells to non-cognate A2-K562 cells (CD80$^+$ZsGreen$^-$) co-incubated with either F5-Jurkat (top) or 1G4-Jurkat (bottom) cells (20,000: 10,000:1 Jurkat:K562:SCT-K562). NYESO1-K562 cells (HLA-A2$^+$ZsGreen$^+$) and non-cognate A2-K562 cells (HLA-A2$^+$ZsGreen$^-$) were gated separately to analyze acquisition of membrane transfer markers, LNGFR and TCR, using anti-LNGFR and anti-muTCR antibodies. An overlay of the non-cognate A2-K562 cells (gray) provides a clear comparison of trogocytosis in cognate versus non-cognate K562 cells. (FIG. 3B) Schematic and flow cytometry plots for 1:10,000 cognate MART1-K562 (CD80$^-$Zs-Green$^+$) target cells to non-cognate A2-K562 cells (CD80$^+$ ZsGreen$^-$) co-incubated with either 1G4-Jurkat (top) or F5-Jurkat (bottom) cells. The flow cytometry data for this experiment was analyzed analogously to those in (a).

FIG. 4A-D. Target cell trogocytosis validates ligands for public F5- and 1G4 TCR. (FIG. 4a) Schematic outline of trogocytosis used in the context of an A2-restricted library containing 12,055 epitopes. An A2-restricted SCT DNA library containing various known T cell epitopes from Immune Epitope Database (IEDB) was first generated. Next, K562 cells were transduced with the A2-restricted SCT library at a low MOI to ensure each cell contained only one or two copies of DNA. F5-Jurkat or 1G4 Jurkat cells (E2-Crimson$^+$ CD8$^+$) were then co-incubated with K562 library cells (2:1 J:K) and trogocytosis$^+$ (E2-Crimson$^-$eGFP$^+$TCR$^+$) A2-SCT-K562 cells were sorted using FACS for antigen validation by dextramer staining, co-incubation, and next generation sequencing (NGS). (FIG. 4B) Histograms representing the mean fluorescence of sorted trogocytosis$^+$ SCT-K562 cells following a validating co-incubation of K562 sorted cells from a F5-Jurkat culture (left panel) or K562 sorted cells from a 1G4-Jurkat culture (left panel) incubated with F5-Jurkat or 1G4-Jurkat (2:1 J:K). (FIG. 4C) Representative flow cytometry plots of 1G4 TCR or F5 TCR dextramer binding by sorted trogocytosis$^+$ SCT-K562 cells. The trogocytosis$^+$ SCT-K562 after one or two rounds of co-incubation with F5-Jurkat or 1G4-Jurkat cells and selection by FACS were validated via fluorescently labeled F5 TCR (top) and 1G4 TCR (bottom) dextramer staining. (FIG. 4D) Validation of enriched peptides after two rounds of trogocytosis selection by deep-sequencing analysis. Rank average represents the ranking of enriched peptides, calculated based on the abundance of each peptide among all peptides, from experimental triplicates.

FIG. 5A-D. Target cell trogocytosis identifies the cognate ligand for a neoantigen-specific, patient-derived TCR. (FIG. 5A) Schematic outline trogocytosis used in the context of an A2-restricted neoepitope library derived from a tumor sample containing 5,000 epitopes. An A2-restricted neoantigen SCT library was first generated using the predicted neoeitopes presented by HLA-A*02:01 from mutated sequences identified via exome sequencing of melanoma from a patient. Next, CD8$^+$ Jurkat cells (E2-Crimson$^+$) were transduced with a neoepitope-specific TCR (neoTCR) from the same patient and K562 cells were transduced with the A2-restricted neoepitope library at a low MOI to ensure each cell contained only one or two copies of DNA. These cells were then co-incubated (2:1 J:K) and trogocytosis$^+$ (eGFP$^+$ TCR$^+$) A2-restricted SCT-K562 cells were sorted using FACS for epitope identification by NGS and validation by co-incubation and cytoxicity assays. (FIG. 5B) Identification of enriched peptides after two rounds of trogocytosis selection by deep-sequencing analysis. Rank average represents the ranking of enriched peptides, calculated based on the abundance of each peptide among all peptides, from experimental triplicates. (FIG. 5C) Histograms showing validation of TCR-neoantigen pairing via a trogocytosis test by assessing neoepitope-specific TCR transfer from neoTCR-Jurkat cells to with USP7mut-K562 cells (2:1 J:K) (left panel). Histograms were quantified as a percentage of TCR positive cells (right panel). For each condition, left column represents F5-Jurkat cells and right column represents neo12-Jurkat cells. (FIG. 5D) Cytotoxicity of neoTCR-T cells against USP7mut-K562 cells in vitro. NeoTCR-T cells or F5TCR-T cells were co-incubated for 4 hr with USP7mut-K562 or MART1-K562 cells at different effector-to-target ratios and cytotoxicity against USP7mut-K562 or MART1-K562 cells was measured and presented as % specific lysis.

(FIG. 6A) A retroviral vector co-delivered F5 TCR or 1G4 TCR genes carrying either human or murine TCR constant regions together with LNGFRΔ, a transduction marker comprising low-affinity nerve growth factor receptor with the intracellular domain truncated, to Jurkat cells. A lentiviral vector co-delivered an SCT containing MART1 or NYESO1 peptide with ZsGreen as a transduction marker to K562 cells. SCTs are composed of a single polypeptide chain with a linear composition of antigenic peptide, β2-microglobulin, and HLA-A2 domains via flexible GS linkers. (FIG. 6B) Red/blue coloring indicates cognate TCR-antigen pairs. F5 TCR (red) is paired with the SCT expressing MART1 peptide and 1G4 TCR (blue) is paired with the SCT expressing NYESO1 peptide.

(FIG. 7A) Antigen-specific transfer of the T cell membrane proteins, CD3 and CD8, from CD8-expressing F5-Jurkat and 1G4-Jurkat cells to K562 cells (ZsGreen$^+$), as assessed by anti-CD3 and anti-CD8 antibodies (5:1 J:K). (FIG. 7B) Antigen-specific transfer of the K562 cell membrane protein, HLA-A2, from K562 cells to Jurkat cells (ZsGreen), as assessed by an anti-HLA-A2 antibody (5:1 J:K). (FIG. 7C and FIG. 7D) Concomitant reduction of membrane proteins from donor cells. K562 cells (ZsGreen$^+$) showed an antigen-specific loss of HLA-A2 while Jurkat cells (ZsGreen$^-$) showed an antigen-specific loss of LNGFR and murinized TCR, as assessed by an anti-HLA-A2, anti-LNGFR, and anti-mouse TCR (muTCR) antibodies FIG. 8. Antigen-specific TCR transfer occurs from donor cells to acceptor cells regardless of cell identity.

FIG. 9A-J. Histographic visualization of trogocytosis capability based on peptide dosing and variants. (FIG. 9A) Comparison of trogocytosis capability of murinized F5-Jurkat cells with A2-K562 cells loaded with different doses of cognate MART1 heteroclitic peptide ranging from 0 to 10 uM (5:1 J:K). Trogocytosis was determined by the percentage of eGFP$^+$TCR$^+$ A2-K562 cells. (FIG. 9B) Comparison of trogocytosis capability of murinized F5-Jurkat cells with A2-K562 cells loaded with different doses of non-cognate NYESO1 ranging from 0 to 10 uM (5:1 J:K) as assessed by the percentage of eGFP$^+$TCR$^+$ A2-K562 cells. (FIG. 9C) Comparison of trogocytosis capability of murinized 1G4-Jurkat cells with A2-K562 cells loaded with different doses of cognate NYESO1 ranging from 0 to 10 uM (5:1 J:K) as assessed by the percentage of eGFP$^+$TCR$^+$ K562 cells. (FIG. 9D) Comparison of trogocytosis capability of murinized 1G4-Jurkat cells with A2-K562 cells loaded with different doses of MART1 ranging from 0 to 10 uM (5:1 J:K) as assessed by the percentage of eGFP$^+$TCR$^+$ K562 cells. (FIG. 9E) Comparison of trogocytosis capability of murinized F5-Jurkat cells with A2-K562 cells loaded with different MART1 variants determined by the percentage of eGFP$^+$ TCR$^+$ A2-K562 cells (5:1 J:K). (FIG. 9F) Comparison of trogocytosis capability of murinized 1G4-Jurkat cells with A2-K562 cells loaded with different MART1 variants determined by the percentage of eGFP$^+$TCR$^+$ A2-K562 cells (5:1 J:K). (FIG. 9G) Comparison of trogocytosis capability of murinized 1G4-Jurkat cells with A2-K562 cells loaded with different NYESO1 variants determined by the percentage of eGFP$^+$TCR$^+$ A2-K562 cells (5:1 J:K). (FIG. 9H) Comparison of trogocytosis capability of murinized F5-Jurkat cells with A2-K562 cells loaded with different NYESO1 variants determined by the percentage of eGFP$^+$TCR$^+$ A2-K562 cells (5:1 J:K). (FIG. 9I) Comparison of trogocytosis capability of CD8$^+$ or CD8$^-$ murinized F5-Jurkat cells with MART1-K562 or NYESO1-K562 cells determined by the percentage of eGFP$^+$TCR$^+$ SCT-K562 cells (5:1 J:K). (FIG. 9J) Comparison of trogocytosis capability of CD8$^+$ or CD8$^-$ murinized 1G4-Jurkat cells with MART1-K562 or NYESO1-K562 cells determined by the percentage of eGFP⁺TCR⁺ SCT-K562 cells (5:1 J:K).

FIG. 10A-C. Target cell trogocytosis resolves cognate antigen-expressing target cells from non-cognate antigen-expressing cells. (FIG. 10A) Schematic of experiment. A 1:1 mixture of NYESO1-K562 and MART1-K562 was used in co-incubation experiments with F5-Jurkat or 1G4-Jurkat cells (10:1:1 Jurkat:NYESO1-K562:MART1-K562). Trogocytosis⁺ SCT-K562 cells (HLA-A2⁺ZsGreen⁺LNGFR$^{high}$TCR$^{high}$) cells were further analyzed by dextramer staining to verify antigen-specific trogocytosis. (FIG. 10B) Representative flow plots for a 1:1 mixture of NYESO1-K562 and MART1-K562 cells co-incubated with either 1G4-Jurkat (top) or F5-Jurkat (bottom) cells (10:1:1 Jurkat: NYESO1-K562:MART1-K562). Mixed NYESO1-K562 and MART1-K562 cells (HLA-A2⁺ZsGreen⁺) were separately gated for trogocytosis⁺ (TCR⁺LNGFR⁺) and trogocytosis⁻ (TCR⁻LNGFR⁻) populations. The trogocytosis⁺ and trogocytosis⁻ populations were then verified for antigen-specificity by using either F5 TCR or 1G4 TCR dextramer staining. (FIG. 10C) Quantification of triplicate 1:1 K562 mixture experiments verifying that trogocytosis can specifically resolve cognate antigen-expressing target cells. Trogocytosis⁺ NYESO1-K562 cells stained positively for cognate 1G4 TCR dextramer. For each gating condition, left column represents 1G4-Jurkat cells and right column represents F5-Jurkat cells.

DETAILED DESCRIPTION

Figure 1B:
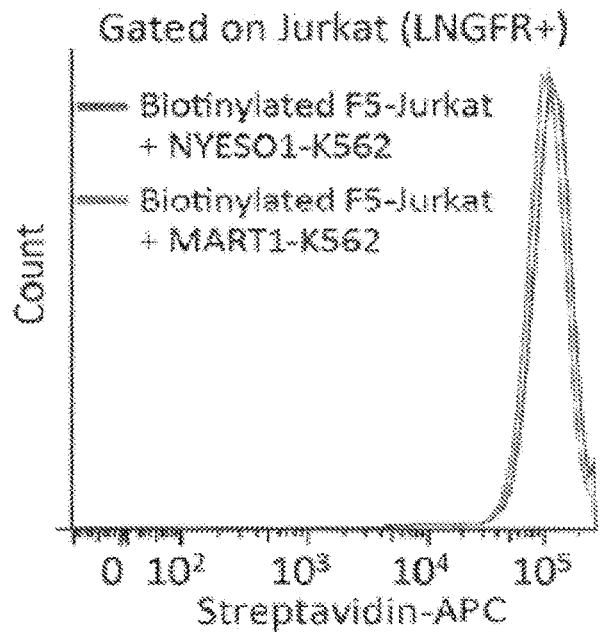

The details of various embodiments of the invention are set forth in the description below. Other features, objects, and advantages of the invention will be apparent from the description and the drawings, and from the claims.

Definitions

Terms used in the claims and specification are defined as set forth below unless otherwise specified.

As used herein, "antigen-specific T cells" or "antigen-specific TCR expressing" cells refer to cells that are distinguished from one another by their T cell receptors (TCRs), which give them their antigen specificity for a cognate antigenic peptide (also referred to as an "epitope") presented by an WIC.

Embodiments of the invention include a recombinant antigen-MHC complex that is capable of pairing with cognate T cells. As used herein, "antigen-MHC," "antigen-MHC complex," "recombinant antigen-MHC complex," "peptide MHC," and "p/MHC," are used interchangeably to refer to a major histocompatibility complex with a peptide in the antigen binding groove of MHC.

As used herein, "antigen" includes any antigen including patient-specific neoantigens. "Antigenic peptide" refers to a peptide fragment capable of binding an MHC molecule and being presented to TCR expressing cells. "Neoantigen" refers to an antigen that has at least one alteration that makes the neoantigen or presentation of the neoantigen distinct from its corresponding wild-type antigen, e.g., mutations in the polypeptide sequence, differences is post-translation modifications, or differences in expression level. "Tumor neoantigens" refer to neoantigens that are derived from a tumor or a cancer, e.g., from the tumor of a patient."

As used herein, "T cell paired antigen MHC complex" refers to the complex of a T cell having a T cell receptor that binds to an antigen peptide presented by an MHC molecule.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

It must be noted that, as used in the specification and the appended claims, the singular forms "a," "an" and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

INTRODUCTION

T-cell mediated immunity can be characterized by the activation of antigen-specific cytotoxic T cells that are able to induce death in cells that display antigen in a major histocompatibility complex (MHC) on their surface. These cells displaying an MHC complex loaded with antigen include virus-infected cells, cells with intracellular bacteria, cells that have internalized or phagocytosed extracellular sources of protein, and cancer cells displaying tumor antigens.

To utilize the T-cell mediated immunity process, e.g., for patient-specific cancer immunotherapy, one of the initial steps can include identification of the patient's tumor-specific antigens (e.g., neoantigens). Contrary to published literature, antigen-presenting target cells can extract membrane and membrane-associated proteins from interacting T cells through a process designated herein as target cell trogocytosis. Antigen-specific target cell trogocytosis can be tracked by multiple-protein transfer and by loss of proteins from donor cells. Such target cell trogocytosis is peptide MHC-density-dependent and is able to distinguish different peptide variants based on the respective recognition ability of the TCR for each variant.

Described herein is a TCR ligand discovery platform that exploits the target cell trogocytosis phenomenon to selectively mark target cells, such as MHC allele expressing cells, that present epitopes cognate to orphan TCR-transduced cells, such as T cells, enabling isolation of the recognized epitopes from a target cell library. Also described herein is a TCR discovery platform that exploits the target cell trogocytosis phenomenon to selectively mark orphan TCR-transduced cells, such as T cells, that recognize cognate epitopes on target cells enabling isolation of the TCR from a TCR expressing cell library.

Also described herein is a ligand discovery platform that exploits target cell trogocytosis phenomenon to selectively mark and identify ligands and their cognate binding molecules.

Method of Antigen Identification

Provided herein is a method of antigen identification comprising the steps of: a) providing one or more antigen-specific T cell receptor (TCR) expressing cell populations;

b) providing one or more target cell populations, wherein the target cell populations present one or more antigenic peptides on one or more major histocompatibility complex (MHC) alleles; c) contacting the one or more antigen-specific TCR expressing cell populations with the one or more target cell populations, wherein the contacting comprises providing conditions sufficient for at least one of the one or more antigen-specific TCR expressing cell populations to specifically bind at least one of the one or more target cell populations, and wherein one or more membrane components are transferred between the at least one antigen-specific TCR expressing cell and the at least one target cell following binding; d) isolating or having isolated i) a target cell of interest, wherein the target cell of interest comprises the one or more membrane components transferred from the at least one antigen-specific TCR expressing cell following the contacting step (c), and optionally ii) a TCR expressing cell of interest, wherein the TCR expressing cell of interest comprises the one or more membrane components transferred from the at least one target cell following the contacting step (c); and e) determining or having determined i) a sequence of one or more antigenic peptides associated with the target cell of interest, ii) at least a portion of a TCR sequence encoding a TCR peptide associated with the TCR expressing cell of interest, or iii) a sequence of one or more antigenic peptides associated with the target cell of interest and at least a portion of a TCR sequence encoding a TCR peptide associated with the TCR expressing cell of interest.

Antigen-Specific TCR Expressing Cells

Antigen-specific TCR expressing cells refer to any cell expressing one or more TCRs.

As used herein, "population" refers to a group of clonally identical, or substantially identical, cells. A population can refer to any number of clonally identical cells. For example, a population can refer to one cell, greater than one cell, 2 cells, 3 cells, 4 cells, 5 cells, 6 cells, 7 cells, 8 cells, 9 cells, 10 cells, greater than 10 cells, greater than 20 cells, greater than 30 cells, greater than 40 cells, greater than 50 cells, greater than $10^2$ cells, greater than $10^3$ cells, greater than $10^4$ cells, greater than $10^5$ cells, greater than $10^6$ cells, greater than $10^7$ cells, or greater than $10^8$ cells. One or more antigen-specific TCR expressing cell populations can be 2, 3, 4, 5, 6, 7, 8, 9, 10 or more antigen-specific TCR expressing cell populations. One or more antigen-specific TCR expressing cell populations can be greater than 10, greater than 20, greater than 30, greater than 40, greater than 50, greater than $10^2$, greater than $10^3$, greater than $10^4$, greater than $10^5$, greater than $10^6$, greater than $10^7$, or greater than $10^8$ antigen-specific TCR expressing cell populations. One or more target cell populations can be 2, 3, 4, 5, 6, 7, 8, 9, 10 or more target cell populations. One or more target cell populations can be greater than 10, greater than 20, greater than 30, greater than 40, greater than 50, greater than $10^2$, greater than $10^3$, greater than $10^4$, greater than $10^5$, greater than $10^6$, greater than $10^7$, or greater than $10^8$ target cell populations.

An antigen-specific TCR expressing cell can be a T cell. Examples of T cells include, but are not limited to, a cytotoxic T cell (CTL), a CD8+ T cell, a CD4+ T cell, a primary T cell, an ex vivo cultured T cell, a tumor infiltrating T cell, an autoimmune T cell, a pathogen-specific T cell, a regulatory T cell, an exhausted T cell, a memory T cell population, a Natural Killer T cell (NKT) population, a gamma-delta (γδ) T cell population, an engineered T cell, and an immortalized T cell line. A particular example of a T cell useful for the methods herein include a Jurkat immortalized T cell line (also referred to as "Jurkats" or "Jurkat cells"). Jurkat cells are able to be engineered, such as to express exogenous proteins (e.g., exogenous TCRs) and/or to delete particular genes of interest, and are able to be passaged to generate clones or libraries useful for the methods herein. Various Jurkat cell lines with different desired properties have been engineered and are publically available, for example at the American Type Culture Collection. A T cell can be engineered to have properties that facilitate the methods described herein. For example, a T cell can be engineered to not express a specific gene, such as an endogenous TCR molecule, or a T cell can be engineered to express exogenous molecules, such as TCRs or various T cell co-receptors. Methods of cell engineering include, but are not limited to, transient transfection, stable transfection, viral transduction (e.g., retroviral or lentiviral transduction), nuclease-based engineering approaches, electroporation, and other methods of engineering that result in engineered cells, such as T cells (e.g., engineering of animals or stem cells that can be used to produce engineered T cells). Nuclease-based approaches include using a nuclease including, but not limited to, a Clustered Regularly Interspaced Short Palindromic Repeats (CRISPR) family nuclease (e.g., Cas9), a Transcription activator-like effector nuclease (TALEN) or derivative thereof, a zinc-finger nuclease (ZFN) or derivative thereof, and a homing endonuclease (HE) or derivative thereof. A T cell can express only its endogenous TCR expressed from the native TCR locus.

T cells can be isolated from a subject, such as a subject known or suspected to have cancer. Subject-derived (also referred to as "patient-derived") T cells can be isolated from a patient's peripheral blood mononuclear cells (PBMCs) or tumor infiltrating lymphocytes (TILs). For example, both CD4+ and CD8+ T cells can labeled and sorted from PBMCs or TILS using anti-CD4 and anti-CD8 fluorescent antibodies with live populations of CD4+ and CD8+ single-positive cells sorted using fluorescence-activated cell sorting (FACS), to isolate only CD4+ or CD8+ cells. Other sorting methods, such as magnetic sorting, can be used. Subject-derived T cells can also be isolated indirectly from a patient, such as isolating T cells following ex vivo culturing of T cells or T cell precursors isolated from a patient. Various markers can be used to identify and isolate T cells. Markers can be used to isolate T cells more broadly, such as using an anti-CD3 fluorescent antibody followed by FACS to isolate, in general, all T cells. Other markers can be used to isolate particular types or subtypes of T cells. For example, phenotypic markers can be used to distinguish and isolate types or subtypes of T cells, such as activation markers including, but not limited, PD-1, CD39, and CD137. A single marker can used or a combination of different markers can be used (e.g., CD4/PD-1 double positive T cells). A person skilled in the art is able to determine the T cell type or subtype to isolate that are useful for interrogating a type or types of antigenic peptides of interest.

An antigen-specific TCR expressing cell can be also be a cell that is not derived from a T cell. For example, cells not derived T cells include immortalized cell lines that are engineered to express an exogenous TCR. Immortalized cells lines useful for the methods described herein include, but are not limited to, K562 cells, HEK293 cells and its derivatives, 3T3 cells and its derivatives, Chinese Hamster Ovary (CHO) cells and its derivatives, a HeLa cells and its derivatives. Immortalized cells can be engineered as described above.

An antigen-specific TCR expressing cell can be a human or human derived cell, a mammalian or mammalian derived cell, a murine or murine derived cell, or vertebrate or vertebrate derived cell. Other cells and cell expressing systems, such as phage, yeast, and *E. coli* expression systems, can be used. An antigen-specific TCR expressing cell can express proteins derived from a species different than that of the cell, such as a human cell engineered to express a murine derived TCR or vice versa.

An antigen-specific TCR expressing cell can be engineered to express an exogenous TCR. An antigen-specific TCR expressing cell can express an exogenous TCR in addition to or in place of an endogenous TCR, e.g., a T cell expressing an endogenous TCR can be engineered to also express an exogenous TCR. An exogenous TCR can be encoded for by a TCR polynucleotide sequences, wherein the one or more TCR polynucleotide sequences are operably linked to a promoter nucleotide sequence. Polynucleotides that can encode TCRs include, but are not limited to, a viral vector, a cDNA, a plasmid, a linear double-stranded DNA vector, a linear single-stranded DNA vector, and a linear single-stranded RNA vector. Examples of promoter nucleotide sequences include, but are not limited to, mammalian promoters, human promoters, viral promoters, long-terminal repeat (LTR) derived promoters from a retrovirus or lentivirus, fusions of two or more promoters, fusions of two or more portions of promoters, MMLV LTR promoters, HIV LTR promoters, MCMV LTR promoters, EF1α, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems. Polynucleotides that can encode exogenous TCRs can have universal primer sequences useful for PCR mediated amplification of the exogenous TCR and/or attaching sequencing adaptors useful for NGS, e.g. the universal primer sequences can flank the TCR encoding polynucleotide.

A TCR can be transiently expressed from a TCR polynucleotide sequence, where the TCR polynucleotide sequence does not integrate into a genome of an engineered cell. A TCR can be expressed from a TCR polynucleotide sequence that is integrated into the genome of an engineered cell. Integrated TCR polynucleotide sequences can be integrated into a defined locus. Examples of defined genomic loci that can be integrated into include, but are not limited to, a coding region, an intron, a T cell receptor (TCR)-alpha locus, a TCR-beta locus, an immune checkpoint locus (e.g., PD-1, CTLA-4, BTLA, TIM3, LAG3, and VISTA). TCR polynucleotide sequences integrated into a defined locus can be operably linked to and expressed from an endogenous promoter nucleotide sequence of the defined locus, or it can be operably linked to and expressed from an exogenous promoter, such as those described above.

An antigen-specific TCR expressing cell can express a single TCR. An antigen-specific TCR expressing cell can express more than one TCR, for example an antigen-specific TCR expressing cell can express multiple TCRs where each TCR is specific for a different unique antigen. An antigen-specific TCR expressing cell can express 2, 3, 4, 5, 6, 7, 8, 9, 10 or more TCRs. The multiple TCRs can be random, such as multiple TCRs from a TCR expression library, or the multiple TCRs can be rationally selected, for example TCRs known to be present in a subject or patient.

An antigen-specific TCR expressing cell can be present in a population of antigen-specific TCR expressing cells with members of the population expressing different TCRs or combinations of TCRs. In one example, T cells isolated from a subject or patient will generally include a population of antigen-specific TCR expressing cells with members of the population expressing different TCRs. The different TCRs in the population can be random, such as multiple TCRs from a TCR expression library. The different TCRs in the population can be rationally selected. Criteria for rational selection include, but is not limited, selecting TCRs known to be present in a subject or patient, selecting TCRs known to be present at a certain frequency in a subject or patient, and selecting TCRs known to be expressed by a particular T cell population (e.g., any of the T cell populations previously described herein) or T cells characterized by a particular phenotype, for example activated T cells (e.g., characterized as PD-1+, CD39+, and/or CD137+) or exhausted T cells. Methods of identifying potential TCR sequences of interest within a population are known in the art, for example Issued U.S. Pat. No. 8,507,205, Issued U.S. Pat. No. 9,347,099, Issued U.S. Pat. No. 9,506,119, International Application WO2018075693, Han et al. 2014, Briggs et al. 2017, Gros et al. 2014, Pricket et al. 2016, Linneman et al. 2014, Pasetto et al. 2014, and International Application PCT/US18/21611, each of which is incorporated by reference for all purposes.

In general, a TCR is a heterodimeric protein formed by the interaction of two components termed "chains." Classical T cells are generally considered to be alpha-beta (αβ)T cells that express an alpha (α) chain and a beta (β) chain. In its native context, a TCRα chain and a TCRβ chain are expressed from different genes. When an exogenous TCR is expressed, it can be encoded for by two TCR polynucleotide sequences separately encoding a TCRα chain and a TCRβ chain, or it can be encoded for by a single TCR polynucleotide sequence encoding both a TCRα chain and a TCRβ chain. A TCRα chain and a TCRβ chain encoded by a single TCR polynucleotide sequence can be separated by a linker sequence, for example in a TCR-alpha: linker: TCR-beta orientation or a TCR-beta: linker: TCR-alpha orientation. In one series of examples, the linker sequence encodes a cleavable peptide, such as a furin cleavage site, such that the expressed linked TCRα and TCRβ polypeptide can be processed to form separate TCRα and TCRβ polypeptides. In another series of examples, the linker sequence encodes a nucleotide sequence that allows for multicistronic expression, that is separate translation of the TCRα open reading frame and TCRβ open reading frame resulting in separate TCRα and TCRβ polypeptides, such as an IRES element or ribosome skipping elements (e.g., T2A, E2A, P2A, F2A, or other "self-cleaving" peptides).

Other TCRs include those from gamma-delta (γδ) T cells that express a gamma (γ) chain and a delta (δ) chain. Still other TCRs include those from Natural Killer T cells (NKT).

An antigen-specific TCR expressing cell can be engineered to express a marker(s) to identify and/or isolate a correctly engineered antigen-specific TCR expressing cell, such as a fluorescent marker (e.g., eGFP, E2-Crimson), a drug selection marker (e.g., hygromycin, neomycin), or a surface expressed marker (e.g., LNGFR). The methods and systems for engineering expression of a TCR and expression of a marker can be the same or different. A marker polynucleotide sequence can be the same polynucleotide as a TCR polynucleotide sequence, such as the cleavable peptide or multicistronic systems described above. A marker polynucleotide sequence can be a separate polynucleotide from a TCR polynucleotide sequence.

TCR Co-Receptors

An antigen-specific TCR expressing cell can express a T cell co-receptor, such as the T cell co-receptors CD3, CD4, CD8, or combinations thereof. Any co-receptor known to those skilled in the art can be used.

CD3 can associate with a TCR to form a TCR complex. CD3 refers collectively to a complex of proteins comprising CD3δ, CD3ε, CD3γ subunits, and in some contexts, such as an active signaling TCR complex, a CD3ζ subunit.

Like CD3, CD4 and CD8 can associate with a TCR to form a TCR complex. In a native T cell context, a T cell will generally express either CD4 or CD8. Without wishing to be bound by theory, expression of CD4 or CD8 facilitates an antigen-specific TCR expressing cell discriminating between MHC class II or MHC class I expressing cells, respectively, through specific interactions between CD4 and MHC class II or CD8 and MHC class I. T cells that express CD4 (also referred to as "CD4+ T cells", "helper T cells", "T helper cells", or "$T_H$ cells") in general interact with professional antigen presenting cells that express MHC class II. T cells that express CD8 (also referred to as "CD8+ T cells", "cytotoxic T cells", "killer T cells", "Tc cells", or "cytotoxic T lymphocytes (CTLs)") in general interact with any nucleated cell that expresses MHC class I.

In some examples, the methods described herein can be used to discriminate TCR recognition of MHC presented antigenic peptides that require T cell co-receptor expression from those that do not require T cell co-receptor expression.

An antigen-specific TCR expressing cell can express an endogenous T cell co-receptor, such as a T cell. An antigen-specific TCR expressing cell can be engineered to express an exogenous T cell co-receptor. An antigen-specific TCR expressing cell can express an exogenous T cell co-receptor in addition to or in place of an endogenous T cell co-receptor, e.g., a T cell expressing an endogenous T cell co-receptor can be engineered to also express an exogenous T cell co-receptor. An exogenous T cell co-receptor can be encoded for by a T cell co-receptor polynucleotide sequences, wherein the one or more T cell co-receptor polynucleotide sequences are operably linked to a promoter nucleotide sequence. Polynucleotides that can encode T cell co-receptors include, but are not limited to, a viral vector, a cDNA, a plasmid, a linear double-stranded DNA vector, a linear single-stranded DNA vector, and a linear single-stranded RNA vector. Examples of promoter nucleotide sequences include, but are not limited to, mammalian promoters, human promoters, viral promoters, long-terminal repeat (LTR) derived promoters from a retrovirus or lentivirus, fusions of two or more promoters, fusions of two or more portions of promoters, MMLV LTR promoters, HIV LTR promoters, MCMV LTR promoters, EF1α, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems. Polynucleotides that can encode T cell co-receptors can have universal primer sequences useful for PCR mediated amplification of the T cell co-receptor and/or attaching sequencing adaptors useful for NGS, e.g. the universal primer sequences can flank the T cell co-receptor encoding polynucleotide.

A T cell co-receptor can be transiently expressed from a T cell co-receptor polynucleotide sequence, where the T cell co-receptor polynucleotide sequence does not integrate into a genome of an engineered cell. A T cell co-receptor can be expressed from a T cell co-receptor polynucleotide sequence that is integrated into the genome of an engineered cell. Integrated T cell co-receptor polynucleotide sequences can be integrated in defined locus. T cell co-receptor polynucleotide sequences integrated into a defined locus can be operably linked to and expressed from an endogenous promoter nucleotide sequence of the defined locus, or it can be operably linked to and expressed from an exogenous promoter, such as those described above.

An antigen-specific TCR expressing cell engineered to express a T cell co-receptor can be any cell capable of being engineered. An antigen-specific TCR expressing cell engineered to express a T cell co-receptor can also be engineered to express an exogenous TCR. The methods and systems for engineering expression of a TCR and expression of a T cell co-receptor can be the same or different. A T cell co-receptor polynucleotide sequence can be the same polynucleotide as a TCR polynucleotide sequence, such as the cleavable peptide or multicistronic systems described above. A T cell co-receptor polynucleotide sequence can be a separate polynucleotide from a TCR polynucleotide sequence.

Target Cells

As used herein, a "target cell" refers to any cell capable of recognition by an antigen-specific TCR expressing cell or a binding molecule expressing cell. A target cell can be a primary cell, an ex vivo cultured cell, a tumor infiltrating cell, an autoimmune cell, a pathogen-infected cell, a cancer or tumor derived cell, and an immortalized cell line. Immortalized cells lines useful for the methods described herein include, but are not limited to, K562 cells, HEK293 cells and its derivatives (e.g. HEK293T cells), 3T3 cells and its derivatives, Chinese Hamster Ovary (CHO) cells and its derivatives, a HeLa cells and its derivatives. Immortalized cells can be engineered as described above.

A target cell can be a human or human derived cell, a mammalian or mammalian derived cell, a murine or murine derived cell, or vertebrate or vertebrate derived cell. Other cells and cell expressing systems, such as phage, yeast, and E. coli expression systems, can be used. A target cell can express proteins derived from a species different than that of the cell, such as a human cell engineered to express a murine derived protein or vice versa.

MHC Alleles

In examples directed to identifying TCR epitopes, a target call can be any cell expressing an epitope and an MHC molecule (i.e., an MHC allele) capable of presenting the epitope. A target cell engineered to express an MHC can be any cell capable of being engineered.

A target cell can be a cell presenting an epitope, either endogenous or exogenous, on an endogenous MHC molecule to the target cell (i.e., natively expressed by a target cell). Cells expressing endogenous MHC class I molecules in general include all nucleated cells. Cells expressing endogenous MHC class II molecules include professional antigen presenting cells (APCs), such as dendritic cells, macrophages, and B cells.

In general, MHC class I molecules are heterodimeric complexes that comprise a β2-microglobulin (also referred to as β2M, beta-2 microglobulin, or B2M), and an MHC class I heavy chain (also referred to an alpha-chain) comprising an α1, α2, and α3 domain. In their native context, β2M and the MHC class I heavy chain are encoded by different genes and expressed as separate polypeptides.

In general, MHC class II molecules are heterodimeric complexes that comprise an alpha-chain (α-chain) and a beta-chain (β-chain). The alpha-chain contains an α1 domain and an α2 domain, while the beta-chain contains an β1 domain and an β2 domain. In their native context, the alpha-chain and beta-chain are encoded by different genes and expressed as separate polypeptides.

MHC molecules can be mammalian MHC alleles, including, but not limited to, human MHC alleles (also referred to as HLAs). Class I HLAs commonly found in the human population include, but are not limited to, HLA-A, HLA-B, and HLA-C alleles. Specific subclasses of class I HLAs commonly found in the human population include, but are not limited to, HLA-A*02, 24, 01; HLA-B*35, 44, 51; DRB1*11, 13, 07 in caucasians, HLA-A*02, 03, 30; HLA-B*35, 15, 44; DRB1*13, 11, 03 in afro-brazilians, and HLA-A*24, 02, 26; HLA-B*40, 51, 52; DRB1*04, 15, 09 in Asians. Class II HLAs commonly found in the human population include, but are not limited to, HLA-DQ and HLA-DR. Common alleles found in the human population are further described in Bardi et al. (Rev Bras Hematol Hemoter. 2012; 34(1): 25-30.)

A target cell can be engineered to express an exogenous MHC molecule. A target cell can express an MHC molecule in addition to or in place of an endogenous MHC molecule, e.g., an APC expressing an endogenous MHC class II molecule can be engineered to also express an exogenous MHC class II molecule. An exogenous MHC molecule can be encoded for by one or more MHC polynucleotide sequences, wherein the one or more MHC polynucleotide sequences are operably linked to a promoter nucleotide sequence. Polynucleotides that can encode MHC molecules include, but are not limited to, a viral vector, a cDNA, a plasmid, a linear double-stranded DNA vector, a linear single-stranded DNA vector, and a linear single-stranded RNA vector. Examples of promoter nucleotide sequences include, but are not limited to, mammalian promoters, human promoters, viral promoters, long-terminal repeat (LTR) derived promoters from a retrovirus or lentivirus, fusions of two or more promoters, fusions of two or more portions of promoters, MMLV LTR promoters, HIV LTR promoters, MCMV LTR promoters, EF1α, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems. Polynucleotides that can encode exogenous MHC molecules can have universal primer sequences useful for PCR mediated amplification of the exogenous MHC molecule and/or attaching sequencing adaptors useful for NGS, e.g. the universal primer sequences can flank the MHC molecule encoding polynucleotide.

An MHC molecule can be transiently expressed from an MHC polynucleotide sequence, where the MHC polynucleotide sequence does not integrate into a genome of an engineered cell. An MHC molecule can be expressed from an MHC polynucleotide sequence that is integrated into the genome of an engineered cell. Integrated MHC polynucleotide sequences can be integrated into a defined locus. MHC polynucleotide sequences integrated into a defined locus can be operably linked to and expressed from an endogenous promoter nucleotide sequence of the defined locus, or it can be operably linked to and expressed from an exogenous promoter, such as those described above.

A target cell can express a single MHC molecule. A target cell can express more than one MHC molecule, for example a target cell can express multiple MHC molecules where each MHC molecule presents a different epitope. A target cell can express 2, 3, 4, 5, 6, 7, 8, 9, 10 or more MHC molecules. The multiple MHC molecules can be random, such as multiple MHC molecules from an MHC expression library, or the multiple MHC molecules can be rationally selected. For example, rationally selected MHC molecules can be those alleles known to be expressed by a subject or patient and can be determined through HLA typing. Subjects can be known or suspected to have cancer, and can also be the same subject that a T cell or TCR is isolated or derived from. As a specific example, an antigen-specific TCR expressing cell can be engineered to express one or more TCRs identified to be expressed within a patient, and a target cell can be engineered to express one or more MHC alleles specific to the patient. Cells isolated from a patient can be also used in place of an engineered cell for antigen-specific TCR expressing cells and/or target cells.

A target cell can be present in a population of target cell with members of the population expressing different MHC molecules or combinations of MHC molecules. In one example, mammals (including humans) are heterozygous for the different MHC molecules. Thus, in general, cells isolated from a subject are naturally diverse in their MHC repertoire. For example, a human in general will have two different alleles of an MHC class I heavy-chain for each of HLA-A, HLA-B, and HLA-C, each of which is expressed in cell in a native context such that six different MHC class I molecules are generally present on a cell surface. The different MHC molecules in the population can be random, such as multiple MHC molecules from an MHC expression library. The different MHC molecules in the population can be rationally selected. Criteria for rational selection include, but is not limited, selecting MHC molecules known to be present in a subject or patient, as discussed above.

The MHC molecule can be an MHC Class I molecule expressed with a conditional ligand. As the MHC class I molecule is unstable in the absence of peptide (i.e. antigenic peptide), a recombinant MHC Class I molecule is expressed with a cleavable peptide, that upon irradiation with UV light dissociates from the complex and disintegrates. However, if the UV disintegration of the cleavable peptide is performed in the presence of a "rescue peptide," the rescue peptide will readily replace the UV irradiated peptide in the binding groove, as described in Toebes et al., 2006, *Nat. Med.* 12:246-251 and Bakker et al., *PNAS*, 2008, 105:3825-3830, the entire contents of both of which are herein incorporated by reference for all purposes. Using this technology, several assembled MHC Class I molecules can be loaded with candidate antigens, including neoantigens, to form an MHC class I antigen library for screening TCRs.

The MHC molecule can be a single chain trimer. Single-chain trimers are described in more detail in US Publication No. 2003/0003535, US Publication No. 2009/0117153, and US Publication No. 2008/0219947, each of which are incorporated by reference herein in its entirety for all purposes. Briefly, as used herein, "single chain trimers" refer to recombinant MHC molecules expressed as a single polypeptide fusion of an antigenic peptide, a β2-microglobulin, and an MHC class I heavy chain comprising the α1, α2, and α3 domains. In certain embodiments, single-chain trimers can comprise disulfide traps, as described in US Publication No. 2009/0117153 and US Publication No. 2008/0219947. Expression of MHC class II molecules and an epitope expressed as a single peptide is also described in Ignatowicz et al. (J Immunol. 1995 Apr. 15; 154(8):3852-62), incorporated by reference herein in its entirety for all purposes.

Additional description of types of MHC molecules that can be used can be found in US Publication No. 2017/0003288. Recombinant MHC Class II molecules expressed and loaded with a candidate antigen peptide are described in Novak et al., 1999, *J. Clin. Invest.* 104:R63-R67, the entire contents of which are herein incorporated by reference.

Antigenic Peptides

In examples directed to identifying TCR epitopes, an antigenic peptide (also referred to as an epitope) can be any peptide fragment capable of being presented by an MHC molecule. Antigenic peptides can be a tumor associated epitope, a neoepitope, a tumor neoepitope, a viral epitope, a phosphoepitope, a bacterial epitope, a microbial epitope, a tissue-specific self-epitope, and a self-epitope.

Neoepitopes and/or neoantigens can be from a subject known or suspected to have cancer. For identification of a patient's putative neoepitopes or neoantigens (tumor or pathogen), in silico predictive algorithmic programs can be utilized that analyze the tumor, viral, or bacterial sequencing data including whole genome, whole exome, or transcriptome sequencing data, to identify one or more mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, *Cancer Immunol Res.*, 2:522-529, the entire contents of which are herein incorporated by reference. HLAs commonly found in the human population can also be included in neoantigen prediction algorithms, such as HLA-A*02, 24, 01; HLA-B*35, 44, 51; DRB1*11, 13, 07 in caucasians, HLA-A*02, 03, 30; HLA-B*35, 15, 44; DRB1*13, 11, 03 in afro-brazialians, and HLA-A*24, 02, 26; HLA-B*40, 51, 52; DRB1*04, 15, 09 in Asians. Specific pairing of HLA alleles can also be used. Common alleles found in the human population is further described in Bardi et al. (Rev Bras Hematol Hemoter. 2012; 34(1): 25-30.)

Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

An antigenic peptide can be derived from a sample generally considered to be healthy or a sample characterized as not presenting a particular disease, condition, or phenotype. The use of antigenic peptides from healthy samples can be useful to methods benefiting from a control sample, such as methods benefiting from identifying background or off-target/cross-reactive binding by a TCR.

An antigenic peptide can be any peptide capable of being presented by an MHC class I molecule. Peptides presented by MHC class I molecule can be 7-15, 7-10, 8-9, 7, 11, 12, 13, 14, or 15 amino acids in length, and typically are 8-10 amino acids (i.e., 8, 9, or 10) in length. An antigenic peptide can be any peptide capable of being presented by an MHC class II molecule. Peptides presented by MHC class II molecule can be 11-30, 14-20, 15-18, 11, 12, 13, 14, 15, 16, 17, 18, 19, 20, 21, 22, 23, 24, 25, 26, 27, 28, 29, or 30 amino acids in length. Peptides presented by MHC class II molecule can be between 10 and 35, between 10 and 30, between 10 and 25, or between 10 and 20 amino acids in length.

An antigenic peptide can be an exogenous antigenic peptide, i.e., an exogenous peptide provided to a target cell. Exogenous antigenic peptides can be provided to an MHC molecule on a target cell using the UV cleavable peptide system described above. Exogenous antigenic peptides can be provided in an amount sufficient to replace other peptides bound to an MHC molecule, also referred to as peptide pulsing. Exogenous antigenic peptides can also be encoded for as part of the same polypeptide as an MHC molecule, such as the single-chain trimers previously described herein.

A target cell can be engineered to express an exogenous antigenic peptide. A target cell can express an antigenic peptide in addition to or in place of an endogenous antigenic peptide, e.g., a target cell expressing an endogenous native antigenic peptide can be engineered to also express a mutated version of the antigenic peptide (e.g., a neoepitope). An exogenous antigenic peptide can be encoded for by one or more antigen polynucleotide sequences, wherein the one or more antigen polynucleotide sequences are operably linked to a promoter nucleotide sequence. Polynucleotides that can encode antigenic peptides include, but are not limited to, a viral vector, a cDNA, a plasmid, a linear double-stranded DNA vector, a linear single-stranded DNA vector, and a linear single-stranded RNA vector. Examples of promoter nucleotide sequences include, but are not limited to, mammalian promoters, human promoters, viral promoters, long-terminal repeat (LTR) derived promoters from a retrovirus or lentivirus, fusions of two or more promoters, fusions of two or more portions of promoters, MMLV LTR promoters, HIV LTR promoters, MCMV LTR promoters, EF1α, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems. Polynucleotides that can encode antigenic peptides can have universal primer sequences useful for PCR mediated amplification of the antigenic peptide and/or attaching sequencing adaptors useful for NGS, e.g. the universal primer sequences can flank the antigenic peptide encoding polynucleotide.

An exogenous antigenic peptide can be transiently expressed from an antigen polynucleotide sequence, where the antigen sequence does not integrate into a genome of an engineered cell. An antigenic peptide can be expressed from an antigen sequence that is integrated into the genome of an engineered cell. Integrated antigen polynucleotide sequences can be integrated into a defined locus. Antigen polynucleotide sequences integrated into a defined locus can be operably linked to and expressed from an endogenous promoter nucleotide sequence of the defined locus, or it can be operably linked to and expressed from an exogenous promoter, such as those described above.

A target cell can express a single antigenic peptide. A target cell can express more than one antigenic peptide, for example a target cell can express multiple antigenic peptides where each antigenic peptide binds to a different MHC molecule. A target cell can express 2, 3, 4, 5, 6, 7, 8, 9, 10 or more antigenic peptides. A target cell can express greater than 10, greater than 20, greater than 30, greater than 40, greater than 50, greater than $10^2$, greater than $10^3$, greater than $10^4$, greater than $10^5$, greater than $10^6$, greater than $10^7$, or greater than $10^8$ antigenic peptides. The multiple antigenic peptides can be random, such as multiple antigenic peptides from an antigen library, or the multiple antigenic peptides can be rationally selected. For example, rationally selected antigenic peptides can be those epitopes or antigens known to be expressed by a subject or patient, or known to be associated with a particular disease, condition, or phenotype a subject is known or suspected to have. For example, subjects can be known or suspected to have cancer. Methods for predicting subject and/or cancer specific epitopes are described above. Subjects can also be the same subject that a T cell, TCR, and/or MHC molecule is isolated or derived from. As a specific example, an antigen-specific TCR expressing cell can be engineered to express one or more TCRs identified to be expressed within a patient, and a target cell can be engineered to express one or more antigenic peptides, and potentially one or more MHC alleles, specific to the patient. Cells isolated from a patient can be also used in place of an engineered cell for antigen-specific TCR expressing cells and/or target cells.

A target cell can be present in a population of target cell with members of the population expressing different antigenic peptides or combinations of antigenic peptides. For example, a library of target cells can be engineered such that each target cell population expresses a different antigenic peptide. The different antigenic peptides in the population can be random, such as multiple antigenic peptides from an antigen expression library. The different antigenic peptides in the population can be rationally selected. Criteria for rational selection include, but is not limited, selecting antigenic peptides known to be present in a subject or patient, as discussed above.

Antigenic peptides can be derived from a tumor antigen, a neoantigen, a tumor neoantigen, a viral antigen, a phosphoantigen, a bacterial antigen, a microbial antigen, a tissue-specific self-antigen, and a self-antigen. The antigen from which the antigenic peptide is derived, i.e. the unprocessed antigen, can be provided to the target cell and rely on the endogenous processing pathways of the target cell. The method employed to provide an unprocessed antigen can be selected depending on the desired processing pathway and/or MHC molecule to be targeted. For example, different methods can be chosen depending on whether presentation on MHC class I, MHC class II, or cross-presentation is desired. The unprocessed antigen can be provided to (i.e., delivered to) a target cell in the form of a polypeptide. A variety of methods of delivering unprocessed antigens are known in the art, such as electroporation, cell-penetrating peptide fusion, protein transfection, nanoparticle delivery, and vesicle mediated delivery. Other methods well-suited for delivery to MHC class II presentation pathways include, but are not limited to, targeting unprocessed antigens or cells expressing unprocessed antigens for phagocytosis by APCs, such as antibody targeting and other forms of opsonization. Targeting to phagocytic pathways can also be used to target unprocessed antigens to cross-presentation pathways. An unprocessed antigen can also be provided to a target cell by delivering an unprocessed antigen encoding polynucleotide sequence. The unprocessed antigen encoding polynucleotide sequence can take the format of any of the antigen encoding polynucleotide sequences previously described herein. Delivery of unprocessed antigen through delivery of polynucleotide sequences can have particular utility in targeting unprocessed antigens to the MHC class I presentation pathway as the unprocessed antigens are expressed within the cell.

Unprocessed antigens can also be modified for targeting to proteasomal pathways, specifically in some cases to the immunoproteasome, such as through ubiquitination of the unprocessed antigens. Target cells can also be stimulated to increase proteasomal activity, specifically in some cases to increase immunoproteasome activity, such as through interferon-gamma (IFNγ) stimulation.

Contacting

As used herein, "contacting" refers to any method of bringing an antigen-specific TCR expressing cell or a binding molecule expressing cell in proximity to and under conditions sufficient for interacting with a target cell. In general, contacting comprises incubating the cells together under conditions sufficient for trogocytosis to occur, such as in a cell culture environment (e.g., in an incubator). Contacting can include incubating the cells together in a container, such as a well in a multi-well plate, a tissue culture treated plate, a tissue culture treated multi-well plate, a flask, a tissue culture treated flask, a microcentrifuge tube, a culture tube, a test tube, a round-bottom tube, or a conical tube. Contacting can include mixing the cells together such as through mechanically disturbing the cells such that they are allowed to interact together, such as though rotating, pipetting, inverting, vortexing, or shaking. The cells can be continuously mixed, or can be mixed for a period of time and then allowed to remain undisturbed until further processed.

Membrane Components

As used herein, "membrane components" refer to any molecule associated with a cellular membrane. In general, membrane components also refer to any molecule that allow discrimination between cells, such as a membrane component generally associated with an antigen-specific TCR expressing cell or a binding molecule expressing cell but not a target cell, or vice versa.

Membrane components can be a membrane component associated with an antigen-specific TCR expressing cell or a binding molecule expressing cell, i.e., a membrane component transferred from an antigen-specific TCR expressing cell or a binding molecule expressing cell to a target cell during trogocytosis. An antigen-specific TCR expressing cell membrane component can be a membrane component generally associated with a T cell, such as a TCR; a TCR co-receptor, a CD3 TCR co-receptor, a CD4 TCR co-receptor, a CD8 TCR co-receptor, or any other component generally found on a T cell.

Membrane components can be a membrane component associated with a target cell, i.e., a membrane component transferred from a target cell to an antigen-specific TCR expressing cell or a binding molecule expressing during trogocytosis. In examples directed to identifying TCR epitopes, a membrane component associated with a target cell can be an MEW molecule.

Cells can be engineered to possess exogenous membrane components, such as a transmembrane protein, a membrane associated protein, a surface receptor, a fluorescent molecule, a cell surface protein, a sugar, or a lipid. For example, cells can be engineered to express a polypeptide that contains an extracellular domain, such as those proteins commonly used as transduction or transfection markers (e.g. LNGFRΔ). Methods used to engineer cells can be any of those previously described herein, such as using any of the polynucleotide systems that encode polypeptides previously described herein. Exogenous membrane components can contain a detectable marker, such as fluorophore (e.g., a GFP-tagged membrane component). Exogenous membrane components can contain an intracellular enzyme (e.g., a beta-lactamase) and can be employed in systems where a cell that receives the membrane component will also contain an enzyme substrate such that following trogocytosis the transferred intracellular enzyme can convert the substrate into a detectable molecule. Exogenous membrane components can contain a transcription factor and can be employed in systems where a cell that receives the membrane component will also contain means for releasing the transcription factor (e.g., a TEV protease system) such that following trogocytosis the transferred transcription factor will be released and promote expression of a detectable molecule (i.e. activate a reporter gene). Exogenous membrane components can associate through an interaction with a cellular membrane, i.e. without possessing a transmembrane motif.

Membrane components can also be labeled. For example, membrane components can be labeled prior to incubation in a trogocytosis reaction with a detectable molecule or reactive group. Labeling with a reactive group can be performed such that the membrane component can be further labeled by a detectable marker (e.g. a fluorophore) following trogocytosis. Reactive group pairs include, but are not limited to, a streptavidin/biotin system, a thiol group (e.g., cysteine) and maleimide, adamantane and cyclodextrin, an amino group and a carboxy group, and an azido group and alkynl group. Labeling can be specific, such as staining with a reactive group or fluorophore conjugated antibody. Antibodies can include antibody fragments or antibody formats known to those skilled in the art. Labeling can be non-specific or semi-specific, such as labeling with protein reactive molecules conjugated to a reactive group or fluorophore. Labeling can include labeling the cellular membrane directly, such as labeling with lipid-reactive dyes (e.g., $DiOC_{18}(3)$ [ThermoFisher]).

Membrane components can be transferred to a cell of interest from another cell the membrane component is generally associated with during trogocytosis, during which membrane components are necessarily lost from the other cell the membrane component is generally associated with. More than one membrane components can be transferred to a cell of interest. More than 2, 3, 4, 5, 6, 7, 8, 9, 10, 15, 20, 30, 40, or 50 more membrane components can be transferred to a cell of interest.

Isolating

As used herein, "isolating" refers to separating a cell, a cell type, or population of cells of interest from other populations of cells and generally includes an enrichment of the cell of interest relative to other cells. Any of the cells described herein, such as target cells or TCR expressing cells, can be isolated. Isolation can involve separating cells of interest from other cells based on properties of the cells of interest, such as having a membrane component that was transferred (i.e., received) from another cell. For example, isolation can involve identifying (i.e., detecting) a transferred membrane component, and can be either the gain of a transferred membrane component or loss of a transferred membrane component. Various labeling reagents can be used to identify the transferred membrane component, such as an antibody, a marker comprising a reactive group, and a lipid reactive marker. For example, antibodies specific for a membrane component can be used to identify a transferred membrane component, the antibodies conjugated directly to a detectable marker (e.g., a fluorophore) or recognizeable by another labeling reagent (e.g., a secondary antibody conjugated to a fluorophore). In another example, a marker comprising a reactive group specific for a functionalized membrane component can be used to identify a transferred membrane component, such as using fluorescent streptavidin to identify biotinylated membrane components. Isolation can also involve identifying a transferred membrane component in parallel with identifying other properties of a cell of interest, such as cell type (e.g. identifying T cells) or activation/signaling status (e.g. identifying PD-1, CD39, CD137, or cytokine production).

Cells of interest can be isolated such that a population of isolated cells only contain, or substantially contain, the cells of interest. Cells of interest can be isolated such that at least 1%, at least 5%, at least 10%, at least 20%, at least 30%, at least 40%, at least 50%, at least 60%, at least 70%, or at least 90% of a population of isolated cells are the cells of interest. Cells of interest can be isolated such that at least 91%, at least 92%, at least 93%, at least 94%, at least 95%, at least 96%, at least 97%, at least 98%, at least 99%, or at least 99.5% of a population of isolated cells are the cells of interest. Cells of interest can be isolated such that about 100% of a population of isolated cells are the cells of interest. Cells of interest can be isolated such that about 25%, about 37%, about 86%, or about 95% of a population of isolated cells are the cells of interest.

Isolating can involve use of a microfluidic device. For example, isolating can involve fluorescence-activated cell sorting (FACS), in which cells are isolated, or "sorted," based upon fluorescence associated with a cell of interest. Cells can be stained (i.e., contacted or mixed with) using antibodies conjugated to a fluorescent molecule. Cells can also be stained using a panel of antibodies conjugated to different fluorescent molecules. Antibodies useful for isolation can be selected based on their ability to discriminate cells of interest from other cells, such as antibodies that recognize the previously membrane components or antibodies that recognize a particular cell type. Cells can also express or be engineered to express a fluorescent molecule. Cells can be separated by FACS into a bulk collection container (e.g., every isolated cell of interest is collected in the same container). Cells can be also separated by FACS into individual collection containers, such as a multi-well plate. The individual collection container can be single-cell reaction vessels, such as those formed in single cell DropSeq applications.

Isolation can involve use of a magnet (i.e., a magnetic separation step). For example, magnetic beads or nanoparticles can be functionalized to capture cells of interest, such as conjugating antibodies to the bead or nanoparticle. In some embodiments, the magnetic nanoparticle comprises magnetic iron oxide. Examples of magnetic particles include, but are not limited to, Dynabeads™ (Thermo Fisher). Magnetic separation can comprise the step of capturing a cell of interest against a wall with a magnet and removing other cells or other elements that are not captured against the wall. Magnetic separation can involve the use of a column, such as magnetic-activated cell sorting (MACS) methods, that can separate cells based on magnetic properties. Magnetic separation can involve the use of a microfluidic device that can separate cells based on magnetic properties. The magnetic nanoparticles can be fluorescent or attached to a fluorophore directly or indirectly, and magnetic isolation methods can be used in conjunction with FACS, (e.g., before, after, or before and after FACS).

Isolation can involve use of bead capture. For example, beads or nanoparticles can be functionalized to capture cells of interest, such as conjugating antibodies to the bead or nanoparticle. A nanoparticle can be a polystyrene particle, a surface, a bead, or a polymer. Examples of beads include, but are not limited to, agaraose beads and sepharose beads. Bead capture can involve an applied force, such as centrifugation or gravity, to isolate cells. In particular embodiments, the particle or nanoparticle can be fluorescent or attached to a fluorophore directly or indirectly, and gravity isolation methods can be used in conjunction with FACS, (e.g., before, after, or before and after FACS). If magnetic, the nanoparticles separated using the magnetic methods in conjunction with FACS, (e.g., before, after, or before and after FACS).

Sequencing

Various sequencing methods can be used to determine any of the polypeptide sequences of interest described herein (e.g. an antigenic peptide or a TCR peptide), such as a sequencing a polynucleotide encoding a polypeptide of interest. Polynucleotide sequencing methods include, but are not limited to, Sanger sequencing and next generation sequencing (NGS). NGS methods include, but are not limited to, sequencing-by-synthesis platforms, Illumina/Solexa platforms (e.g., HiSeq and MiSeq), 454 pyrosequencing platforms (Roche), and SOLiD platforms (Applied BioSystems).

Portions of sequences can also be determined, such as determining one or more variable domains or complementary determining regions of a TCR.

Prior to polynucleotide sequencing, any of the polynucleotide sequences of interest described herein can be purified, e.g. extracted from a cell of interest. Particular polynucleotide sequences of interest can be genomic DNA, vector DNA, plasmid DNA, mRNA, DNA amplified by PCR, and cDNA produced by reverse transcription. Polynucleotides can be purified using techniques well-known in the field, such as phenol-chloroform extraction, agarose gel isolation, silica column based purification, cesium chloride, similar purification methods, or combinations thereof. A specific purification method can be selected based upon the particular polynucleotide of interest to be purified. Polynucleotide sequences of interest can also be purified and further processed prior to sequencing, such as amplified by PCR methods, barcoded, modified with sequencing adaptors, reverse transcribed, or any other process in preparation for sequencing. Further processed polynucleotide sequences can also undergo additional rounds of purification.

Following sequencing, sequencing results can be analyzed to identify particular polynucleotide sequences of interest.

Other methods useful for determining a polypeptide sequences of interest include, but are not limited to peptide sequencing and mass-spectrometry. For example, an antigenic peptide can be eluted from an MHC molecule on an isolated target cell and the peptide sequence can be determined by mass-spectrometry.

Barcoding

DNA barcodes can be conjugated directly or indirectly to membrane components. For example, barcodes can be conjugated to antibodies specific for membrane components. Methods and reagents for conjugating DNA oligos to antibodies are known to those skilled in the art, such a commercial kits (e.g., Solulink All-in-One Antibody-Oligonucleotide Conjugation Kit). A barcode can be specific for a specific cell population, such as a cell expressing a specific TCR, or a barcode can be specific for a specific mixture of cells, such as a cell expressing a specific TCR mixed with a another cell expressing a specific antigenic peptide.

Barcodes, in general, comprise a random nucleotide sequence. A random nucleotide sequences can be between 6-20, between 6-15, between 6-12, between 6-10, or between 6-8 nucleotides in length. A random nucleotide sequences can be positioned between the universal sequences, such as universal primer sequences useful for PCR mediated amplification of the barcode and/or attaching sequencing adaptors useful for NGS, e.g. the universal primer sequences can flank the DNA barcode. Oligos (i.e., barcodes) can take the form: UPS1-NAANGGNAANGG-NAAN (SEQ ID NO:1)-UPS2, where N represents a random nucleotide. The universal primer sequence UPS1 and UPS2 can contain no adjacent AA or GG dinucleotides.

The antibody can be a commercial antibody directed against proteins on cell surface (e.g., endogenous proteins such as CD8a, CD3e, TCR-beta, CD2 or exogenous proteins such as LNGFR, surface-expressed epitope tags).

Barcoded cells, e.g., cells labeled with a barcoded antibody, can be pooled. For example, a plurality of cells each expressing a specific TCR can be barcoded with a DNA oligo unique to each specific TCR and then pooled to form a library of antigen-specific TCR expressing cell populations. Libraries of antigenic peptide expressing cells (e.g., target cells) can be generated, such as cells barcoded with a DNA oligo unique to a unique antigenic peptide (e.g. for an antigenic peptide library), a unique MHC allele (e.g. for an MHC allele library), or a unique antigenic peptide and MHC allele pair (e.g. for an MHC:epitope pair library). Barcoded cells, included pooled barcoded cells, can be mixed with other cells and incubated together in a trogocytosis reaction. For example, a library of barcoded TCR expressing cells can be mixed (i.e. contacted) with a library of antigenic peptide expressing cells.

Following trogocytosis, cells of interest that contain barcoded membrane proteins can be isolated. Any of the isolation methods described herein can be used. The isolated barcoded cells can be sequenced to determine the barcode sequence and the information used to determine the identity of the cell the transferred membrane component originated from (e.g., the specific TCR expressing cell), and subsequently the identity of any protein or polynucleotide of interest known to be expressed by the cell the transferred membrane component originated from (e.g., the specific TCR expressed from the TCR library). Any of the sequencing methods described herein can be used. In addition, to determining the barcode sequence, other sequences of interest can be determined, such as antigenic peptide sequences. In one example, all of the unique barcodes are analyzed to determine the all of the unique barcodes present in a population. In examples directed to identifying TCR epitopes, the analysis can be used to determine the overall frequency of TCRs and/or antigenic peptides within a population. In another example, unique barcodes are analyzed in a single cell format (e.g., by Drop-Seq) to determine the all of the unique barcodes unique to a single cell, and may include one unique barcode or multiple unique barcodes (e.g., more than one cell may have interacted with the isolated cell). In examples directed to identifying TCR epitopes, the analysis can be used to determine the specific pairing of a TCR(s) with a specific antigenic peptide.

Method of Ligand Identification

The trogocytosis method can be applied to various cell-based binding interactions beyond TCR epitope identification. Accordingly, also provided herein is a method of ligand identification comprising the steps of: a) providing one or more ligand-specific binding molecule expressing cell populations; b) providing one or more target cell populations, wherein the target cell populations present one or more ligands capable of being bound by the one or more ligand-specific binding molecules; c) contacting the one or more ligand-specific binding molecule expressing cell populations with the one or more target cell populations, wherein the contacting comprises providing conditions sufficient for at least one ligand-specific binding molecule expressing cell to specifically bind at least one target cell, and wherein one or more membrane components are transferred between the ligand-specific binding molecule expressing cell and the target cell following binding; and d) isolating or having isolated i) a target cell of interest, wherein the target cell of interest comprises the one or more membrane components transferred from the ligand-specific binding molecule expressing cell following the contacting step (c); and optionally ii) a ligand-specific binding molecule expressing cell of interest, wherein the ligand-specific binding molecule expressing cell of interest comprises the one or more membrane components transferred from the target cell following the contacting step (c), e) determining or having determined i) at least a portion of a sequence encoding the one or more ligands associated with the target cell of interest, or ii) at least a portion of a binding molecule sequence encoding a binding molecule peptide associated with the binding molecule ligand-specific expressing cell of interest.

For example, other binding interactions include, but are not limited to, ligand-specific interactions with binding molecules such as an immunoreceptor, an immunoglobulin, an antibody or fragment thereof, a receptor, a chimeric receptor, a chimeric antigen receptor (CAR), a signaling receptor, a cell-surface receptor, a transmembrane receptor, or aptamers. Antibody fragments or antibody formats include, but are not limited to, Fab fragments and Fab fusion formats, Fv fragments and Fv fusion formats, single chain antibody formats, scFvs, tandem scFvs, single variable domain formats (e.g., camelid VHH), and other antibody fragments or formats known to those skilled in the art. Exemplary antibody and antibody fragment formats are described in detail in Brinkmann et al. (*MABS*, 2017, Vol. 9, No. 2, 182-212), herein incorporated by reference for all that it teaches. Accordingly, the identity of ligands of binding molecules can be determined, such as identities of an antigen, a surface antigen, an epitope, a non-classical MHC presented antigen, and a receptor ligand. Any cell expressing a binding molecule of interest, such as a B cell expressing a membrane associated antibody, can be used. Any cell expressing a ligand of interest, such as an antigen recognized by an antibody, can be used.

Any of the various methods, techniques, and aspects previously described herein can be applied to ligand and binding molecule identification, such as those describing systems and components useful for engineering of cells, isolation of cells of interest, purification of polynucleotides, sequencing of polynucleotides, and determination of peptide sequences.

Compositions of the Invention

Also provided for herein are isolated target cells of interest, wherein the target cell comprises: i) one or more T cell membrane associated components, wherein the target cell does not comprise an endogenous polynucleotide sequence encoding the one or more T cell membrane components; and ii) one or more major histocompatibility complex (MHC) alleles, wherein one or more antigenic peptides are presented on the one or more major histocompatibility complex (MHC) alleles. The one or more antigenic peptides can be encoded for by one or more antigen polynucleotide sequences. The antigenic peptide can be any of the antigenic peptides previously described herein. The target cell can be any of the cells previously described herein, such as any of the engineered cells previously described herein. The T cell membrane associated component can be any of the membrane components previously described herein, such as any of the membrane components generally associated with a T cell or any exogenous membrane component previously described herein. The MHC allele can be any of the MHC molecules previously described herein.

Any of the various methods, techniques, and aspects previously described herein can be applied, such as those describing systems and components useful for engineering of cells and isolation of cells of interest.

Also provided for herein is a polynucleotide sequence purified from any of the isolated target cells of interest.

Example 1: Methods

Cell Lines and Primary Cells

HEK-293T, Jurkat E6-1, and K562 cells were obtained from the American Type Culture Collection (Manassas, VA). Primary human PBMCs were purchased from the CFAR Virology Core Lab at the UCLA AIDS Institute. HEK-293T cells were cultured in Dulbecco's Modified Eagle Medium (DMEM; Mediatech Inc., Manassas, VA) supplemented with 10% (v/v) fetal bovine serum (FBS; Corning, NY) and 100 U/ml penicillin/streptomycin (Mediatech Inc., Manassas, VA). Jurkat and K562 cells were cultured in RPMI 1640 medium (Mediatech Inc., Manassas, VA) supplemented with 10% (v/v) FBS, 10 mM HEPES (Thermo Fisher, Waltham, MA), 50 μM β-mercaptoethanol (Sigma-Aldrich, St. Louis, MO), 1×MEM NEAA (Thermo Fisher, Waltham, MA), and 1 mM sodium pyruvate (Mediatech Inc., Manassas, VA). All cells were cultured at 37° C. with 5% atmospheric CO2.

Patients with metastatic melanoma were selected for the current analysis by being HLA-A*02:01 positive, having an adequate baseline biopsy as well as an on-treatment biopsy, and exhibiting an objective tumor response while participating in a phase 1 trial of pembrolizumab. Patients #1 and #2 received single agent pembrolizumab intravenously 10 mg/kg every 3 weeks (10Q3W). Tumor responses were evaluated starting at 12 weeks, confirmed 4 weeks after first response, and imaged every 12 weeks thereafter. Response was characterized by both the Response Evaluation Criteria in Solid Tumors (RECIST) and the immune-related response criteria (irRC). Tumour biopsy and peripheral blood cell collection and analyses were approved by UCLA IRBs 11-001918 and 11-003066. Tumor biopsies from the patients analyzed were obtained at baseline and on therapy and were processed with one aliquot immediately fixed in formalin followed by paraffin embedding for pathological analyses, a second aliquot snap frozen by immediate immersion in liquid nitrogen for genetic analyses, and a third aliquot minced fresh under sterile condition followed by DNAse/collagenase digestion to create single cell suspensions (s.c.s) before cryopreservation in liquid nitrogen. Peripheral blood mononuclear cells (PBMCs) were prepared from fresh whole blood by Ficoll-Paque density gradient centrifugation and cryopreserved. Tumor infiltrating lymphocytes (TILs) were expanded from cryopreserved s.c.s using anti-CD3 antibody (OKT3, 50 ng/mL, 48 hr exposure) and IL-2 (300 IU/mL) and re-cyropreserved at $5\times10^6$ cells/mL after 2-4 weeks. TILs were thawed and treated with DNAse for 45 min the morning of use, and stained with antibodies to CD4 (BV510, BioLegend, San Diego, CA) and CD8+(BV605, BioLegend, San Diego, CA). Live (7AAD-negative) populations of CD4 and CD8+ single-positive cells were sorted using a FACS Cell Sorter (BD Biosciences, San Jose, CA).

DNA Constructs

An MSGV-based retroviral vector (MSCV vector encoding TERT was a kind gift from the Eugene Barsov lab, with restriction sequences modified to facilitate TCR gene cloning) encoding F5 TCR, 1G4 TCR, or neoTCR genes carrying either human or murine TCR constant regions had the format LNGFRΔ-P2A-TCRα-F2A-TCRβ. LNGFRΔ is a transduction marker comprising low-affinity nerve growth factor receptor with the intracellular domain truncated and is detectable by surface staining. The MSGV-retroviral vector was also used for CD8 transductions. A lentiviral vector (modified pHAGE6 backbone was a kind gift from the Richard Mulligan lab, with restriction sequences modified to facilitate SCT and MHC gene cloning) encoding ZsGreen/eGFP and peptide-MHC single-chain trimer (SCT) composed of antigenic peptide (NY-ESO-1, SLLMWITQV (SEQ ID NO:2); MART1, ELAGIGILTV (SEQ ID NO:3); USP7mut, YLTHRVDVI (SEQ ID NO:4)), β2-microglobulin, and HLA-A2 domains via flexible GS linkers was prepared with a disulfide trap modification as described[32]. The pHAGE6 lentiviral vector was also used for transducing HLA-A2 genes in non-SCT formats, e.g., for A2-K562 cells. E2-Crimson was subcloned into a lentiviral vector. A CD3 fusion gene encoding CD3δ, CD3ε, CD3γ, and CD3ζ was subcloned into a lentiviral vector co-expressing E2-Crimson.

Cell Line Construction

Retroviruses encoding F5 TCR, 1G4 TCR, neoTCR, or CD8 were produced in HEK-293T cells by transient transfection of retroviral based plasmids and their packaging vectors (pRD114 and pHIT60) using TransIT-293 (Minis Bio, Madison, WI) according to the manufacturer's protocol. Lentiviruses encoding E2-Crimson, SCT, HLA-A2, or CD3/E2-Crimson produced in HEK-293T cells by transient transfection of lentiviral based vectors and their packaging vectors (psPAX2 and pMD2.G). 48 hours after transfection, the virus was collected, filtered through a 0.45 μm syringe filter, and used for infection. The Jurkat or K562 cells were spin-infected with viral supernatant supplemented with 10 μg/mL polybrene at 2,500 rpm and 30° C. for 90 min. On day 3 post-infection, $TCR^{high}$, $TCR^{high}$ E2-Crimson+, $TCR^{high}CD8^{high}$, $A2^{high}eGFP^{high}$, or $A2^{high}Zsgreen^{high}$ K562 (CD3− or CD3+) or Jurkat cells were sorted by flow cytometry to establish derivative cell lines as indicated. For the SCT-K562 library cells, eGFP+ K562 cells were sorted.

T Cell Activation and Transduction

T cells were stimulated, transduced, and cultured as previously described[32]. To transduce primary human T cells, PBMCs (2×106 cells/mL) were activated in 24-well plates coated with 1 μg/mL anti-CD3 (clone OKT3, eBioscience, San Diego, CA) in the presence of 1 μg/mL soluble anti-CD28 (clone CD28.2, eBioscience, San Diego, CA) and 300 U/mL IL-2 (Fisher Scientific, Tustin, CA) in T cell media (AIM-V media supplemented with 5% (v/v) human AB serum and antibiotics (pen/strep)). After 48 hours of activation, the cells were spin-infected with viral supernatant supplemented with 10 μg/mL polybrene for 90 min at 2,500 rpm and 30° C. Following spin-infection, the retroviral supernatant was replaced with fresh T cell medium containing 300 U/mL IL-2 and 1 μg/mL anti-CD28. The transduced primary T cells were cultured for 48 hours and then used for cytotoxicity assays.

Surface Biotin Labeling

F5-Jurkat cells were resuspended at 10 million cells per mL in freshly prepared biotin solution (1 mg/mL in sterile PBS, Thermo/Pierce EZ-Link Sulfo-NHS-LC-Biotin 100 mg [21335] or 8×1 mg No-Weight [21327] format) and incubated for 10 min at room temperature. The cells were quenched with 1 equivalent of FBS and incubated for 10 min at 4° C., then washed 3 times with 10 mL RPMI 1640 medium supplemented with FBS. The labeled cells were then used for co-incubation experiments.

Peptide Loading of A2-K562 Cells

Lyophilized peptides (Thermo Fisher, Waltham, MA) were reconstituted in DMSO to 10 mM and then further diluted in water to a 2 mM working stock. 5-fold serial dilutions of the peptides were performed using a 50 μM starting solution (5 μL 2 mM working stock in 195 μL serum free media (SFM)) until 80 nM was reached. Target A2-K562 cells (50K total, 0.5×106 cells/mL) were pulsed with 25 μL of 5× serial peptide dilution in a 96-well U-bottom plate and incubated for 2 hours at 37° C. After incubation, 100 μL of medium was added to each well and then centrifuged for 5 min at 1500 rpm. The cell pellets were washed once with 200 μL of medium and then resuspended in 100 μL of medium for co-incubation experiments.

Co-Incubation Assay and Cell Staining/Sorting

For experiments using F5-Jurkat, 1G4-Jurkat, MART1-K562, and NYESO-K562, co-incubations were set up in 96-well U-bottom plates at a ratio of 5:1 Jurkat-to-K562 (300K cells per well) and co-incubated for 45 min at 37° C. Ratios for co-incubation experiments involving SCT-Jurkat cells and TCR-K562 cells are indicated in the text and descriptions of the drawings. The co-incubation was then centrifuged for 5 min at 1500 rpm and the media was aspirated by vacuum. The cell pellets were resuspended with cold PBS solution containing 2 mM EDTA, then centrifuged. Cells were stained with different antibodies at 4° C. for 20 min, washed twice, and then analyzed by flow cytometry using MACSQuant Analyzer 10 (Miltenyi Biotec, Bergisch Gladbach, Germany). The following antibodies were used to detect expression of surface markers: anti-CD3-PE (clone UHCT1), anti-CD8-BV510 (clone HIT8a), anti-TCRαβ-PacificBlue (clone IP26), anti-TCRαβ-PE/Cy7 (clone IP26), anti-LNGFR-PE (clone ME20.4), anti-LNGFR-APC (clone ME20.4), anti-HLA-A2-PacificBlue (clone BB7.2), anti-HLA-A2-BV510 (clone BB7.2), and anti-muTCRαβ-PE/Cy7 (clone H57-597) (all from Biolegend, San Diego, CA).

Co-Incubation Experiments with A2-Restricted SCT and Neoantigen SCT Libraries

For the co-incubations of F5-Jurkat or 1G4-Jurkat cells (E2-Crimson+) with A2-restricted SCT library cells (eGFP+), 4.8 million F5-Jurkat or 1G4-Jurkat cells were co-incubated with 2.4 million K562 cells expressing the A2-restricted SCT library for 45 min at 37° C. The cells were stained as previously described, and trogocytosis+ target K562 cells were sorted by FACS gated on $TCR^{high}$ staining (K562-SCT cells were also gated on eGFP+ and Jurkat-TCR gated on E2-Crimson+). For A2-restricted neoantigen SCT library co-incubations, 2 million donor cells were co-incubated with 1 million acceptor cells for 45 min at 37° C. The cells were prepared for sorting by FACS analogously to the A2-restricted SCT library co-incubations.

Dextramer Binding on SCT-K562 Cells

F5 TCR or 1G4 TCR dextramers were prepared by using fluorescently-labeled streptavidin (Life Technologies, Carlsbad, CA) as previously described[32]. SCT-transduced K562 cells were stained with TCR dextramer and 7AAD (eBioscience, San Diego, CA) for 20 min at room temperature. Stained cells were analyzed by flow cytometry using MACSQuant Analyzer 10 (Miltenyi Biotec, Bergisch Gladbach, Germany).

Cytotoxicity Assays with Primary Human T Cells Using Calcein AM

To measure the cytotoxic response of effector T cells to target cells, a Calcein AM release-based cytotoxicity assay was performed as previously described[34]. Briefly, 1×106 SCT-K562 target cells were resuspended in 1 mL Calcein AM (Thermo Fisher, Waltham, MA) in cell media (5 μL/mL), incubated for 1 hour at 37° C. while shaking occasionally, then washed twice with cell media to remove residual dye. Effector T cells transduced with F5 TCR or neoTCR and target SCT cells were plated on a 96-well U-bottom plate in various effector-to-target ratios (16:1, 8:1, 4:1, 2:1, 1:1, 0.5:1, 0:1) and co-incubated for 4 hours at 37° C. After co-incubation, cell-free supernatant was carefully removed and analyzed using a fluorescence plate reader (excitation filter 485 nm, emission filter 530 nm). Percent of specific lysis was calculated using the formula [(test release−spontaneous release)/(maximum release−spontaneous release)]×100 based on the optical density measured. Target cells in the spontaneous release well were incubated with medium alone (considered as 0% lysis) and target cells in the maximum release well were incubated with 2% Triton X-100 (considered as 100% lysis).
Epitope Selection The A2-restricted SCT cDNA library contained approximately 12,055 public T cell A2-restricted epitopes from the Immune Epitope Database (IEDB).

The neoantigen SCT cDNA library contained approximately 3,000 unique neoantigens identified independently by exome/RNA sequencing of tumor material from a melanoma patient and predicting neoantigen presentation by HLA-A*02:01. Both DNA and RNA were extracted simultaneously from snap-frozen tumor biopsies (Qiagen AllPrep Kit). DNA from tumors and matched normal blood samples were sequenced at the UCLA Clinical Microarray Core. Paired-end 2×100 bp sequencing was carried out on the HiSeq 2000 platform (Illumina, San Diego, CA) following exon capture using the Nimblegen SeqCap EZ Human Exome Library v3.0 (Roche), which targets 65 Mb of genome. Sequencing generated 6-10 billion reads per sample, with each targeted base covered by an average of 90-150 reads. Sequences were aligned to the UCSC hg19 human genome reference using BWA-mem algorithm (v0.7.9). Preprocessing followed the GATK Best Practices Workflow v3, including duplicate removal (Picard Tools), indel realignment, and base quality score recalibration. Somatic mutations were called with methods modified from[35], using MuTect (v1.1.7)[36], Varscan2 Somatic (v2.3.6)[37], and the GATK-HaplotypeCaller (HC, v3.3). Only high-confidence mutations were retained, defined as those identified by at least two out of three programs. For the GATK-HC, somatic variants were determined using one-sided Fisher's Exact Test (P value cut-off≤0.01) between tumor/normal pairs. Variants were annotated by Oncotator[38], with non-synonymous mutations being those classified as Nonsense, Missense, Splice_Site, or Nonstop Mutations, as well as Frame_Shift, In_Frame, or Start_Codon altering insertions/deletions. HLA-typing was performed by ATHLATES from the whole exome sequencing data. RNA sequencing was performed using the Illumina HiSeq 2500 platform on 100-bp paired-end libraries prepared using the IlluminaTruSeq RNA sample preparation kit per the manufacturer's instructions. Reads were mapped to hg19 using TopHat2 v2.0,[39] and were quantified and normalized using Cufflinks v2.2.1[40] program and CuffNorm to generate normalized expression tables by library size (fragments per kilobase of exon per million fragments mapped, FPKM) using the geometric normalization method. Mutation-containing RNA reads were identified by a custom Python (v2.7.3) script utilizing the Biopython and pysam packages, and verified by visual inspection in the Integrated Genomics Viewer (IGV). Peptide binding predictions to HLA-A02:01 were generated by netMHC3.4[41] for 9-mer and 10-mer peptides in a sliding window around each non-synonymous amino acid-altering mutation. (Peptide sequences were derived from Ensembl GRCh37 release 74.) Candidate peptides were binned by 1) those with mutations-containing reads identified by RNA-seq, 2) those with RNA expression (FPKM>0) but no identified mutated reads, and 3) all others without detectable RNA-seq expression. Peptides were ranked and sorted by HLA binding affinity within each bin.

Library Generation

The oligo pool encoding A2-restricted public and neoepitopes were synthesized (Twist Bioscience, San Francisco, CA) and used as the template for PCR amplification using primers 5'-CAGGAGGGCTCGGCA-3' (SEQ ID NO: 67 and 5'-GATGAGCGGCCGCCGGACCCTCCGCATCC-3' (SEQ ID NO: 68) with the following program: initial denaturation step at 95° ° C. for 2 min followed by 6 cycles of 95° C. for 20 sec, 61° C. for 10 sec, and 70° C. for 15 sec, then a final extension at 70° C. for 1 min, followed by a 4° C. hold. After PCR amplification of the oligo library, the PCR amplicons were digested with NotI then inserted into a BsmBI linearized lentiviral vector (pCCLc backbone was a kind gift from the Don Kohn lab, with restriction sequences modified to facilitate SCT and MHC gene cloning) with IRES mediated co-expression of a GFP gene by In-Fusion Cloning.
PCR Amplification and Deep-Sequencing Genomic DNA of sorted SCT-K562 cells was extracted using the PureLink Genomic DNA Mini Kit (Invitrogen, Carlsbad, CA) and used as templates in barcoded PCR amplification in a Mastercycler Pro S PCR System (Eppendorf, Hamburg, Germany) with the following program: initial denaturation step at 95° C. for 2 min followed by 35 cycles of 95° C. for 20 sec, 66° C. for 10 sec, and 70° C. for 15 sec, then a final extension at 70° C. for 2 min, followed by a 4° C. hold. The primers used in PCR amplification were the following: TruSeq-Univ-SCTfixed-Forward: 5'-AAT-GATACGGCGACCACCGAGATCTACACTCTTTCCC-TACACGACGCTCTTCCGATC
TGGCCTGCTTTGTTTGCC-3', (SEQ ID NO: 69)_TruSeq-Read2-SCTfixed-Reverse: 5'-GTGACTGGAGTTCA-GACGTGTGCTCTTCCGATCT CCTCCACCACCGC-TACCTC-3' (SEQ ID NO: 70) and Truseq-Adapter-Index Reverse primer. The amplified PCR was purified using the DNA Clean & Concentrator-5 Kit (Zymo Research, Irvine, CA) following the manufacturer's protocol. The amplified barcoded DNA was quantified by Bioanalyzer (Agilent Genomics, Santa Clara, CA) and sequenced by the Illumina Genome Analyzer IIx System (Illumina, San Diego, CA).

Figure 1C:
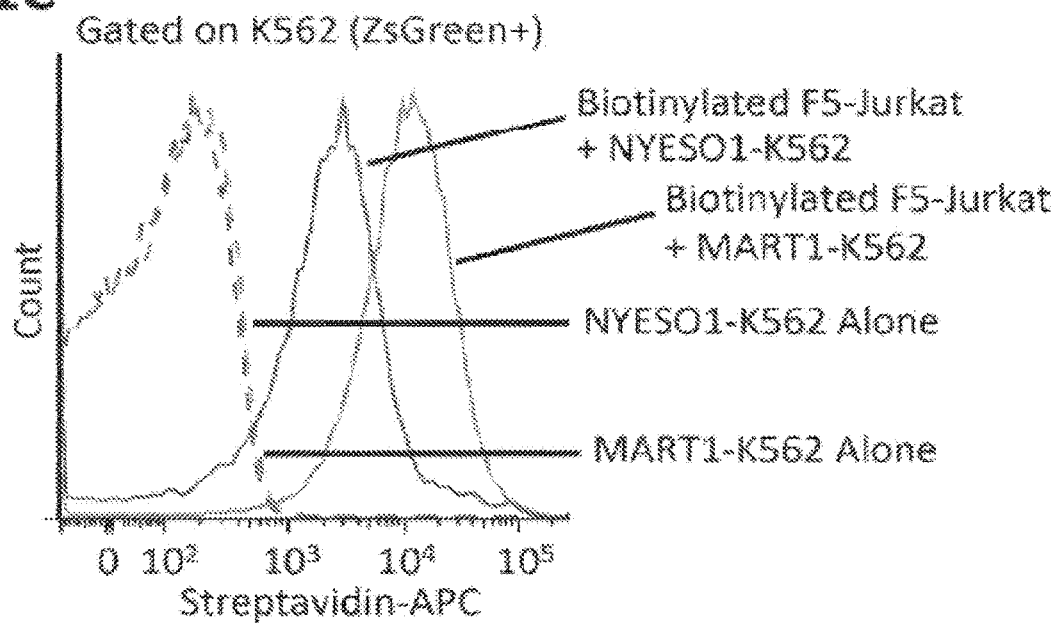
Figure 1E:
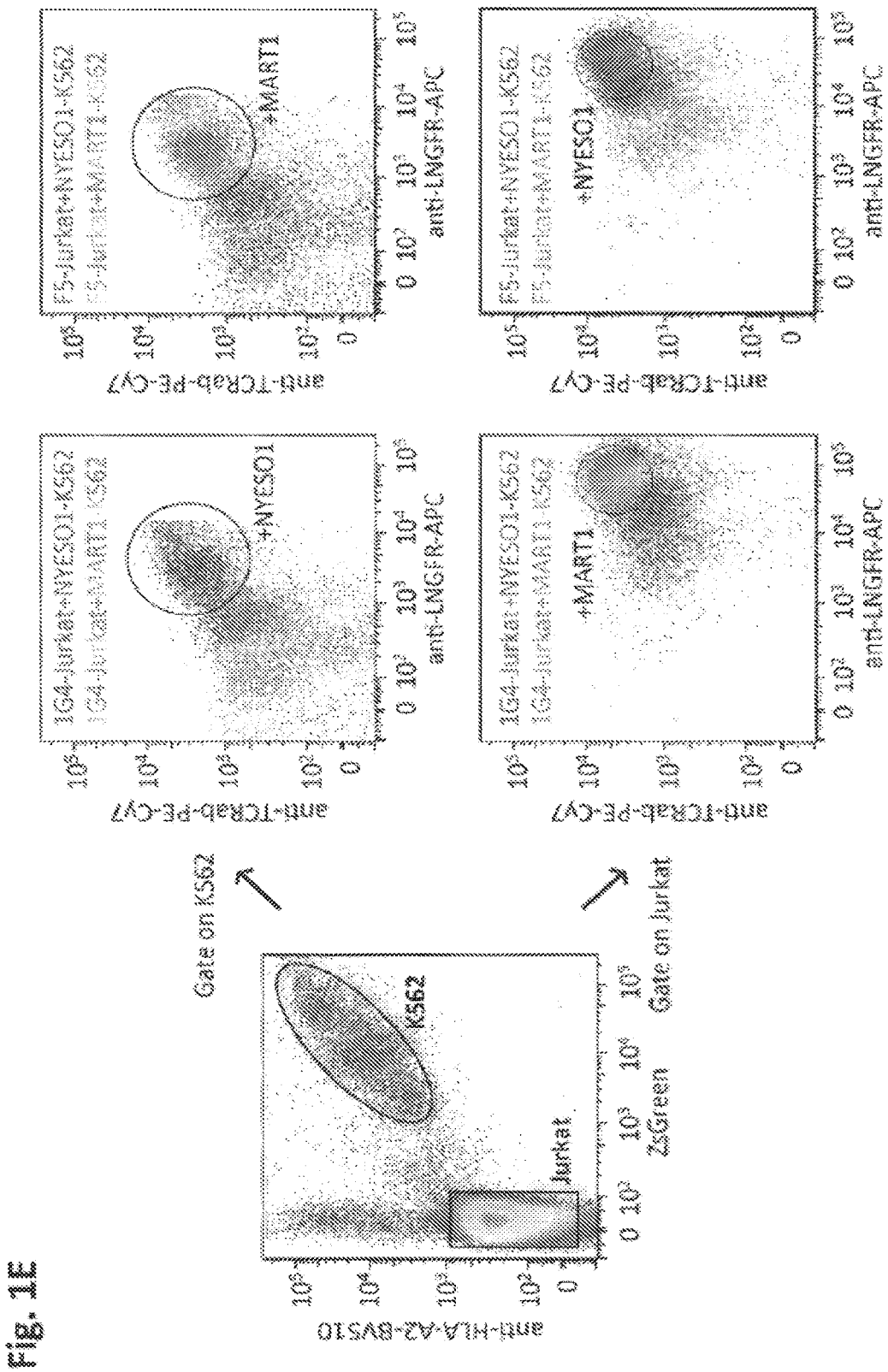
Figure 6A:
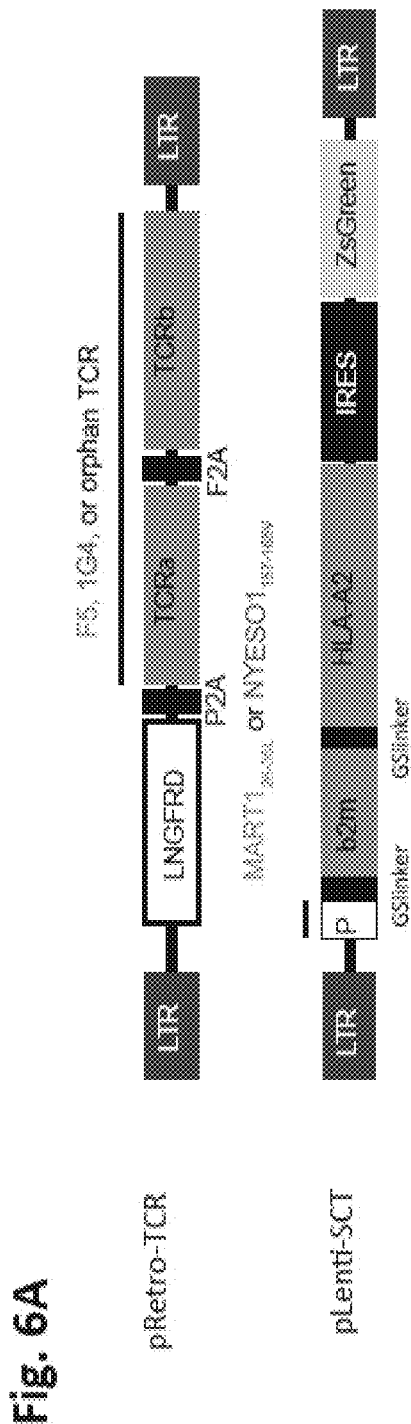
FIG. 6A-B. Establishment of Jurkat cells expressing F5 TCR or 1G4 TCR and K562 cells expressing single-chain trimer (SCT) of HLA-A2/MART1$_{26-35(A27L)}$ or HLA-A2/NYESO1$_{157-165(C165V)}$.
Figure 6B:
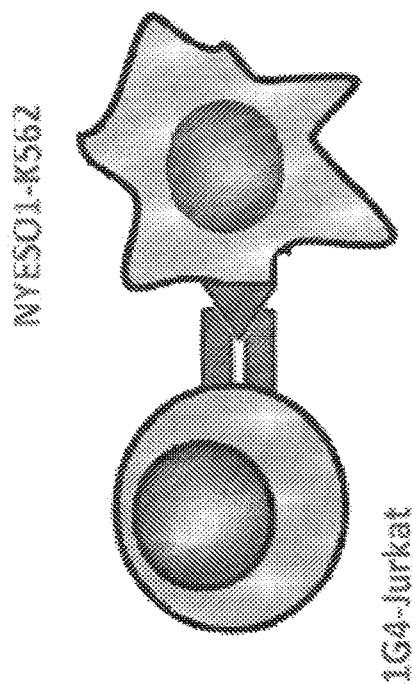
Figure 6B:
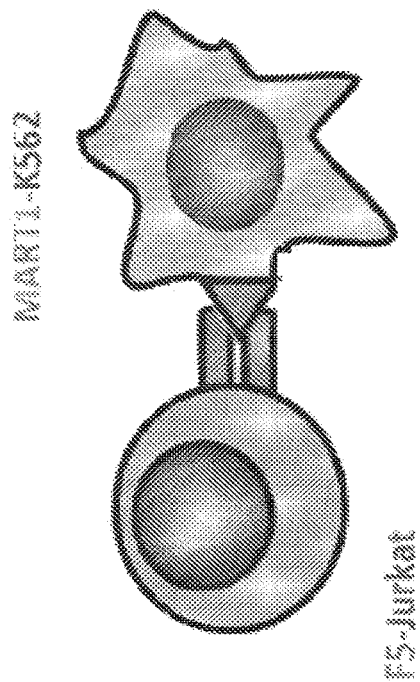
Figure 7A:
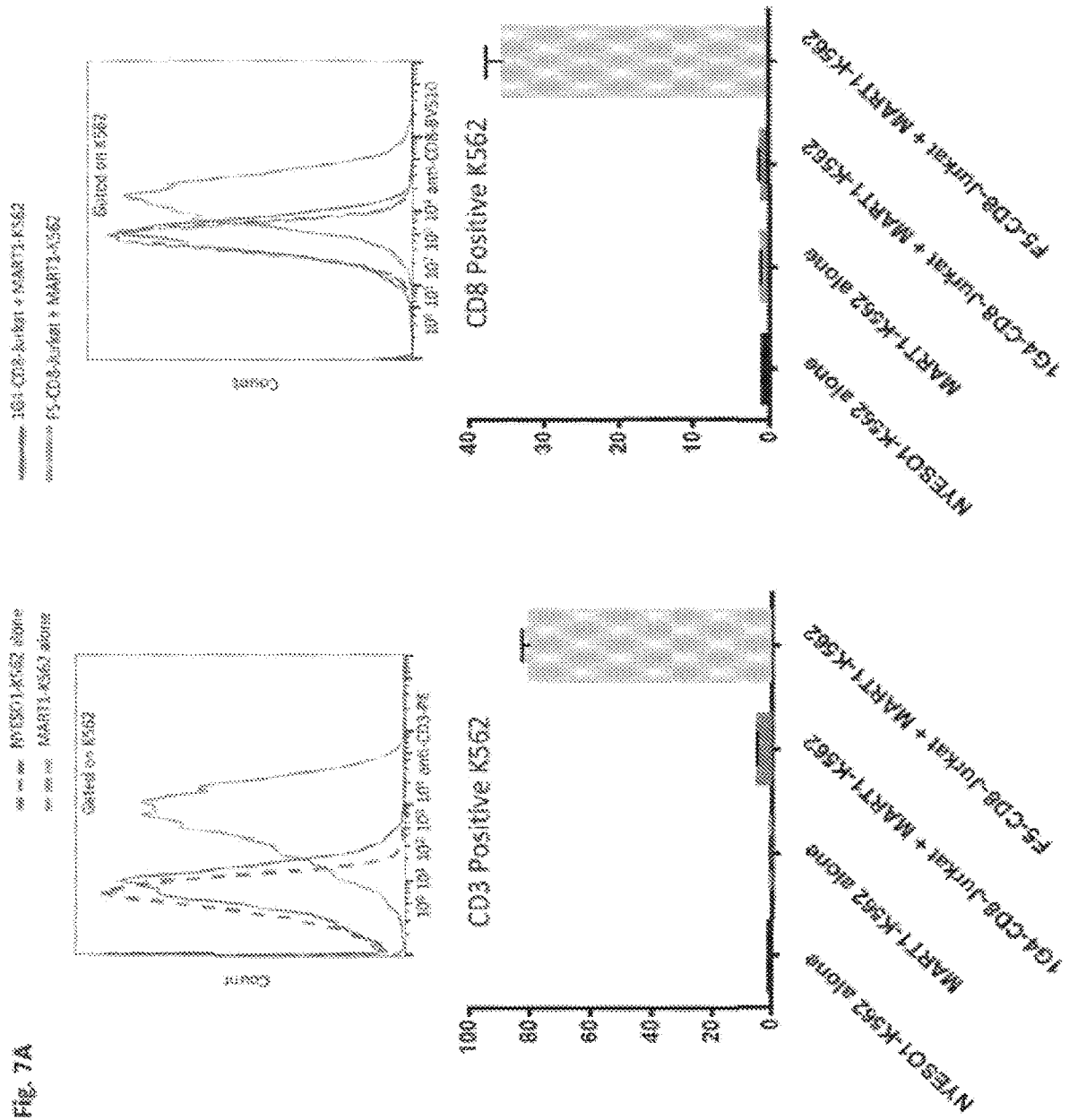
FIG. 7A-D. Trogocytosis can be tracked by multiple protein transfer.
Figure 7B:
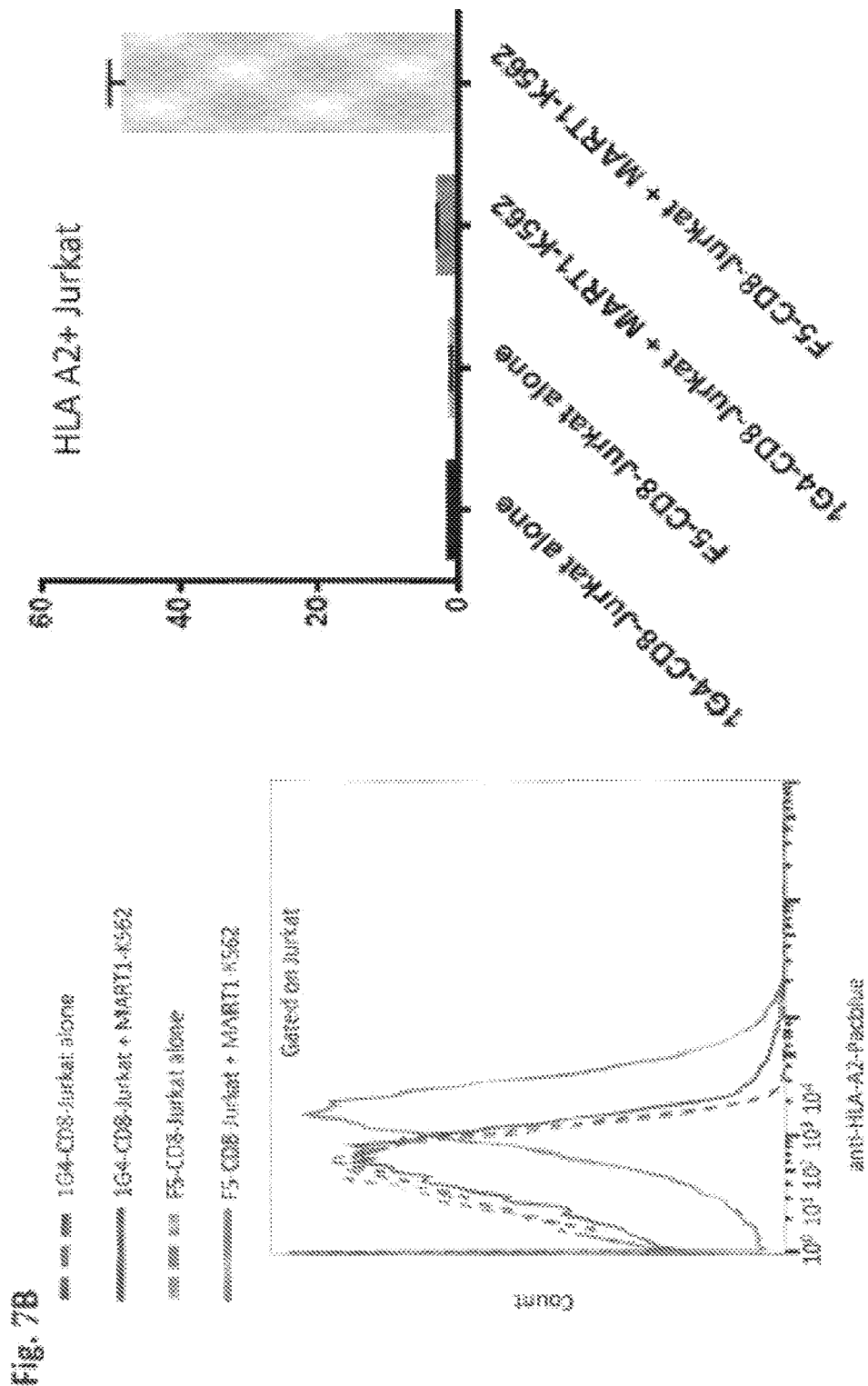
Figure 7C:
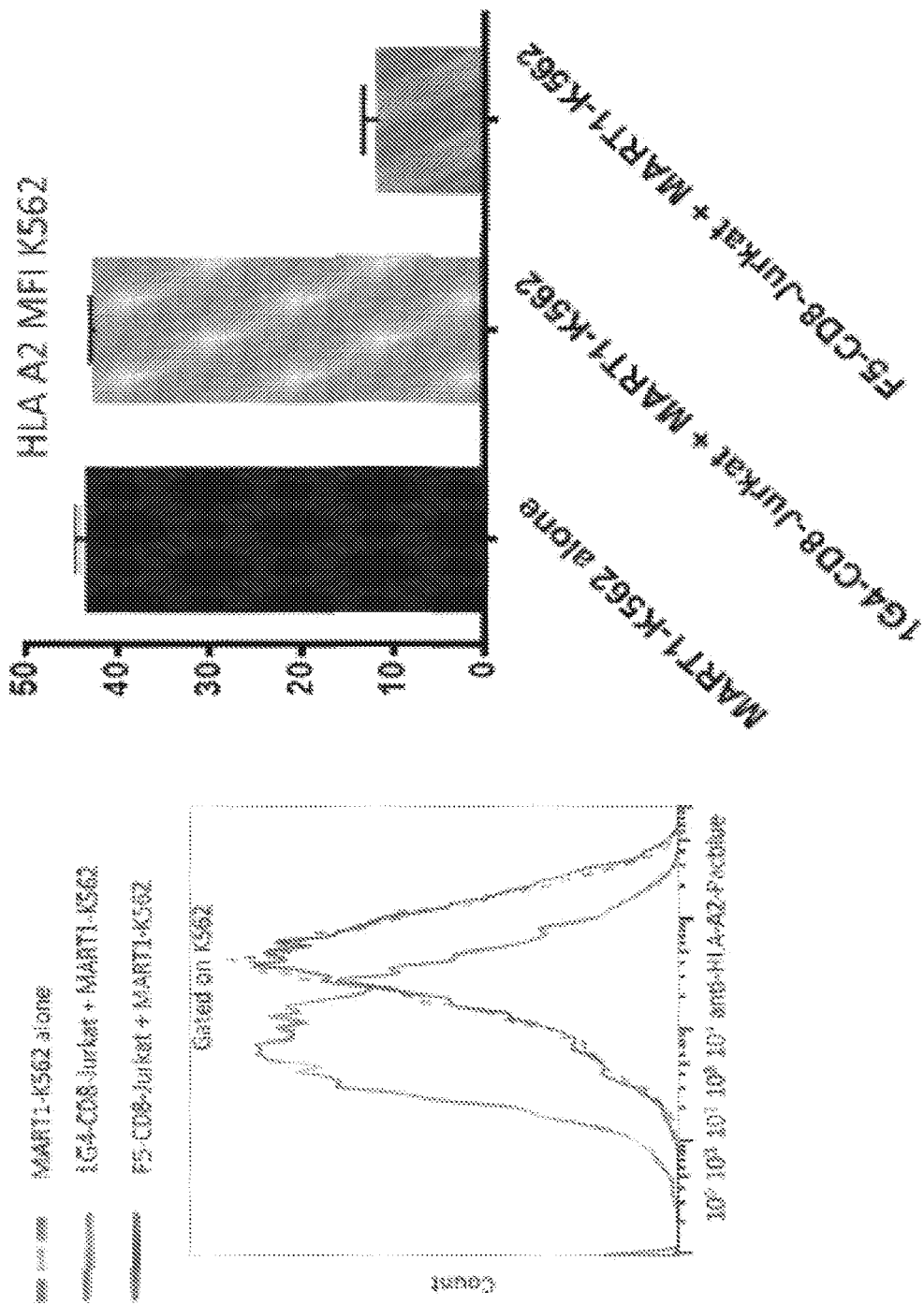
Figure 7D:
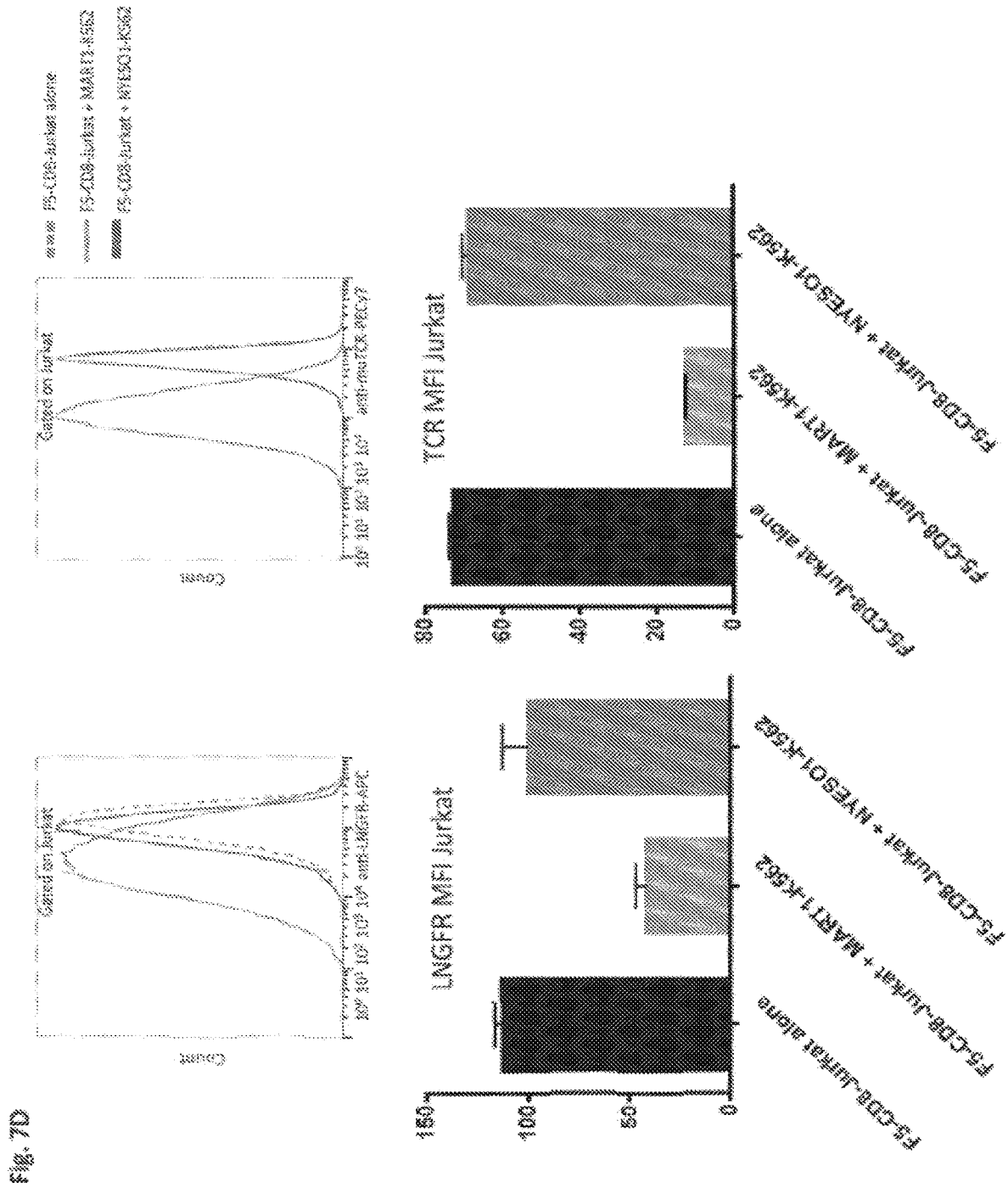

Example 2: Antigen-Specific Target Cell Trogocytosis Occurs from T Cell to APC Target Cell and can be Tracked by Multiple Protein Transfer A trogocytosis-based cell platform that can robustly identify ligands reactive to an orphan TCR of interest is described. Cell lines expressing cognate TCR-antigen pairs were established. Jurkat T cells were transduced with a retroviral vector that co-delivered the HLA-A2/MART1$_{26-35}$-specific F5 TCR genes and a transduction marker (intracellularly truncated low-affinity nerve growth factor receptor (LNGFRΔ)) (FIG. 6a, b). In parallel, K562 cells were transduced with a lentiviral vector that co-delivered a single-chain trimer (SCT) of HLA-A2/MART1$_{26-35(A27L)}$ and ZsGreen as a transduction marker (FIG. 6a, b). Jurkat T cells were transduced with A2/NYESO1$_{157-165}$-specific 1G4 TCR and K562 cells with A2/NYESO1$_{157-165(C165V)}$ SCT to establish a second pair of cognate T cell/target cell lines. To test if T cell membrane components are transferred to target cells upon antigen-specific interaction, we modified an assay for trogocytosis[18]. The standard assay involves labeling surface proteins on target cells with NHS-biotin and then monitoring the transfer of biotinylated membrane proteins (i.e., membrane components) from target cells to reactive T cells using fluorescent streptavidin. Instead, here transfer of membrane components in the opposite direction from reactive T cells to target cells was monitored. T cell surface proteins (i.e., membrane components) were labeled with NHS-biotin and monitored for their transfer to target cells during co-incubation. Following co-incubation, LNGFR[+] Jurkat T cells and ZsGreen[+] K562 were separately gated (FIG. 1a) and surface biotinylation was assessed with fluorescent streptavidin. As expected, Jurkat T cells treated with NHS-biotin were stained strongly with streptavidin (FIG. 1b), whereas K562 that were not co-incubated with biotinylated Jurkat cells were negative for streptavidin (FIG. 1c, left two peaks). Co-incubation of biotinylated F5-Jurkat cells with non-cognate NYESO1-K562 cells resulted in a >30-fold shift in streptavidin staining, indicative of non-specific biotin transfer to target cells (FIG. 1c, second peak from right). However, the co-incubation of biotinylated F5-Jurkat cells with cognate MART1-K562 cells resulted in a further 3.5-fold shift over this non-specific shift, demonstrating antigen-specific target cell trogocytosis (FIG. 1c, right peak). Interestingly, both LNGFR and TCR, representative of non-biotinylated membrane components, also exhibited a similar 2-3 fold shift when MART1-K562 cells were co-incubated with F5-Jurkat cells, without a detectable non-specific shift for LNGFR or TCR when incubated with non-cognate NYESO1-K562 cells (FIG. 1a,d). A separate experiment using antibodies alone, i.e. without biotinylating the Jurkat T cells, was performed to monitor the transfer of T cell proteins to target cells. Both NYESO1-K562 and MART1-K562 cells demonstrated a shift in LNGFR and TCR staining when incubated with Jurkat T cells expressing their respective cognate TCR but not with Jurkat T cells expressing the non-cognate TCR, confirming the antigenic specificity of target cell trogocytosis (FIG. 1e). In addition to LNGFR and TCR, the transfer of other membrane proteins, including CD3 and CD8 from Jurkat cells to K562 cells and HLA-A2 from K562 cells to Jurkat cells in an antigen-dependent manner was observed (FIG. 7a,b). Moreover, an accompanying reduction of proteins from donor cells, including HLA-A2 from K562 cells and TCR and LNGFR from Jurkat cells was observed (FIG. 7c,d). Thus, trogocytosis is bidirectional and mass balance is observed.

Figure 8A:
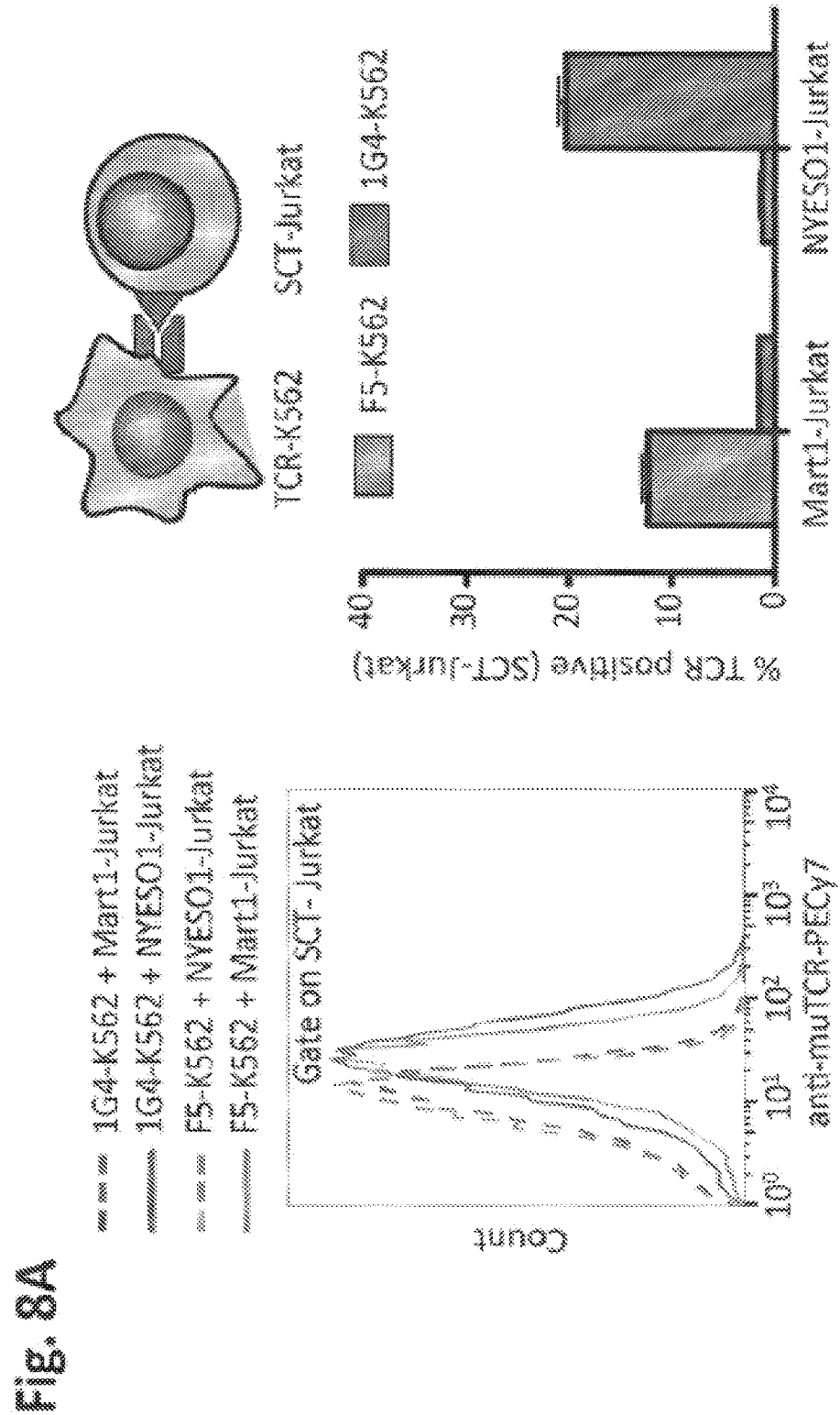
(FIG. 8A) Antigen-specific transfer of TCR after co-incubation of a 5:1 ratio of F5 or 1G4 TCR-K562 cells and MART1 or NYESO1 SCT-Jurkat cells (ZsGreen$^+$) as assessed by an anti-muTCR antibody by histogram (left panel). Histograms were quantified as a percentage of TCR positive cells (right panel). For each condition, left column represents F5-K562 cells and right column represents 1G4-K562 cells.
Figure 8B:
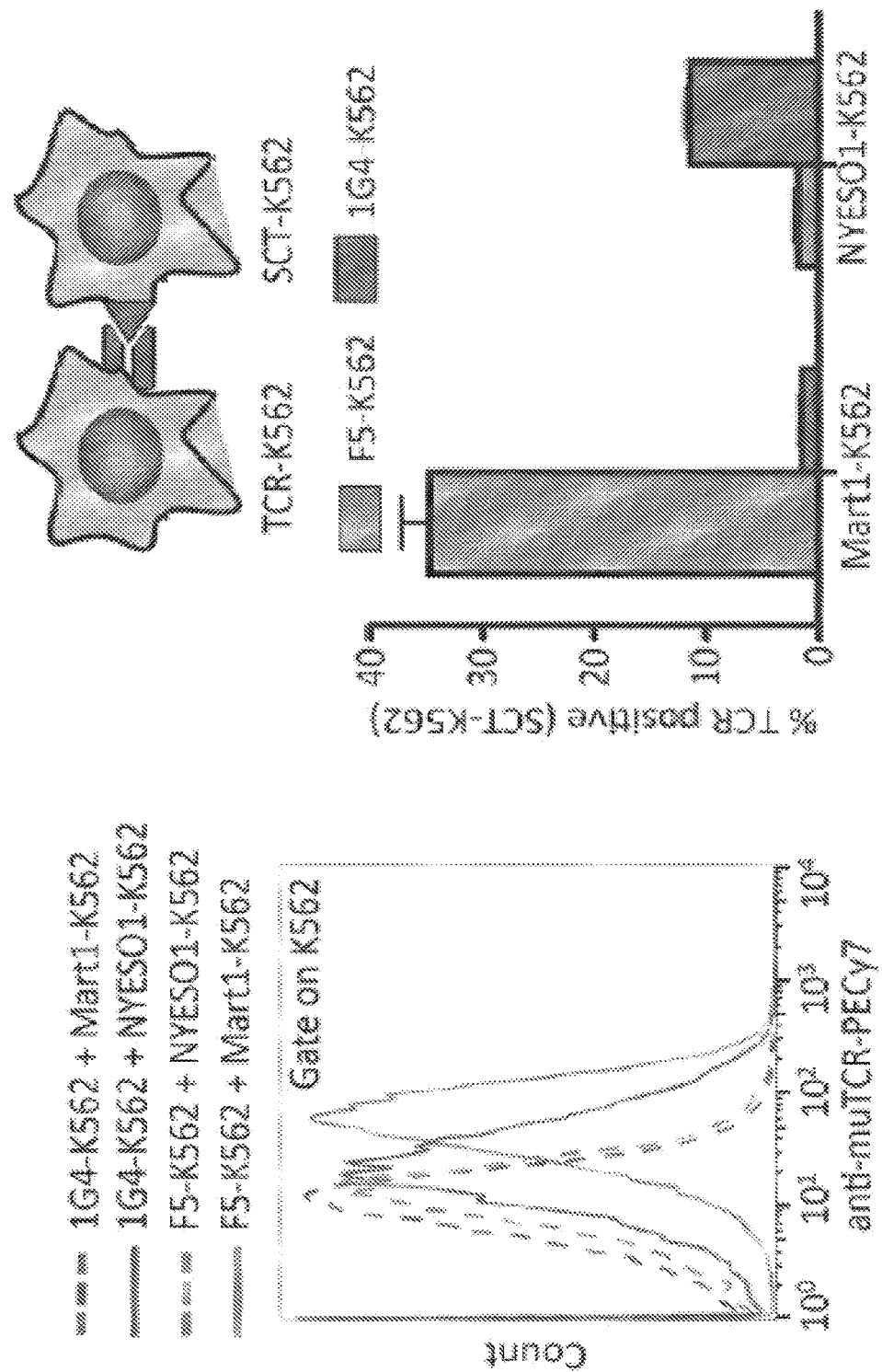
(FIG. 8B) Antigen-specific transfer of TCR after same cell type co-incubation of a 5:1 ratio of F5 or 1G4 TCR-K562 and MART1 or NYESO1 SCT-K562 (ZsGreen$^+$) as assessed by an anti-muTCR antibody by histogram (left panel). Histograms were quantified as a percentage of TCR positive cells (right panel). For each condition, left column represents F5-K562 cells and right column represents 1G4-K562 cells.
Figure 8C:
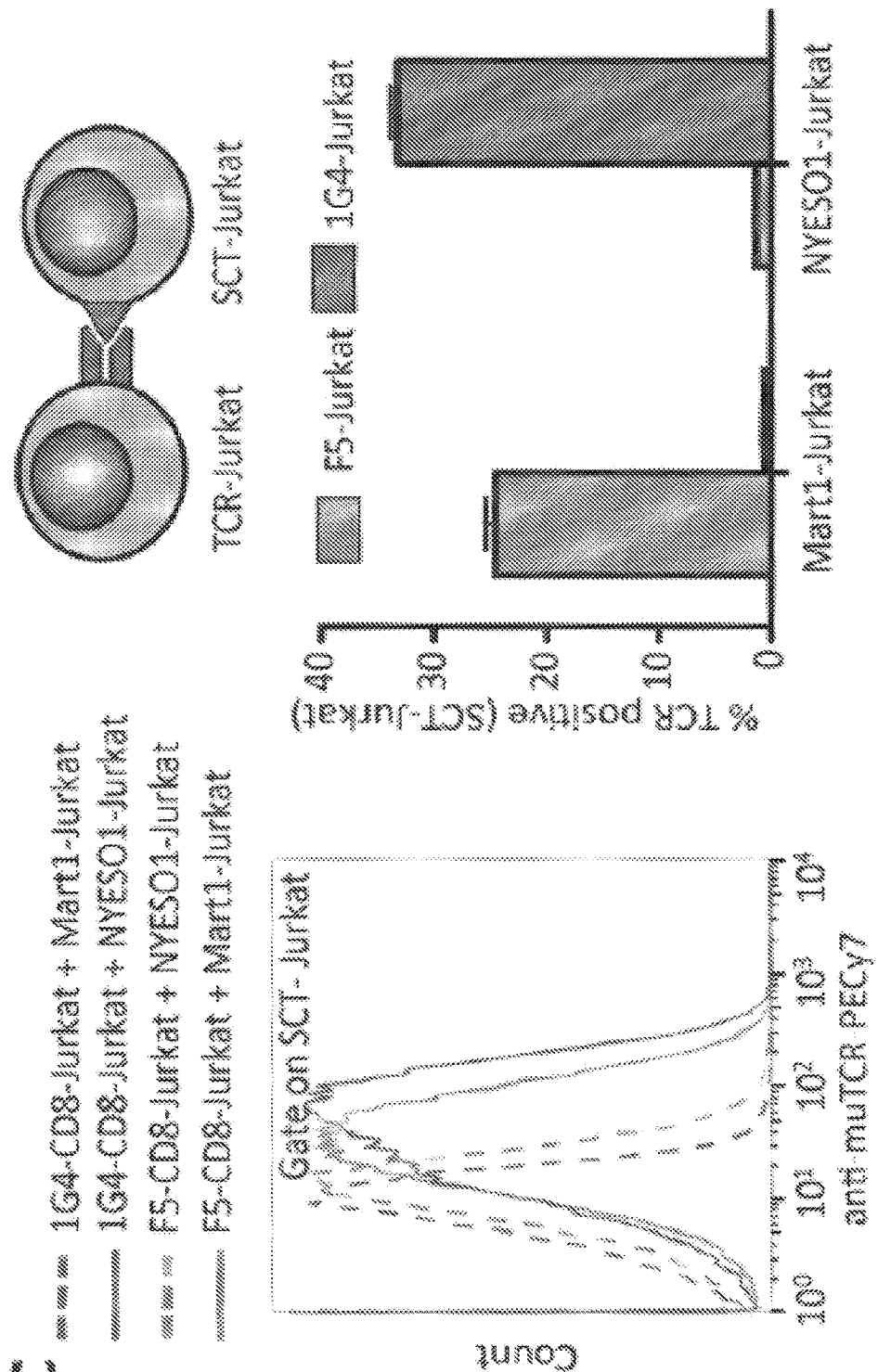
(FIG. 8C) Antigen-specific transfer of TCR after co-incubation of a 1:1 ratio of F5 or 1G4 TCR-Jurkat and MART1 or NYESO1 SCT-Jurkat (ZsGreen$^+$) as assessed by an anti-muTCR antibody by histogram (left panel). Histograms were quantified as a percentage of TCR positive cells (right panel). For each condition, left column represents F5-Jurkat cells and right column represents 1G4-Jurkat cells.

To determine if trogocytosis is dependent on donor cell/acceptor cell identity, K562 cell lines and Jurkat cell lines expressing either TCR or SCT were generated and the co-incubation experiments were performed using all pairing combinations (TCR-K562 with SCT-Jurkat, TCR-K562 with SCT-K562, TCR-Jurkat with SCT-Jurkat). Antigen-specific TCR transfer for all cell pairings was observed (FIG. 8a-c), indicating that target cell trogocytosis occurs independently of the donor and acceptor cell identity.

Example 3: Trogocytosis is Titratable and Augmented by CD8 Coexpression

Figure 9A:
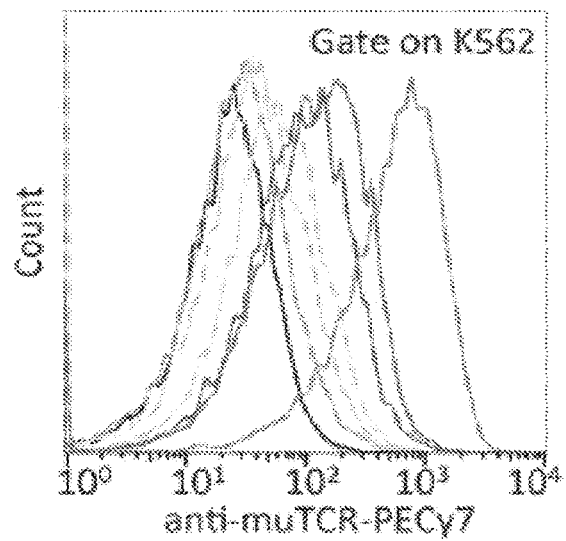
Figure 9B:
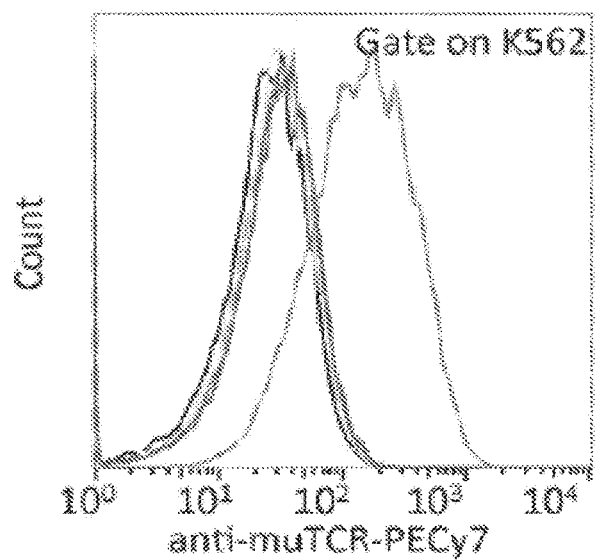
Figure 9C:
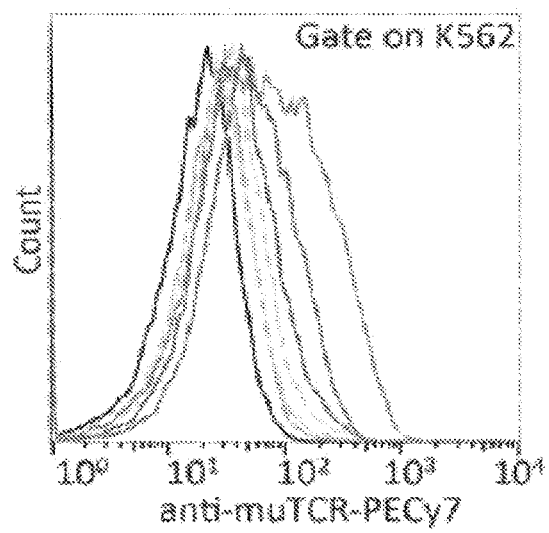
Figure 9D:
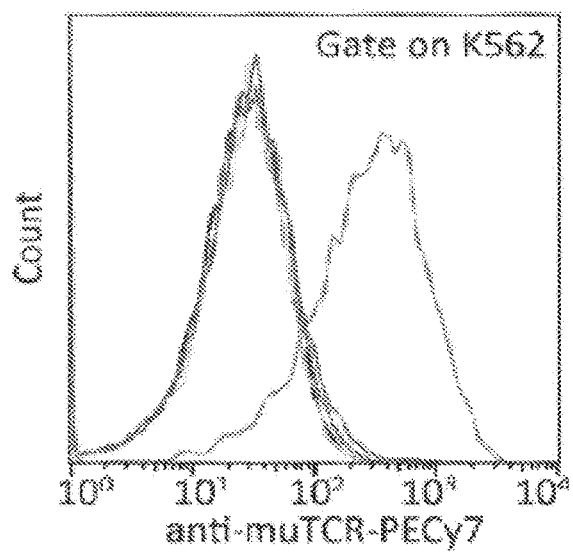

The density of pMHC complexes presented on target cells is important for TCR recognition[21]. To test if trogocytosis is quantitatively titratable, F5-Jurkat or 1G4-Jurkat cells were co-incubated with HLA-A2 expressing K562 cells (A2-K562) that were pulsed with different doses of MART1 heteroclitic peptide (ELAGIGILTV (SEQ ID NO:3)) ranging from 0.016-10 uM. The number of trogocytosis[+] target cells, as quantified by staining for percent TCR positive, increased with the dose of MART1 peptide pulsed onto A2-K562 cells (FIG. 2a, top panel and FIG. 9a). There was no significant increase in the number of trogocytosis[+] target cells when F5-Jurkat cells were co-incubated with A2-K562 target cells pulsed with non-cognate NYESO1 heteroclitic peptide (SLLMWITQV (SEQ ID NO:2)) (FIG. 2a, bottom panel and FIG. 9b). Similarly, following co-incubation with 1G4-Jurkat cells, there was an increase in the number of trogocytosis[+] target cells only for A2-K562 target cells pulsed with increasing doses of cognate NYESO1 heteroclitic peptide (FIG. 2a and FIG. 9c,d). These data suggest that target cell trogocytosis is pMHC-density-dependent.

Figure 2B:
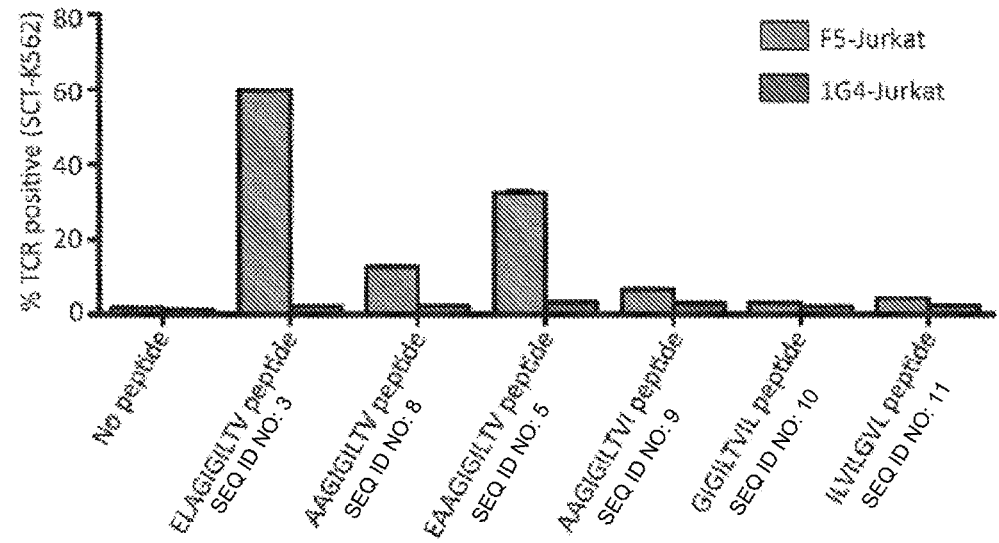
Figure 2B:
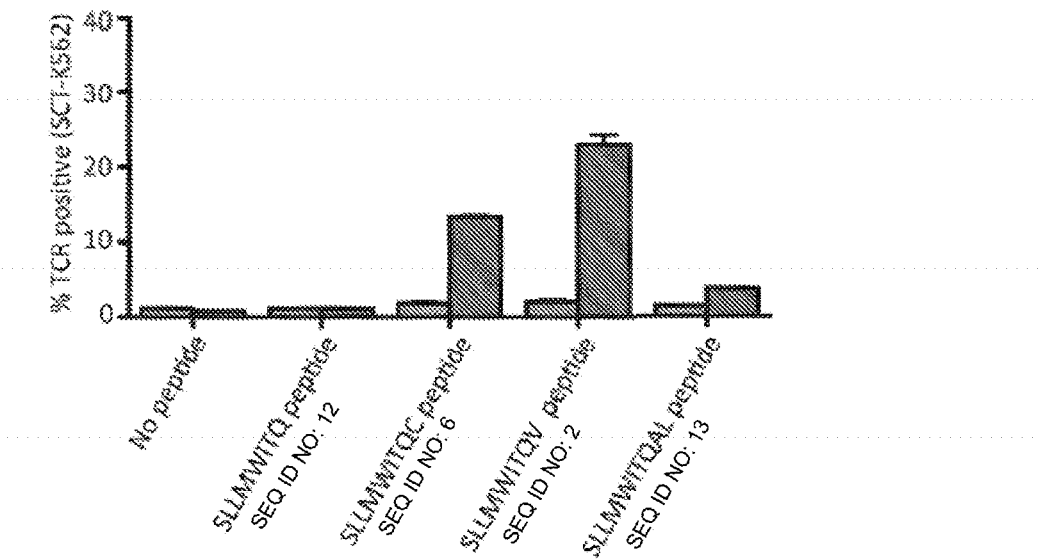
Figure 9E:
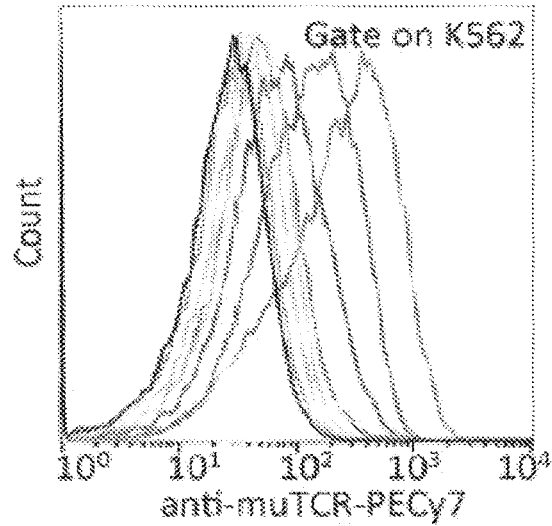
Figure 9F:
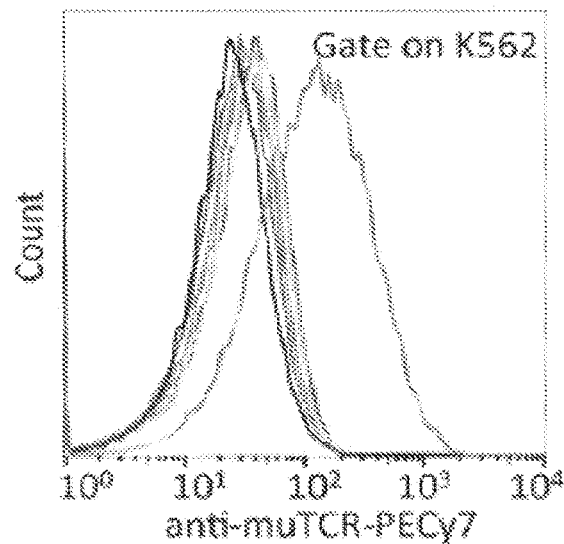
Figure 9G:
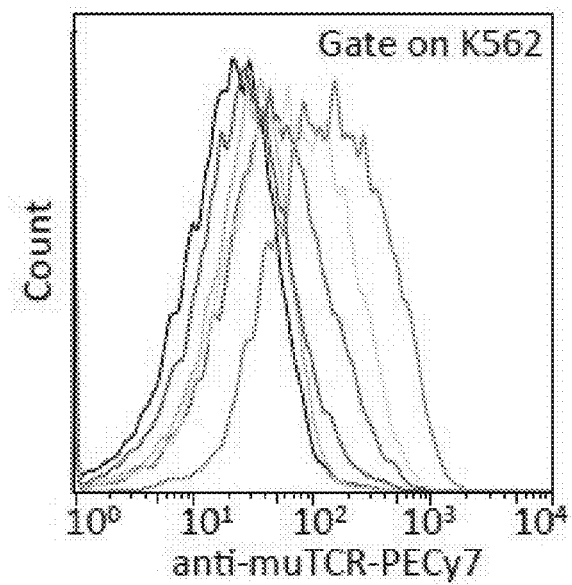
Figure 9H:
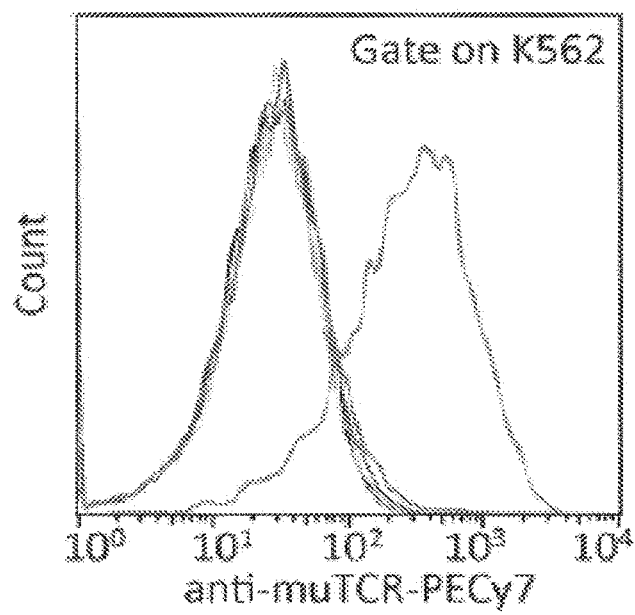

F5 TCR-expressing T cells respond to different MART1 peptide sequence variants to different extents[22]. For example, F5 TCR is more responsive to the heteroclitic ELA peptide than the native MART1 EAA peptide. The extent to which different MART1 peptide variants elicit trogocytosis was examined. F5-Jurkat or 1G4-Jurkat cells were co-incubated with A2-K562 cells that were pulsed with the same dose of different MART1 peptide variants. An increase in the percentage of trogocytosis[+] target cells was observed in the mixture of F5-Jurkat and ELA peptide-pulsed A2-K562 cells in comparison to F5-Jurkat cells co-incubated with A2-K562 cells pulsed with native EAA peptide or other peptide variants (FIG. 2b, top panel and FIG. 9e,f). Similarly, there was an increase in the percentage of trogocytosis[+] target cells when 1G4-Jurkat cells were co-incubated with A2-K562 cells pulsed with heteroclitic NYESO1 peptide than in comparison to A2-K562 cells pulsed with native peptide or other peptide variants (FIG. 2b, bottom panel and FIG. 9g,h).

Figure 9I:
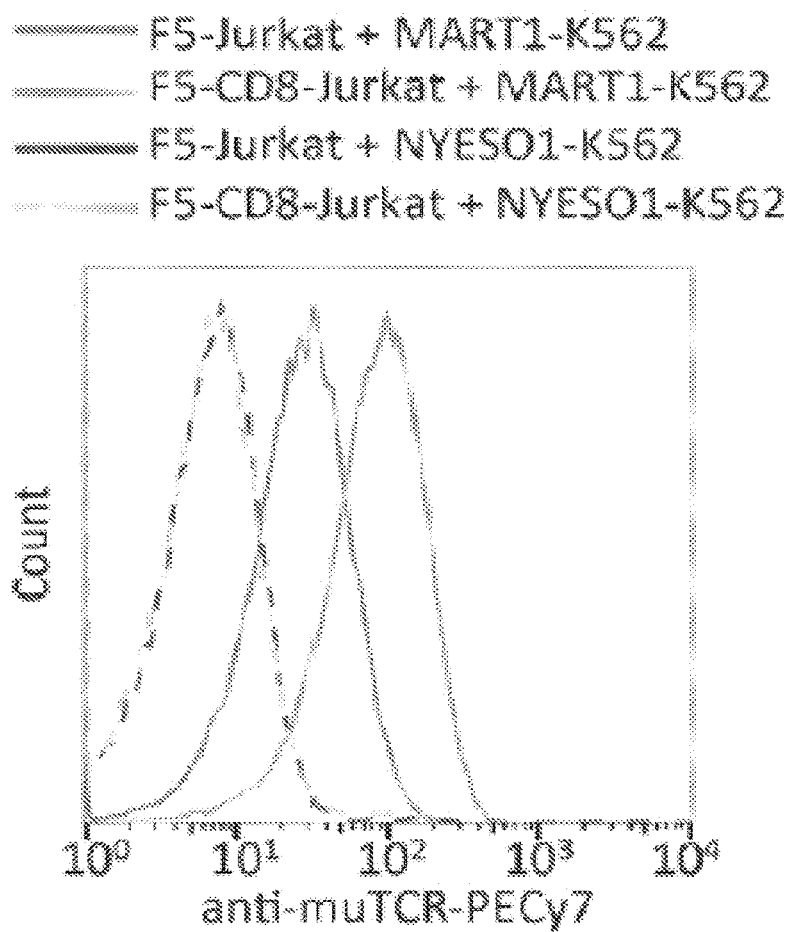

Coexpression of CD8 increases the avidity of the TCR-pMHC interaction by binding to MHC-I directly, enabling lower affinity TCRs to engage[23]. To examine if CD8 enhances trogocytosis, F5-Jurkat or 1G4-Jurkat cells that were transduced with CD8 were incubated with NYESO1-K562 and MART1-K562 cells and the transfer of TCR to the target K562 cells was measured. CD8 retroviral transduction assessed by staining for CD8a directly. Jurkat cells engineered to co-express CD8 increased trogocytosis relative to those only expressing TCR by ~3-fold (FIG. 2c and FIG. 9i,j). Thus, the results suggest that target cell trogocytosis correlates with the responsiveness of the TCR to the presented peptide and is also enhanced by co-expression of CD8.

Figure 10A:
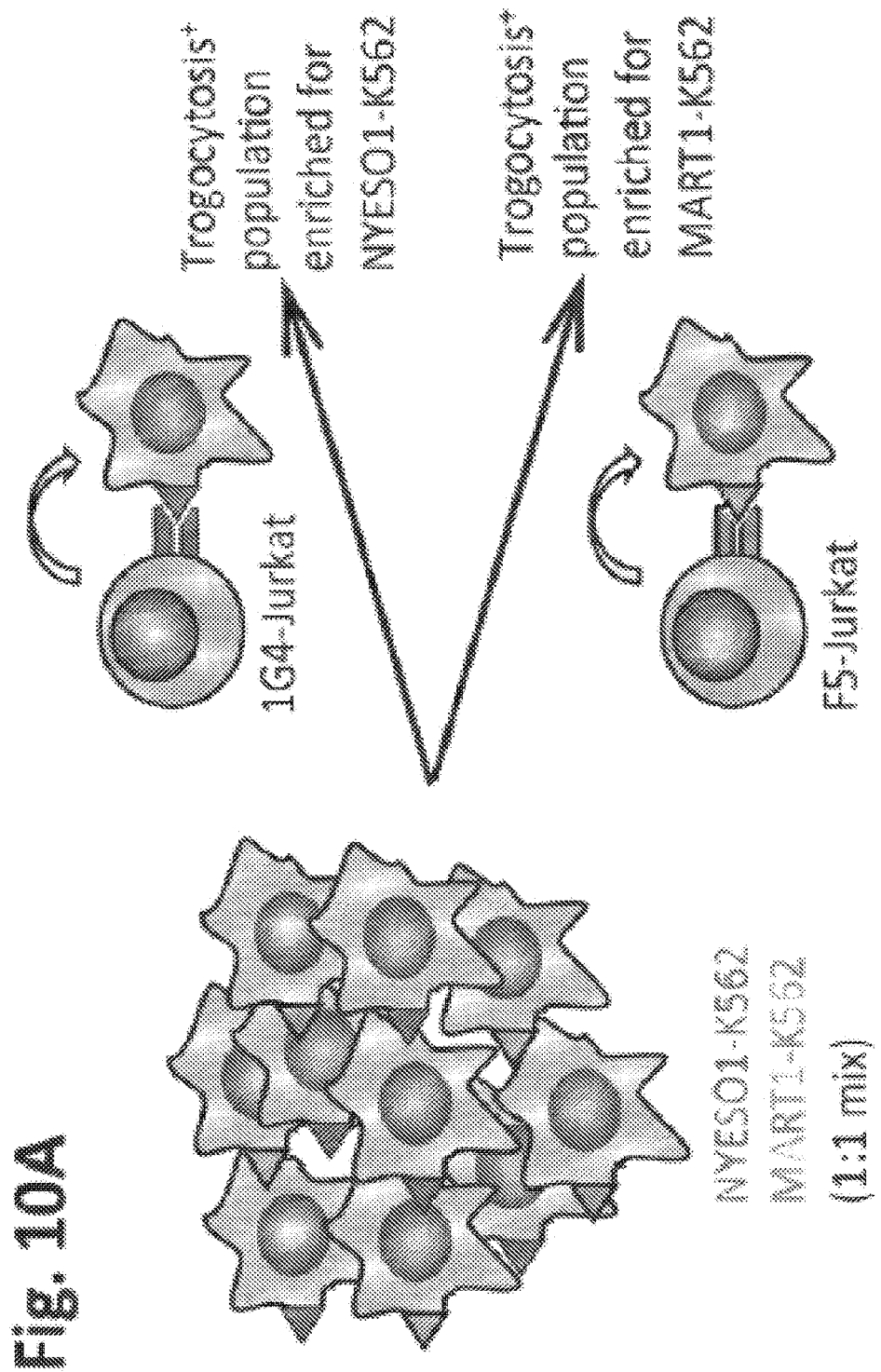
Figure 10B:
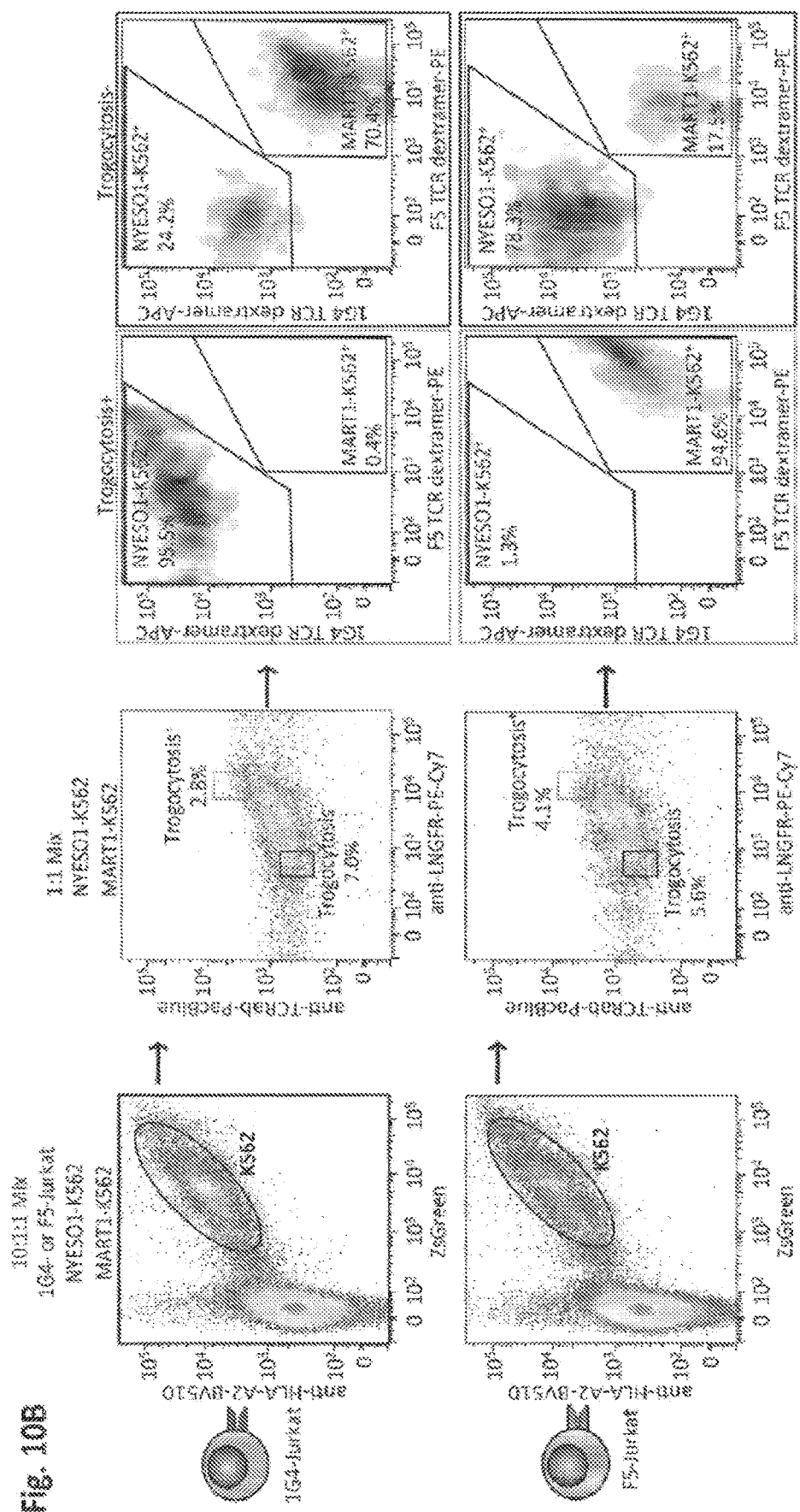

Example 4: Target Cell Trogocytosis Enables Isolation of Cognate Epitope-Presenting Target Cells In the previously described examples, target cell trogocytosis assays were performed under conditions such that only a single T cell-target cell pair is present, i.e., one TCR-expressing T cell derivative is co-incubated with one epitope-presenting K562 derivative. However, it is possible that interaction/activation alone is antigen-specific and that, once interacted/activated, T cells transfer membrane to any cell they subsequently contact. The potential interaction between activated T cell and non-cognate target cells would complicate library applications, in which rare cognate epitope-presenting target cells would be selected from far more numerous non-cognate epitope-presenting cells. To determine whether target cell trogocytosis enables separation of cognate epitope-presenting target cells from non-cognate epitope-presenting cells, either 1G4-Jurkat or F5-Jurkat T cells were co-incubated with a 1:1 mixture of NYESO1-K562 and MART1-K562 target cells. The cell mixture was then labeled with soluble 1G4 or F5 TCR dextramers allowing determination of the antigenic composition of target cells undergoing trogocytosis (FIG. 10a). When a mixture of NYESO1-K562 and MART1-K562 target cells was co-incubated with 1G4-Jurkat cells, trogocytosis⁺ target cells (HLA-A2⁺ZsGreen⁺LNGFR$^{high}$TCR$^{high}$) were highly enriched (95.1%) for cognate NYESO1-K562 cells (FIG. 10b,c). A concomitant enrichment for non-cognate MART1-K562 cells (70.8%) over cognate NYESO1-K562 cells (23.7%) was observed among trogocytosis⁻ target cells gated for low staining of LNGFR and TCR. Similarly, co-incubation of the target cell mixture with F5-Jurkat cells enriched MART1-K562 (94.9%) among trogocytosis⁺ target cells and NYESO1-K562 (76.3% vs 18.8% MART1-K562) among trogocytosis⁻ target cells. Thus, target cell trogocytosis is itself antigen-specific and enables resolution of antigen-expressing target cells from non-antigen-expressing cells.

Figure 3A:
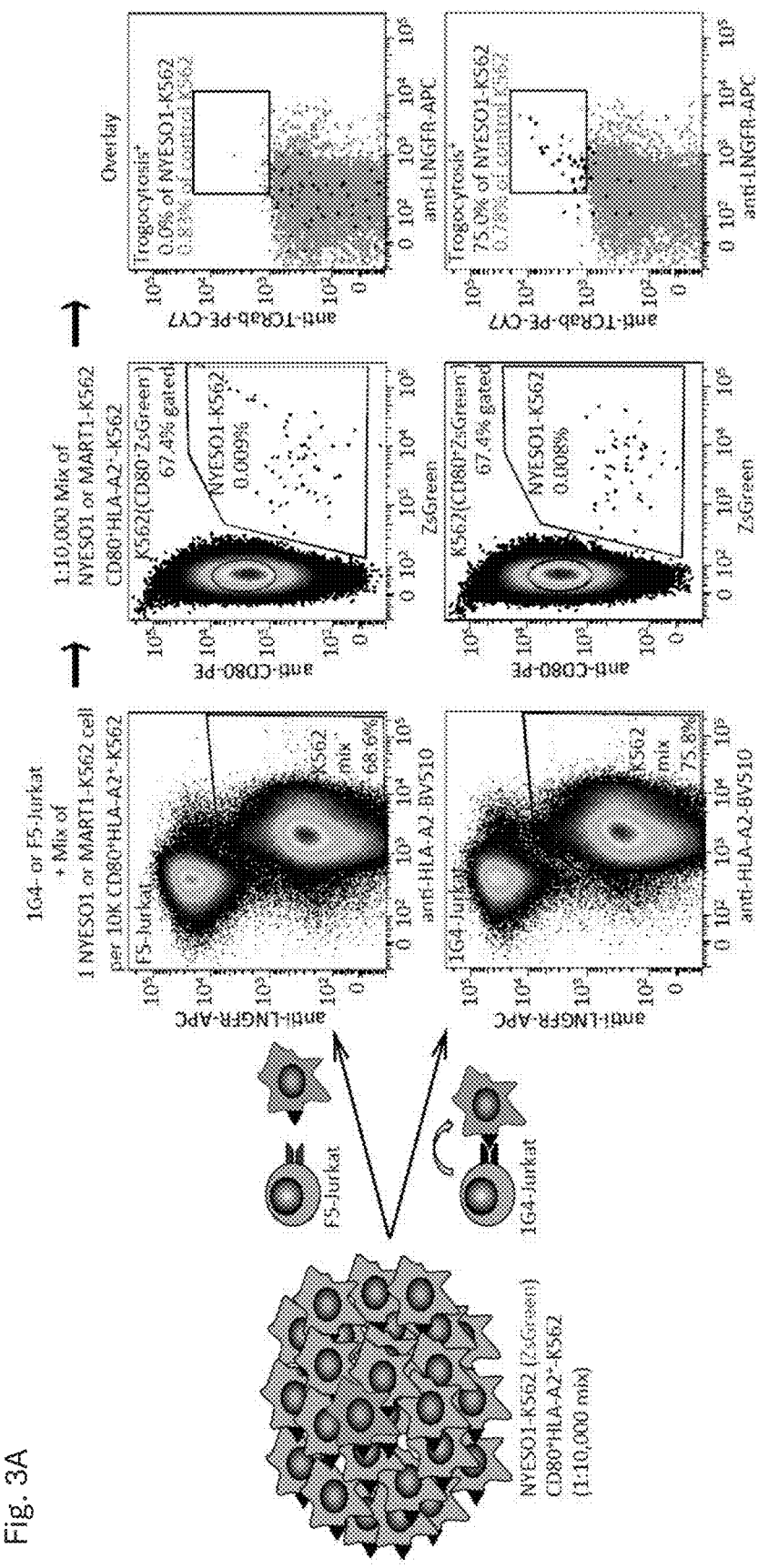
FIG. 3A-B. Target cell trogocytosis is sufficiently sensitive to identify one cognate antigen expressing target cell in 10,000 non-antigen-expressing cells.
Figure 3B:
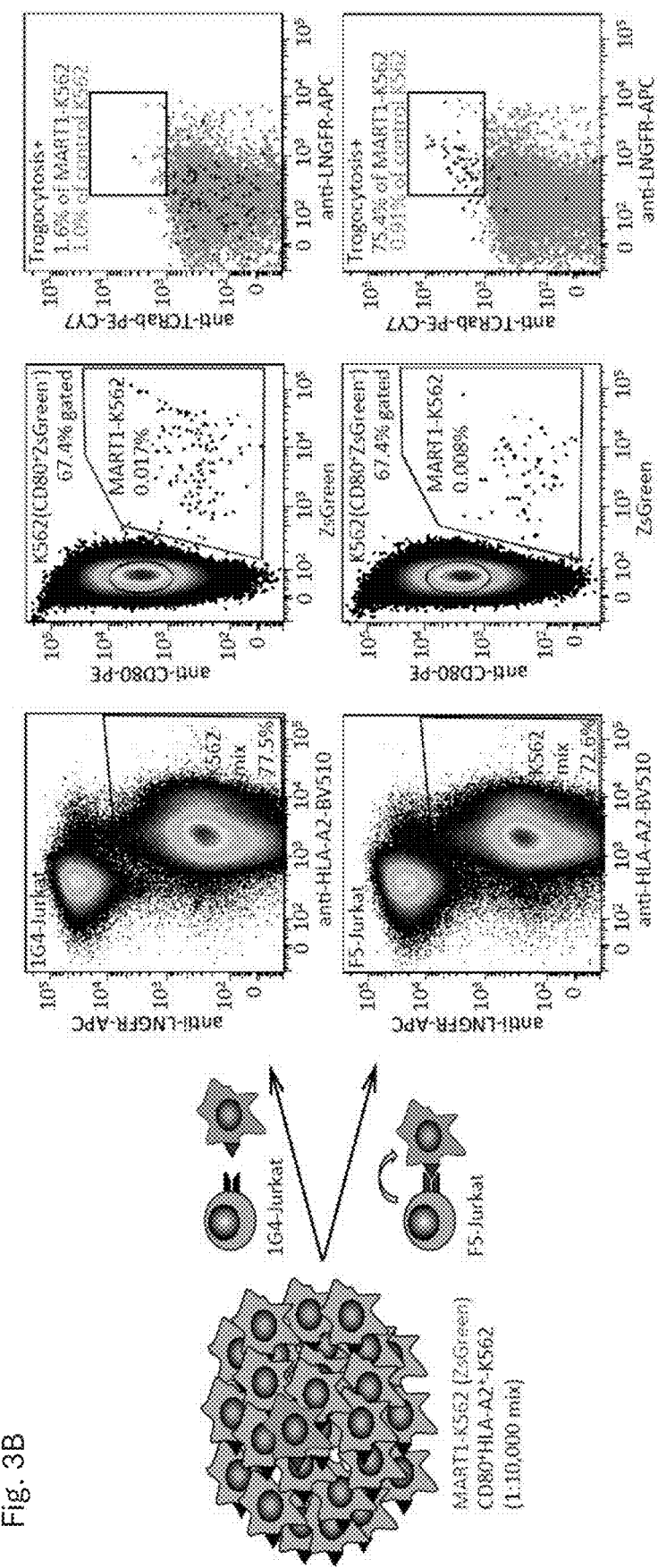

A proof-of-concept library simulation was performed to demonstrate the applicability of trogocytosis monitoring for library screening applications. NYESO1-K562 cells (expressing ZsGreen) were diluted 1:10,000 into CD80⁺HLA-A2⁺ K562 cells (not expressing ZsGreen) (CD80⁺HLA-A2⁺ K562 cells were a kind gift from the Owen Witte lab). The diluted mixture was co-incubated with either 1G4-Jurkat or F5-Jurkat cells and trogocytosis monitored among CD80⁻ZsGreen⁺ (NYESO1-K562) and CD80⁺ZsGreen⁻ (control, HLA-A2⁺ K562) target cells (FIG. 3a). In both co-incubations, NYESO1-K562 cells constituted ~0.01% of all target cells, as expected. Trogocytosis analysis was performed and a marked difference was observed in the percentage of trogocytosis⁺ NYESO1-K562 target cells (HLA-A2⁺ZsGreen⁺LNGFR$^{high}$TCR$^{high}$) between NYESO1-K562 co-incubated with non-cognate control F5-Jurkat cells (0.0%) and cognate 1G4-Jurkat cells (70.8%). In contrast, there was only minimal trogocytosis observed, potentially reflecting background levels, for control CD80⁺HLA-A2⁺ K562 cells following co-incubation with either Jurkat cell type (0.35% vs 0.33%). Additional experiments using one MART1-K562 cell per 10,000 control cells was performed, yielding a similar result for the corresponding K562-Jurkat cell pairs: incubation with cognate F5-Jurkat resulted in an increased percentage of trogocytosis⁺ MART1-K562 cells relative to 1G4-Jurkat cells (73.4% vs 1.6%) but only minimal trogocytosis with control cells (0.46% vs 0.41%) (FIG. 3b). Thus, target cell trogocytosis can be used to detect cognate antigen-expressing target cells at a ratio of at least as low as 1:10,000.

Figure 4A:
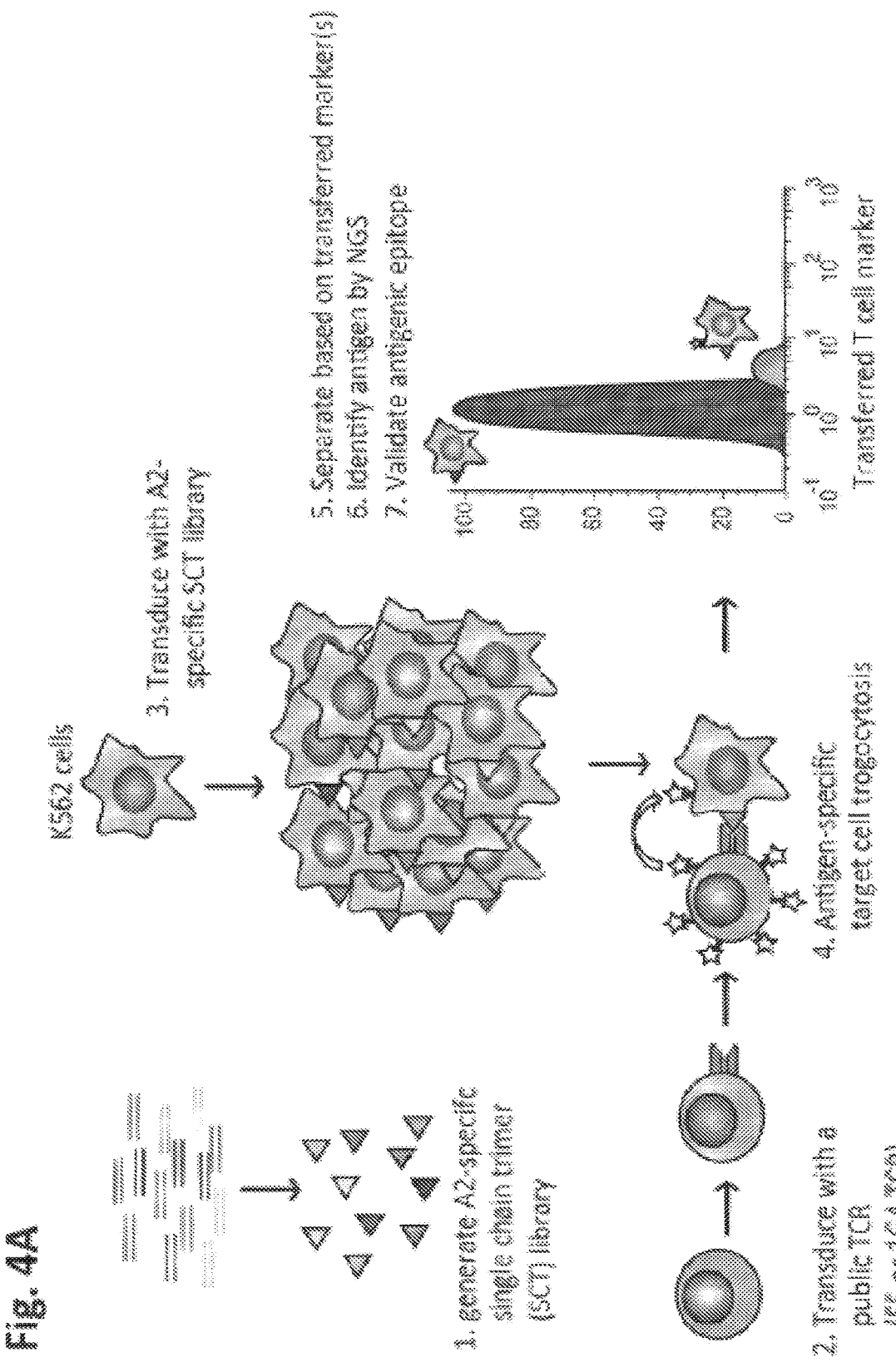
Figure 4B:
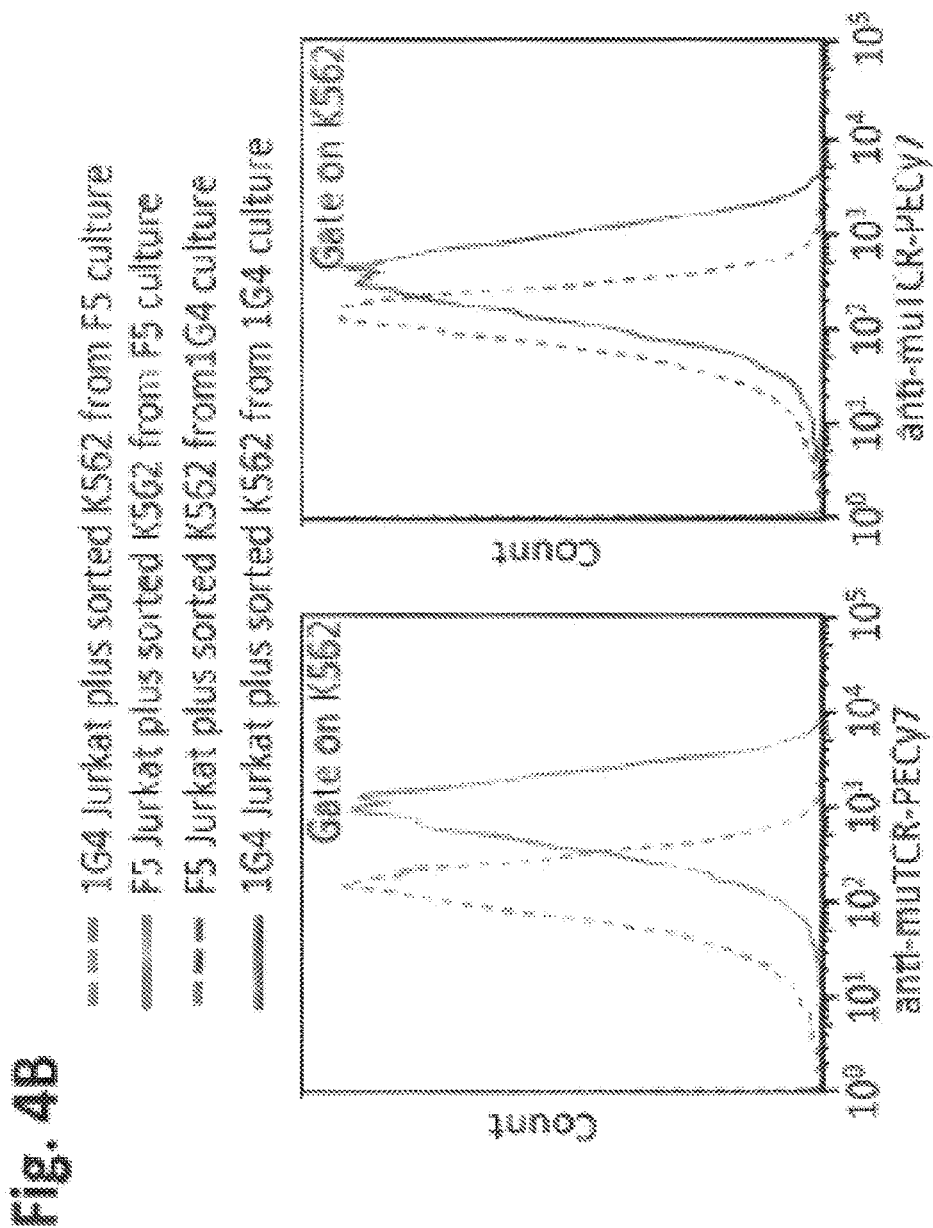

Applications for target cell trogocytosis for ligand discovery was further examined in the context of an extensive library of ligands. An A2-restricted SCT cDNA library containing 12,055 public T cell epitopes from the Immune Epitope Database (IEDB) ranging from 8-12 amino acids in length was generated, including the epitopes specific to the F5 and 1G4 TCRs (MART1 and NYESO1, respectively). K562 cells were transduced with the A2-restricted SCT library, and the transduced target cell library was co-incubated with F5-Jurkat or 1G4-Jurkat cells. Trogocytosis⁺ target K562 cells were sorted by fluorescence-activated cell sorting (FACS) gated on TCR high staining (K562-SCT cells were also gated on eGFP⁺ and Jurkat-TCR gated on E2-Crimson+) (FIG. 4a). After two rounds of sorting trogocytosis⁺ cells, where each round included performing a trogocytosis co-incubation followed by FACS sorting, trogocytosis experiments were performed to validate the specificity of the sorted K562 cells. Twice sorted K562 cells from F5-Jurkat co-incubation cultures were subsequently co-incubated again with either F5-Jurkat cells or 1G4-Jurkat cells. The sorted target cells demonstrated increased trogocytosis, as measured by TCR staining, when incubated with F5-Jurkat cells in comparison to 1G4-Jurkat cells, suggesting the sorting enriched for cells that preferentially interacted with F5-Jurkat cells. (FIG. 4b, left panel). Likewise, twice sorted K562 cells from 1G4-Jurkat co-incubation cultures demonstrated increased trogocytosis, as measured by TCR staining, when incubated with 1G4-Jurkat cells in comparison to F5-Jurkat cells, suggesting the sorting enriched for cells that preferentially interacted with 1G4-Jurkat cells. (FIG. 4b, right panel). Furthermore, target K562 cells sorted following co-incubation with F5-Jurkat cells were 95% positive for F5 TCR dextramer staining (increased from 37% after one round of sorting) (FIG. 4c, top panel) and target K562 cells sorted following co-incubation with 1G4-Jurkat cells were 86% positive for 1G4 TCR dextramer staining (increased from 25% after one round of sorting) (FIG. 4c, bottom panel). By contrast, sorted cells were negative for dextramer staining in non-cognate pairings for both rounds of sorting (FIG. 4c). These results strongly suggest that selection was TCR-dependent and suggested that the ligands presented on the enriched target cells are related to the cognate ligands for F5 and 1G4, respectively. To determine the identity of the ligands presented by the sorted populations, target cells from the second round of each trogocytosis selection were subjected to next-generation sequencing (NGS) using the Illumina platform to identify the enriched epitopes. Eight of the top 9 enriched ligands presented by trogocytosis⁺ cells sorted from the F5-Jurkat co-culture were the cognate native and heteroclitic ligands (EAAGIGILTV (SEQ ID NO:5) and ELAGIGILTV (SEQ ID NO:3)) for F5 TCR or closely-related ligands (differing in ≤3 positions from the cognate ligand). The top 2 ligands presented by trogocytosis⁺ cells sorted from the 1G4-Jurkat co-culture were likewise the cognate native and heteroclitic ligands (SLLMWITQC (SEQ ID NO:6) and SLLMWITQV (SEQ ID NO:2)) for 1G4 TCR (FIG. 4d). These data demonstrate that target cell trogocytosis provides a platform for identifying cognate ligands and cross-reactive ligands of similar sequence for orphan TCRs.

Figure 5A:
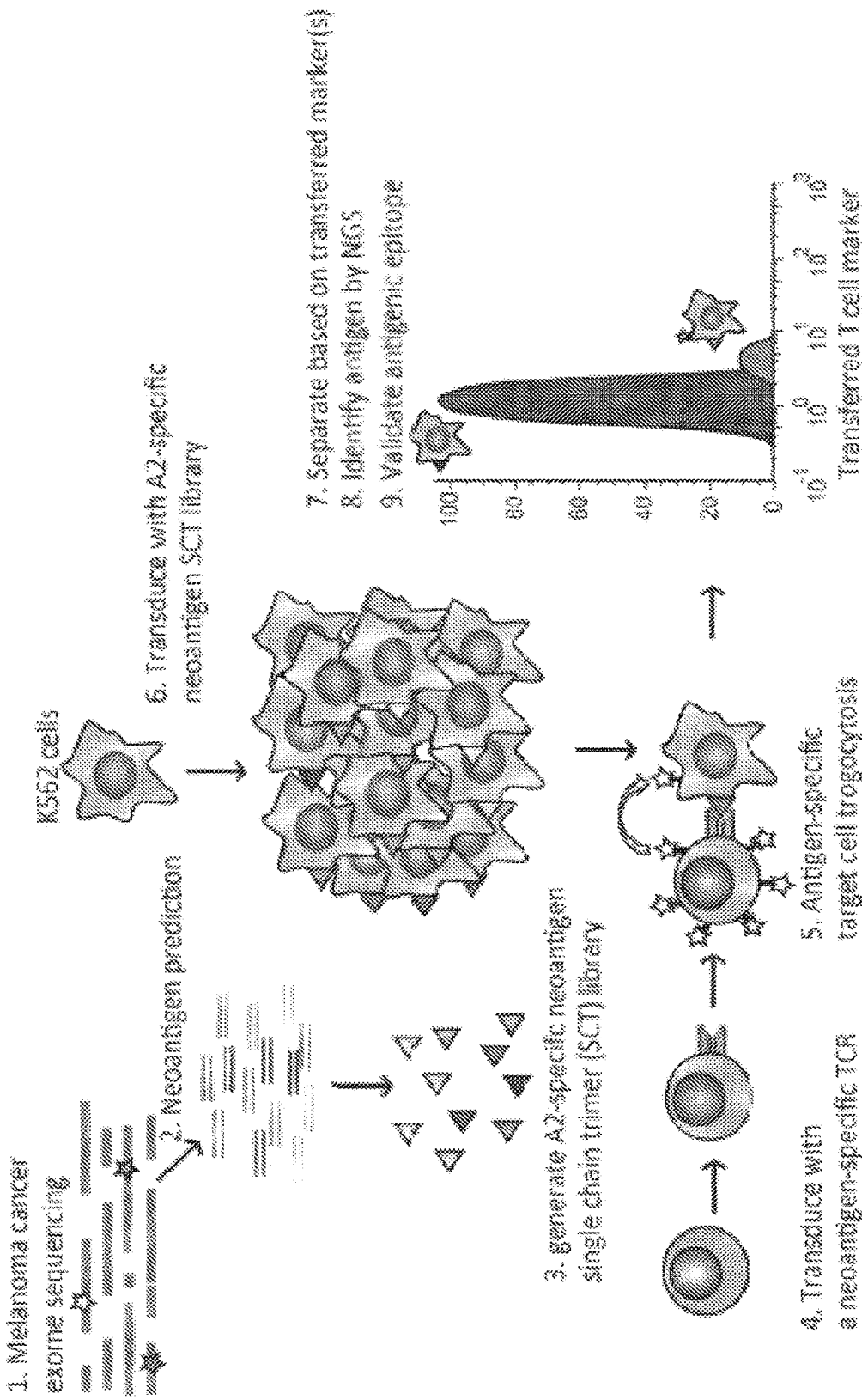

Example 5: Target Cell Trogocytosis Identifies the Ligand of a Patient-Derived Neoantigen-Specific TCR Recent advances in genomics and proteomics, along with supportive bioinformatics and in silico prediction tools, have enabled the rapid identification of mutated neoepitopes from patient-derived tumors[24, 25]. Having validated that target cell trogocytosis correctly identifies the cognate TCR ligand from a public epitope library, applications for target cell trogocytosis was further examined in the context of neoepitope ligand discovery for a tumor-infiltrating lymphocyte (TIL)-derived orphan TCR from a custom library of patient-specific neoepitopes (FIG. 5a). Private mutations were identified by exome/RNA sequencing of tumor material from a patient with metastatic melanoma and potential neoepitope ligands generated by the mutations were predicted algorithmically for presentation by HLA-A*02:01. Previous work used a pMHC multimer panel to screen TILs taken from the same patient to isolate a neoepitope-reactive TCR (not shown). A neoepitope SCT cDNA library was generated comprising 3,251 unique neoepitopes ranging from 8-12 amino acids in length and transduced into K562 cells to generate target a neoepitope target cell library. The K562 neoepitope target cell library was co-incubated with neoTCR-transduced Jurkat cells (neoTCR-Jurkat), and two rounds of sorting for trogocytosis⁺ target cells were performed. Sorted target cells were analyzed by NGS to identify the enriched neoepitopes. The top five ligands enriched after two rounds of selection were overlapping mutated peptides derived from ubiquitin specific peptidase 7 (USP7) (FIG. 5b). To verify that the neoTCR recognizes the enriched neoepitopes, K562 cells were transduced with an SCT encoding the core 9-mer mutant peptide YLYHRVDVI (SEQ ID NO:7) (mutUSP7-K562) contained in all enriched hits. As expected, an increased percentage of trogocytosis+ target cells was observed following co-incubation of mutUSP7-K562 with neoTCR-Jurkat cells than with non-cognate F5-Jurkat cells (FIG. 5c), demonstrating that the USP7 mutant epitope YLYHRVDVI (SEQ ID NO:7) is recognized by the neoTCR. Recognition of the USP7 mutant epitope by the neoTCR was further validated by measuring the ability of the neoTCR to induce cytotoxicity upon recognition of neoepitope-presenting target cells. Primary T cells transduced with neoTCR killed mutUSP7-K562 target cells in an antigen-specific and an effector:target cell ratio dependent manner (FIG. 5d), validating that the neoTCR functionally targets the USP7mut epitope identified through target cell trogocytosis. Quantification of percent lysis is presented in Table A.

TABLE A

| Specific Cytotoxic Killing (Avg. % Specific Lysis) | | | |
|---|---|---|---|
| E:T Ratio | NeoTCR-T cell + MART1-K562 | F5-T cell + MART1-K562 | NeoTCR-T cell + USP7mut-K562 | F5-T cell + USP7mut-K562 |
| 16 to 1 | 0.031407 | 0.593186 | 0.60109 | 0 |
| 8 to 1 | 0.058263 | 0.377042 | 0.374347 | 0.040552 |
| 4 to 1 | 0.050916 | 0.268119 | 0.30848 | 0.036563 |
| 2 to 1 | 0.053568 | 0.159843 | 0.223432 | 0.064363 |

Example 6: Parallel Screening to Identify Neoepitopes and Cognate TCRs

Patient specific neoepitopes and cognate TCRs are identified using the above described methods.

For identification of a patient's putative neoantigens (tumor or pathogen), in silico predictive algorithmic programs are utilized that analyze the tumor, viral, or bacterial sequencing data, including whole genome, whole exome, or transcriptome sequencing data, to identify somatic mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, Cancer Immunol Res., 2:522-529, the entire contents of which are herein incorporated by reference. Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

The potential neoepitopes are cloned into expression vectors, such as the SCT retroviral expression vectors previously described. An MHC expressing cell, such as a k562 cells engineered to express a single MHC or alternatively engineered to express multiple MHCs (e.g., each of the MHC alleles of a patient), is transduced or transfected with the neoepitope expression vectors to form a neoepitope expressing target cell library.

The target cell library is co-incubated with cells that express TCRs derived from the patient, for example primary T cells directly isolated from a patient sample or cells engineered to express TCRs determined to present in the patient. Criteria for selecting patient specific TCRs to screen can include TCRs known to be present in a subject or patient, selecting TCRs known to be present at a certain frequency in a subject or patient, TCRs known to be expressed by a particular T cell or T cells characterized by a particular phenotype, for example activated T cells (e.g., characterized as PD-1+, CD39+, and/or CD137+) or exhausted T cells. Methods of identifying potential TCR sequences of interest within a population are known in the art, for example Issued U.S. Pat. No. 8,507,205, Issued U.S. Pat. No. 9,347,099, Issued U.S. Pat. No. 9,506,119, International Application WO2018075693, Han et al. 2014, Briggs et al. 2017, Gros et al. 2014, Pricket et al. 2016, Linneman et al. 2014, Pasetto et al. 2014, and International Application PCT/US18/21611, each of which is incorporated by reference for all purposes.

Following co-incubation of target cells and TCR expressing cells, cells are sorted based upon transfer of membrane markers. Target cells expressing neoepitopes that are recognized by TCRs are sorted based on the presence of membrane markers derived from a T cell or TCR expressing cell. In addition or alternatively, cells expressing TCRs that recognize potential neoepitopes are sorted based on the presence of membrane markers derived from a target cell. Alternatively, target cells or T cell/TCR expressing cells of interest are sorted based upon loss of their respective membrane components.

DNA or mRNA from the sorted target cell and/or the T cell/TCR expressing cell is isolated and sequenced by next generation sequencing, and the neoepitope and/or TCR is identified.

Example 7: Parallel Barcoding of Membrane Components

DNA barcodes are conjugated to antibodies using a commercial kit following the manufacturer's instructions (Solulink All-in-One Antibody-Oligonucleotide Conjugation Kit). Briefly, amino-modified DNA oligos (consisting of a barcode flanked by two universal primer sites) are conjugated to sulfo-S-4FB, thereby decorating the oligo with 4-FB. In parallel, antibodies are conjugated to bifunctional HyNic-NHS ester, thereby decorating an antibody surface Lys residues with HyNic groups. Next, in each well of a multi-well plate, HyNic-modified antibodie are reacted with a unique 4-FB modified oligo (or with unique combinatorial panel of 4-FB modified oligos), the unique 4-FB modified oligo specific to each well.

The oligos (i.e., barcodes) take the form: UPS1-NAANGGNAANGGNAAN (SEQ ID NO:1 UPS2, where N represents a random nucleotide. The universal primer sites UPS1 and UPS2 contain no adjacent AA or GG dinucleotides.

The antibody is a commercial antibody directed against proteins on the T cell surface (e.g., endogenous proteins such as CD8a, CD3e, TCR-beta, CD2 or exogenous proteins such as LNGFR, surface-expressed epitope tags)

In a series of experiments, HyNic-anti-CD8a (clone HIT8a) is distributed across 96 wells of a 96-well plate, and then 96 unique 4-FB oligo barcodes (or 96 unique combinations of 4-FB oligo barcodes) are added to the 96 wells, resulting in a stable bis-arylhydrazone bond between the antibody and each oligo generating a panel of barcoded anti-CD8 antibodies.

Orphan TCRs from a panel of interesting orphan TCRs (e.g., the top 100 most frequent TCRs from TILs, or TCRs derived from T cells expressing CD39 and/or CD103 and/or PD-1 at the tumor site) are then labeled with the barcoded antibodies. Jurkat T cells expressing 96 different orphan TCRs are segregated into 96 wells, each well containing cells that express only one orphan TCR. The 96 uniquely barcoded anti-CD8a antibodies generated above are added to the 96 unique orphan TCR-expressing Jurkat cell wells, incubated to allow binding, and then washed to remove unbound barcoded antibodies.

Following the wash step, uniquely barcoded, orphan TCR-expressing T cells are combined in a single pool and then incubated with a library of target cells in a trogocytosis reaction. Membrane protein transfer from T cells to cognate epitope-expressing members of the target cell library enable identification and isolation of those target cells that interact with one or several of the orphan TCRs being interrogated. Specifically, trogocytosis+ target cells that demonstrate a $TCR^{high}$ phenotype are sorted by FACS. CD8 is among the membrane proteins transferred to trogocytosis+ target cells. Thus, sorted trogocytosis+ target cells possess a barcoded anti-CD8 antibody. Trogocytosis+ target cells are analyzed by NGS to identify both the epitopes encoded by the target cell and the barcoded oligo associated with the anti-CD8 antibody. Thus, in a single experiment all neoepitope-reactive TCRs responding to the tumor and the epitopes driving that immune response are identified.

In another series of experiments, trogocytosis+ cells are sorted as single cells (or sorted in bulk and then analyzed by single cell Drop-seq), are analyzed by NGS such that all TCRs mediating anti-tumor immunity, all epitopes driving the immune response, and additionally the TCR:epitope cognate pairs are identified (i.e. barcode(s) and epitope sequencing results from a single cell identify one or more cognate TCR-epitope pairs).

Example 8: Discussion

As discovered and presented here, antigen-presenting target cells extract membrane-associated proteins from interacting T cells in an antigen-specific and pMHC-density-dependent manner. This phenomenon, termed trogocytosis, has been shown here to provide a platform for marking ligand-presenting target cells with extracted TCRs (and other membrane proteins) from cognate T cells, enabling ligand discovery. The platform has been validated using both public and neoepitope-specific TCRs. Target cells presenting cognate pMHC could be identified by the transfer of any of multiple proteins that were involved in the T cell synapse (TCR, CD3, and CD8) or that were not LNGFRΔ. Thus, the platform was validated using multiple independent, commercially-available reagents (i.e. antibodies). Top epitopes identified using the trogocytosis platform reliably returned biological target ligands for the TCR being tested. The trogocytosis platform also demonstrated a readily detectable and resolvable population of Jurkat T cells that lose TCRs from their surface in an antigen-specific manner allowing for identification of T cells and their respective TCRs in parallel to identification of epitopes.

In summary, the trogocytosis-based method enables rapid identification of epitopes targeted by T cell-mediated immunity, a key goal in basic and translational research in the fields of infectious disease, tumor immunology, autoimmunity, and immunotherapy.

Example 9: Other Embodiments

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Dembic, Z. et al. Transfer of specificity by murine alpha and beta T-cell receptor genes. *Nature* 320, 232-238 (1986).
2. Schumacher, T. N. & Schreiber, R. D. Neoantigens in cancer immunotherapy. *Science* 348, 69-74 (2015).
3. Sollid, L. M. et al. Small bowel, celiac disease and adaptive immunity. *Digestive diseases* 33, 115-121 (2015).
4. Rosenberg, S. A. & Restifo, N. P. Adoptive cell transfer as personalized immunotherapy for human cancer. *Science* 348, 62-68 (2015).
5. Kontos, S., Grimm, A. J. & Hubbell, J. A. Engineering antigen-specific immunological tolerance. *Current opinion in immunology* 35, 80-88 (2015).
6. Dolton, G. et al. More tricks with tetramers: a practical guide to staining T cells with peptide-MHC multimers. *Immunology* 146, 11-22 (2015).
7. Bentzen, A. K. et al. Large-scale detection of antigen-specific T cells using peptide-MHC-I multimers labeled with DNA barcodes. *Nature biotechnology* 34, 1037-1045 (2016).
8. Gros, A. et al. Prospective identification of neoantigen-specific lymphocytes in the peripheral blood of melanoma patients. *Nature medicine* 22, 433-438 (2016).
9. Stronen, E. et al. Targeting of cancer neoantigens with donor-derived T cell receptor repertoires. *Science* 352, 1337-1341 (2016).
10. Gros, A. et al. PD-1 identifies the patient-specific CD8 (+) tumor-reactive repertoire infiltrating human tumors. *The Journal of clinical investigation* 124, 2246-2259 (2014).
11. Prickett, T. D. et al. Durable Complete Response from Metastatic Melanoma after Transfer of Autologous T Cells Recognizing 10 Mutated Tumor Antigens. *Cancer immunology research* 4, 669-678 (2016).

12. Linnemann, C., Mezzadra, R. & Schumacher, T. N. TCR repertoires of intratumoral T-cell subsets. *Immunological reviews* 257, 72-82 (2014).
13. Pasetto, A. et al. Tumor- and Neoantigen-Reactive T-cell Receptors Can Be Identified Based on Their Frequency in Fresh Tumor. *Cancer immunology research* 4, 734-743 (2016).
14. Gee, M. H. et al. Antigen Identification for Orphan T Cell Receptors Expressed on Tumor-Infiltrating Lymphocytes. *Cell* 172, 549-563 e516 (2018).
15. Joly, E. & Hudrisier, D. What is trogocytosis and what is its purpose? *Nat Immunol* 4, 815 (2003).
16. Daubeuf, S., Lindorfer, M. A., Taylor, R. P., Joly, E. & Hudrisier, D. The direction of plasma membrane exchange between lymphocytes and accessory cells by trogocytosis is influenced by the nature of the accessory cell. *Journal of immunology* 184, 1897-1908 (2010).
17. Uzana, R. et al. Human T cell crosstalk is induced by tumor membrane transfer. *PloS one* 10, e0118244 (2015).
18. Daubeuf, S., Puaux, A. L., Joly, E. & Hudrisier, D. A simple trogocytosis-based method to detect, quantify, characterize and purify antigen-specific live lymphocytes by flow cytometry, via their capture of membrane fragments from antigen-presenting cells. *Nature protocols* 1, 2536-2542 (2006).
19. Puaux, A. L. et al. A very rapid and simple assay based on trogocytosis to detect and measure specific T and B cell reactivity by flow cytometry. *European journal of immunology* 36, 779-788 (2006).
20. Machlenkin, A. et al. Capture of tumor cell membranes by trogocytosis facilitates detection and isolation of tumor-specific functional CTLs. *Cancer research* 68, 2006-2013 (2008).
21. Irvine, D. J., Purbhoo, M. A., Krogsgaard, M. & Davis, M. M. Direct observation of ligand recognition by T cells. *Nature* 419, 845-849 (2002).
22. Skipper, J. C. et al. Mass-spectrometric evaluation of HLA-A*0201-associated peptides identifies dominant naturally processed forms of CTL epitopes from MART-1 and gp100. *International journal of cancer* 82, 669-677 (1999).
23. Wooldridge, L. et al. Interaction between the CD8 coreceptor and major histocompatibility complex class I stabilizes T cell receptor-antigen complexes at the cell surface. *The Journal of biological chemistry* 280, 27491-27501 (2005).
24. Bassani-Sternberg, M. & Coukos, G. Mass spectrometry-based antigen discovery for cancer immunotherapy. *Current opinion in immunology* 41, 9-17 (2016).
25. Bethune, M. T. & Joglekar, A. V. Personalized T cell-mediated cancer immunotherapy: progress and challenges. *Current opinion in biotechnology* 48, 142-152 (2017).
26. Han, A., Glanville, J., Hansmann, L. & Davis, M. M. Linking T-cell receptor sequence to functional phenotype at the single-cell level. *Nature biotechnology* 32, 684-692 (2014).
27. Briggs, A. W. et al. Tumor-infiltrating immune repertoires captured by single-cell barcoding in emulsion. *BioRxiv*, 1-34 (2017).
28. Gonzalez-Galarza, F. F. et al. Allele frequency net 2015 update: new features for HLA epitopes, KIR and disease and HLA adverse drug reaction associations. *Nucleic acids research* 43, D784-788 (2015).
29. Tran, E. et al. Cancer immunotherapy based on mutation-specific CD4+ T cells in a patient with epithelial cancer. *Science* 344, 641-645 (2014).
30. Lu, Y. C. & Robbins, P. F. Cancer immunotherapy targeting neoantigens. *Semin Immunol* 28, 22-27 (2016).
31. Morgan, R. A. et al. Cancer regression and neurological toxicity following anti-MAGE-A3 TCR gene therapy. *Journal of immunotherapy* 36, 133-151 (2013).
32. Bethune, M. T. et al. Domain-swapped T cell receptors improve the safety of TCR gene therapy. *eLife* 5 (2016).
33. Bethune, M. T., Comin-Anduix, B., Hwang Fu, Y. H., Ribas, A. & Baltimore, D. Preparation of peptide-MHC and T-cell receptor dextramers by biotinylated dextran doping. *BioTechniques* 62, 123-130 (2017).
34. Neri, S., Mariani, E., Meneghetti, A., Cattini, L. & Facchini, A. Calcein-acetyoxymethyl cytotoxicity assay: standardization of a method allowing additional analyses on recovered effector cells and supernatants. *Clinical and diagnostic laboratory immunology* 8, 1131-1135 (2001).
35. Shi, H. B. et al. Acquired Resistance and Clonal Evolution in Melanoma during BRAF Inhibitor Therapy. *Cancer Discov* 4, 80-93 (2014).
36. Cibulskis, K. et al. Sensitive detection of somatic point mutations in impure and heterogeneous cancer samples. *Nat Biotechnol* 31, 213-219 (2013).
37. Koboldt, D. C. et al. VarScan 2: Somatic mutation and copy number alteration discovery in cancer by exome sequencing. *Genome Res* 22, 568-576 (2012).
38. Ramos, A. H. et al. Oncotator: Cancer Variant Annotation Tool. *Hum Mutat* 36, E2423-E2429 (2015).
39. Kim, D. et al. TopHat2: accurate alignment of transcriptomes in the presence of insertions, deletions and gene fusions. *Genome Biol* 14 (2013).
40. Trapnell, C. et al. Differential gene and transcript expression analysis of RNA-seq experiments with TopHat and Cufflinks. *Nat Protoc* 7, 562-578 (2012).
41. Lundegaard, C. et al. NetMHC-3.0: accurate web accessible predictions of human, mouse and monkey MHC class I affinities for peptides of length 8-11. *Nucleic Acids Res* 36, W509-W512 (2008).

The invention claimed is:

1. A method of antigen or antigen-specific TCR identification, comprising:
   a) providing one or more T cell receptor (TCR)-expressing cell populations comprising a first immortalized cell line engineered to express one or more exogenous TCRs;
   b) providing one or more target cell populations comprising a second immortalized cell line, wherein target cells of the one or more target cell populations are engineered to present one or more peptides that are 7-35 amino acids in length on one or more major histocompatibility complex (MHC) alleles;
   c) contacting the one or more TCR-expressing cell populations with the one or more target cell populations under conditions sufficient to allow at least one TCR-expressing cell of the one or more TCR-expressing cell populations to specifically interact with at least one target cell of the one or more target cell populations, whereby one or more membrane components are transferred between the at least one TCR-expressing cell and the at least one target cell;
   d) isolating or having isolated
      i) the at least one target cell, at least based on detecting in the at least one target cell the one or more membrane components transferred from the at least one TCR-expressing cell following the contacting step (c), and/or
      ii) the at least one TCR-expressing cell, at least based on detecting in the at least one TCR-expressing cell
         (1) the one or more membrane components transferred from the at least one target cell following the contacting step (c), and/or
         (2) the loss of the one or more membrane components transferred from the at least one TCR-expressing antigen cell following the contacting step (c); and
   e) determining or having determined
      i) a sequence of the one or more peptides associated with the isolated at least one target cell,
      ii) at least a portion of a TCR sequence of a TCR peptide associated with the isolated at least one TCR-expressing cell, or
      iii) a sequence of one or more peptides associated with the isolated at least one target cell and at least a portion of a TCR sequence of a TCR peptide associated with the isolated at least one TCR-expressing cell.

2. The method of claim 1, wherein at least one of the one or more antigen-specific T cell populations is isolated from a subject known or suspected to have cancer.

3. The method of claim 1, wherein the one or more exogenous TCRs are identified or have been identified in a tumor sample.

4. The method of claim 1, wherein at least one of the one or more MHC alleles comprises an exogenous MHC allele.

5. The method of claim 1, wherein at least one of the one or more MHC alleles comprises a single chain trimer (SCT).

6. The method of claim 1, wherein the one or more peptides comprises a neoepitope, and wherein the method comprises analyzing tumor, viral, or bacterial sequencing data from a subject to identify one or more somatic mutations, to select the neoepitope.

7. The method of claim 1, wherein
the one or more membrane components transferred from the at least one TCR-expressing cell comprises a TCR-expressing cell membrane component selected from the group consisting of: a TCR; a TCR co-receptor, a CD3 TCR co-receptor, a CD4 TCR co-receptor, and a CD8 TCR co-receptor; and/or
the one or more membrane components transferred from the at least one target cell comprises a target cell membrane component comprising an MHC allele.

8. The method of claim 1, wherein at least one of the one or more membrane components comprises a labeled membrane component.

9. A method of antigen identification, comprising:
a) providing one or more T cell receptor (TCR)-expressing cell populations comprising a first immortalized cell line engineered to express one or more exogenous TCRs;
b) providing one or more target cell populations comprising a second immortalized cell line, wherein target cells of the one or more target cell populations are engineered to present one or more peptides that are 7-35 amino acids in length on one or more major histocompatibility complex (MHC) alleles;
c) contacting the one or more TCR-expressing cell populations with the one or more target cell populations under conditions sufficient to cause an antigen-specific interaction between at least one TCR-expressing cell of the one or more TCR cell populations and at least one target cell of the one or more target cell populations, whereby one or more membrane components are transferred between the at least one TCR-expressing cell and the at least one target cell;
d) isolating or having isolated the at least one target cell, at least based on detecting in the at least one target cell the one or more membrane components transferred from the at least one TCR-expressing cell following the contacting step (c); and
e) determining or having determined a sequence of the one or more peptides associated with the isolated at least one target cell.

10. The method of claim 9, wherein the one or more membrane components transferred from the at least one TCR-expressing cell comprises a TCR-expressing cell membrane component selected from the group consisting of: a TCR; a TCR co-receptor, a CD3 TCR co-receptor, a CD4 TCR co-receptor, and a CD8 TCR co-receptor.

11. The method of claim 1, wherein the first immortalized cell line comprises an immortalized T cell line.

12. The method of claim 1, wherein the first immortalized cell line and the second immortalized cell line are each selected from: an immortalized T cell line, K562 cells, HEK293 cells, 3T3 cells, Chinese Hamster Ovary (CHO) cells, or HeLa cells.

13. The method of claim 1, wherein the first immortalized cell line and the second immortalized cell line are each selected from: Jurkat cells, K562 cells, HEK293 cells, 3T3 cells, Chinese Hamster Ovary (CHO) cells, or HeLa cells.

14. The method of claim 1, wherein the first immortalized cell line and the second immortalized cell line are different immortalized cell lines.

15. The method of claim 9, wherein the first immortalized cell line comprises an immortalized T cell line.

16. The method of claim 9, wherein the first immortalized cell line and the second immortalized cell line are each selected from: an immortalized T cell line, K562 cells, HEK293 cells, 3T3 cells, Chinese Hamster Ovary (CHO) cells, or Hela cells.

17. The method of claim 9, wherein the first immortalized cell line and the second immortalized cell line are each selected from: Jurkat cells, K562 cells, HEK293 cells, 3T3 cells, Chinese Hamster Ovary (CHO) cells, or Hela cells.

18. The method of claim 9, wherein the first immortalized cell line and the second immortalized cell line are different immortalized cell lines.

19. The method of claim 1, wherein contacting at (c) comprises co-incubating the one or more TCR-expressing cell populations with the one or more target cell populations at a ratio of TCR-expressing cells to target cells of about 1:1 to about 5:1.

20. The method of claim 1, wherein the ratio of (1) the number of target cells presenting on one or more MHC alleles a peptide that is specifically bound by a TCR expressed by a TCR-expressing cell of the one or more TCR-expressing cell populations, to (2) the number of target cells not presenting on one or more MHC alleles the specifically bound peptide, is about 1:1 to about 1:10,000.

21. A method of antigen or antigen-specific TCR identification, comprising:
a) providing one or more T cell receptor (TCR)-expressing cell populations comprising a first immortalized cell line selected from an immortalized T cell line, K562 cells, HEK293 cells, 3T3 cells, Chinese Hamster Ovary (CHO) cells, or HeLa cells, wherein the first immortalized cell line is engineered to express one or more exogenous TCRs;
b) providing one or more target cell populations comprising a second immortalized cell line selected from an immortalized T cell line, K562 cells, HEK293 cells, 3T3 cells, CHO cells, or HeLa cells, wherein the one or more target cell populations are engineered to present one or more peptides that are 7-35 amino acids in length on one or more major histocompatibility complex (MHC) alleles;
c) co-incubating the one or more TCR-expressing cell populations with the one or more target cell populations under conditions sufficient to induce trogocytosis, whereby one or more membrane components are transferred between at least one TCR-expressing cell of the one or more TCR-expressing cell populations and at least one target cell of the one or more target cell populations;
d) isolating or having isolated
  i) the at least one target cell, at least based on detecting in the at least one target cell the one or more membrane components transferred from the at least one TCR-expressing cell following the co-incubating in (c), and/or
  ii) the at least one TCR-expressing cell, at least based on detecting in the TCR-expressing cell
    (1) the one or more membrane components transferred from the at least one target cell following the co-incubating in (c), and/or
    (2) the loss of the one or more membrane components transferred from the at least one TCR-expressing cell following the co-incubating in (c);
  and
e) determining or having determined
  i) a sequence of the one or more peptides associated with the isolated at least one target cell, ii) at least a portion of a TCR sequence of a TCR peptide associated with the isolated at least one TCR-expressing cell, or iii) both e-i) and e-ii).

* * * * *

SEQUENCE LISTING

<160> NUMBER OF SEQ ID NOS: 70

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)

<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 1
naanggnaan ggnaan                                                  16

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Leu Met Trp Ile Thr Gln Val
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Leu Ala Gly Ile Gly Ile Leu Thr Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Leu Thr His Arg Val Asp Val Ile
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Glu Ala Ala Gly Ile Gly Ile Leu Thr Val
1               5                   10
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ser Leu Leu Met Trp Ile Thr Gln Cys
1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Tyr Leu Tyr His Arg Val Asp Val Ile
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Ala Ala Gly Ile Gly Ile Leu Thr Val
1               5
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Ala Ala Gly Ile Gly Ile Leu Thr Val Ile
1               5                   10
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Gly Ile Gly Ile Leu Thr Val Ile Leu
1               5
```

<210> SEQ ID NO 11
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 11

Ile Leu Val Ile Leu Gly Val Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Leu Leu Met Trp Ile Thr Gln
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Leu Leu Met Trp Ile Thr Gln Ala Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Asn Glu Glu Ile Ala Arg Val
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Gln Glu Gln Leu Glu Ala Thr Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Leu Met Gln Asn Trp Glu His Val Leu
1               5                   10
```

```
<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile His Asp Leu Leu Glu Pro Lys Gly Pro Leu
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Ile Val Ser Glu Asp Gly Leu Ile Val Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Leu Asp Glu Ser Thr Gln Glu Ser Lys Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Leu Pro Gly Val Ile Lys Thr Val
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Leu Asp Glu Gln Gln Val Asn Val
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

```
Ala Leu Asn Asp His Phe Val Lys Leu
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Leu Ala Gly Ile Gly Ile Leu Ala Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Leu Ala Gly Ile Gly Thr Val Pro Ile
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Leu Ala Ala Ile Gly Ile Leu Thr Val
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Leu Ala Gly Ile Gly Ile Leu Thr Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Val Ala Gly Ile Gly Ile Leu Thr Gly
1               5                   10

<210> SEQ ID NO 28
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 28

Glu Leu Ala Gly Ile Gly Ile Ala Thr Val
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Ala Gly Ile Gly Ile Leu Thr Val
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Leu Ala Ser Gln Val Val Lys Leu
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Leu Leu Asp His Ala Pro Pro Glu Ile
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Leu Ile Glu Glu Ile Gly Asp Val Leu Leu
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Leu Phe Glu Glu Ile Ala Lys Ile
1               5
```

```
<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Gly Leu Ala Pro Tyr Lys Leu Arg Pro Val
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gln Asn Pro Phe Arg Ser Glu Leu
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Leu Arg Ala Glu Ser Leu Pro Gly Ala
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Met Asp Glu Asn Leu Met His Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Leu Asp Glu Glu Leu Asp Arg Val
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Asn Leu Val Pro Ile Val Ala Thr Val
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Leu Tyr Asp Val Val Ser Lys Leu
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Leu Gly Asp Phe Pro Tyr Val Ser Ile
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Leu Asp Asp Lys Lys Val Tyr Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Leu Gln Ala Arg Val Val Glu Val
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Leu Asn Asp Arg Ser Asp Ala Val
1               5

<210> SEQ ID NO 45
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 45

Asn Leu Val Pro Met Val Ala Thr Val
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Leu Asp Glu Leu Gly Phe Leu Glu
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Gly Pro Ala Arg Pro Tyr Ile Gln Gln Ser
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Phe Ser Ala Lys Ala Gly Pro Ala Arg Pro
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Asp Ile Leu Leu Glu Tyr Arg Ile Ser
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Lys Met Lys Asn Tyr Asn Lys Ala
1               5
```

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Asp Asp Ser Arg Arg Cys Phe Gln Val Lys
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Leu Leu Cys Thr Asp Cys Tyr Phe
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Asp Pro Leu Phe Thr Asp Ile Leu
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Ser Met Val Leu Asp Ala Ser Glu Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Val Leu Leu His Ala Phe Glu Gly Tyr
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Lys Asn Phe Phe Val Glu Ala
1               5

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Ala Asn Trp Phe Leu Gln Leu Leu Ser Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Asp Gln Leu Asp Ser Gly Thr Leu Ile
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Asp Thr Lys Gly Phe Phe Asn Pro Asn Thr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Lys Ser Thr Phe Asp Arg Leu Gly Gly Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Arg Gly Cys His His Gly Ser Ala Pro
1               5                   10

<210> SEQ ID NO 62
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Tyr Leu Tyr His Arg Val Asp Val Ile Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Tyr Leu Tyr His Arg Val Asp Val Ile
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Leu Tyr His Arg Val Asp Val Ile
1               5

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Leu Tyr His Arg Val Asp Val Ile Phe Cys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Leu Tyr His Arg Val Asp Val Ile Phe
1               5                   10

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caggagggct cggca                                                      15
```

```
<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gatgagcggc cgccggaccc tccgcatcc                                       29

<210> SEQ ID NO 69
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aatgatacgg cgaccaccga gatctacact ctttccctac acgacgctct tccgatctgg     60
cctgctttgt ttgcc                                                      75

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtgactggag ttcagacgtg tgctcttccg atctcctcca ccaccgctac ctc            53
```